United States Patent
Liu et al.

(10) Patent No.: US 10,350,210 B2
(45) Date of Patent: Jul. 16, 2019

(54) EGFR AND ALK DUAL INHIBITOR

(71) Applicant: PRECEDO PHARMACEUTICALS CO., LTD, Hefei, Anhui (CN)

(72) Inventors: Jing Liu, Anhui (CN); Qingsong Liu, Anhui (CN); Taoshan Jiang, Anhui (CN); Aoli Wang, Anhui (CN); Jiaxin Wu, Anhui (CN); Hong Wu, Anhui (CN); Ziping Qi, Anhui (CN); Yongfei Chen, Anhui (CN); Fengming Zou, Anhui (CN); Wenchao Wang, Anhui (CN); Zheng Zhao, Anhui (CN); Li Wang, Anhui (CN); Beilei Wang, Anhui (CN)

(73) Assignee: PRECEDO PHARMACEUTICALS CO., LTD, Hefei, Anhui (CN)

( * ) Notice: Subject to any disclaimer, the term of this patent is extended or adjusted under 35 U.S.C. 154(b) by 0 days.

(21) Appl. No.: 16/062,399

(22) PCT Filed: Dec. 15, 2016

(86) PCT No.: PCT/CN2016/110033
§ 371 (c)(1),
(2) Date: Jun. 14, 2018

(87) PCT Pub. No.: WO2017/101803
PCT Pub. Date: Jun. 22, 2017

(65) Prior Publication Data
US 2018/0369242 A1     Dec. 27, 2018

(30) Foreign Application Priority Data
Dec. 15, 2015  (CN) .......................... 2015 1 0946305

(51) Int. Cl.
*A61P 35/00*   (2006.01)
*A61K 31/5377*   (2006.01)
(Continued)

(52) U.S. Cl.
CPC ........ *A61K 31/506* (2013.01); *A61K 31/5377* (2013.01); *A61K 31/551* (2013.01);
(Continued)

(58) Field of Classification Search
CPC ... A61P 35/00; A61K 31/5377; A61K 31/551; C07D 239/47; C07D 239/48; C07D 401/12; C07D 403/12; C07D 409/12
See application file for complete search history.

(56) References Cited

U.S. PATENT DOCUMENTS 9,879,008 B2 *  1/2018  Lan .................. A61K 31/16

FOREIGN PATENT DOCUMENTS

| CN | 103501612 A | 1/2014 |
| CN | 104974140 A | 10/2015 |

(Continued)

OTHER PUBLICATIONS

International Search Report dated Mar. 21, 2017 issued in PCT/CN2016/110033.
(Continued)

*Primary Examiner* — Timothy R Rozof
(74) *Attorney, Agent, or Firm* — Scully, Scott, Murphy & Presser, P.C.

(57) ABSTRACT

The present application provides a compound of formula I, which is a EGFR and ALK dual inhibitor and can be used alone or in combination with other therapeutic agents to treat diseases such as non-small cell lung cancer. The compounds of the present application are useful in the treatment of diseases carrying the EGFR wild-type gene, or carrying the EGFR T790M mutant gene and/or the EGFR L858R mutant gene and/or the EGFR delE746_A750 mutant gene, or in the treatment of diseases carrying the ALK wild-type gene, ALK F1174L mutant gene and/or ALK F1196M gene and/or
(Continued)

EML4-ALK mutant gene and/or NPM-ALK mutant gene, and can be used in the first-line treatment of anaplastic lymphoma kinase (ALK) positive late-stage non-small cell Lung cancer.

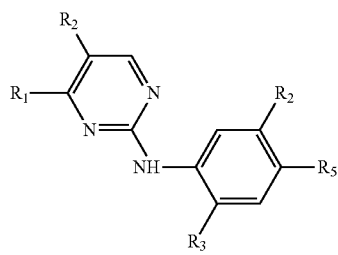

(I)

18 Claims, 14 Drawing Sheets

(51) Int. Cl.
| | | |
|---|---|---|
| A61K 31/551 | (2006.01) | |
| C07D 239/47 | (2006.01) | |
| C07D 239/48 | (2006.01) | |
| C07D 401/12 | (2006.01) | |
| C07D 403/12 | (2006.01) | |
| C07D 409/12 | (2006.01) | |
| A61K 31/506 | (2006.01) | |

(52) U.S. Cl.
CPC ............ *A61P 35/00* (2018.01); *C07D 239/47* (2013.01); *C07D 239/48* (2013.01); *C07D 401/12* (2013.01); *C07D 403/12* (2013.01); *C07D 409/12* (2013.01); *Y02P 20/55* (2015.11)

(56) References Cited

FOREIGN PATENT DOCUMENTS

| | | |
|---|---|---|
| CN | 105085483 A | 11/2015 |
| WO | WO 2013/169401 A1 | 11/2013 |
| WO | WO2015/158233 | * 10/2015 |

OTHER PUBLICATIONS

Schiller et al., "Comparison of Four Chemotherapy Regimens for Advanced Non-Small-Cell Lung Cancer", The New England Journal of Medicine (Jan. 10, 2002), vol. 346, No. 2, pp. 92-98.

Yun et al., "The T790M mutation in EGFR kinase causes drug resistance by increasing the affinity for ATP", PNAS (Feb. 12, 2008), vol. 105, No. 6, pp. 2070-2075.

English-language translation of International Preliminary Report on Patentability dated Apr. 12, 2018 received in International Application No. PCT/CN2016/110033.

* cited by examiner

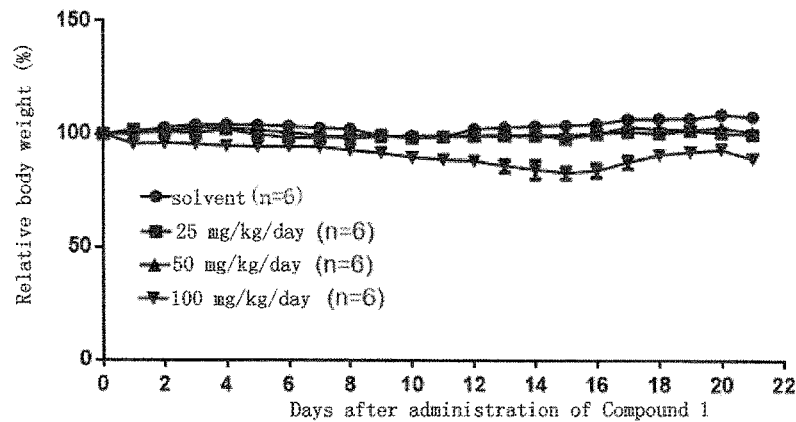
Fig. 4a
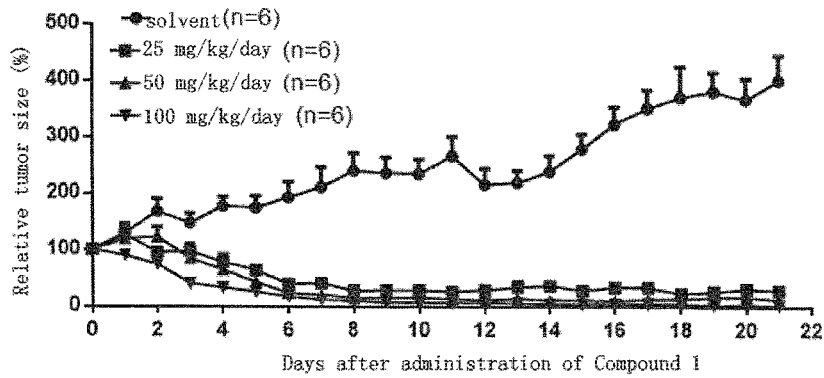
Fig. 4b
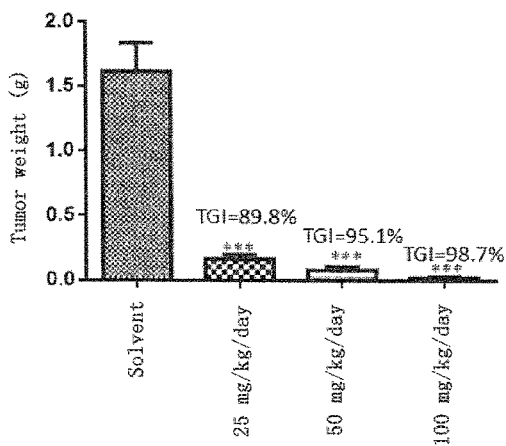 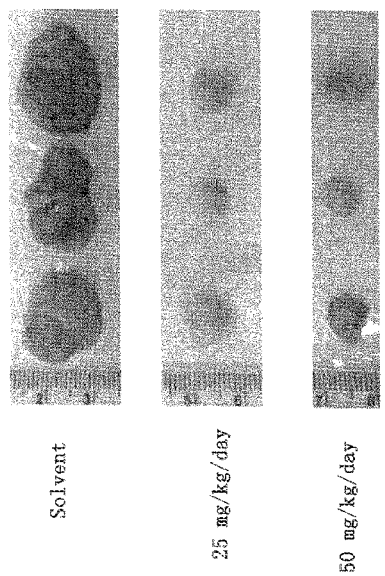
Fig. 4c  Fig. 4d

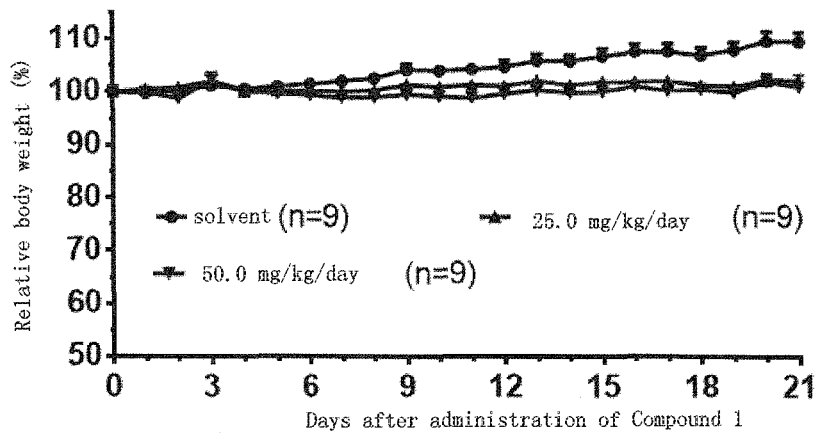
Fig. 5a
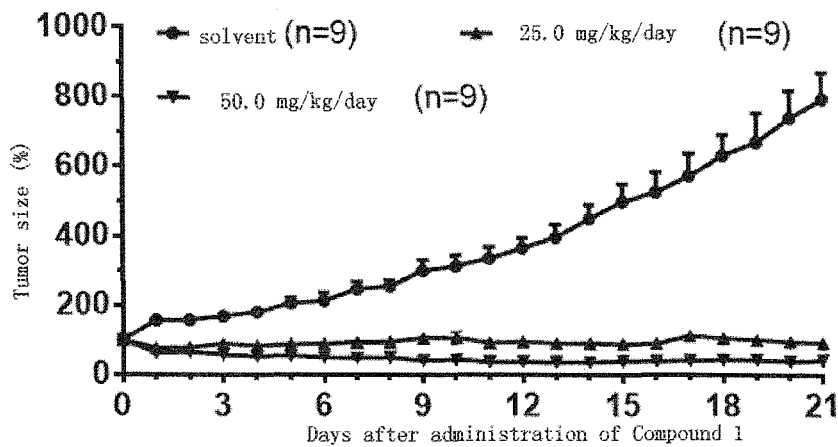
Fig. 5b
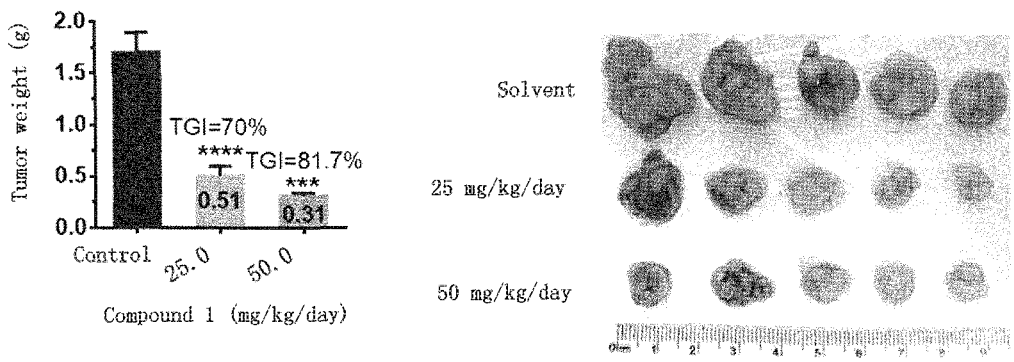
Fig. 5c
Fig. 5d

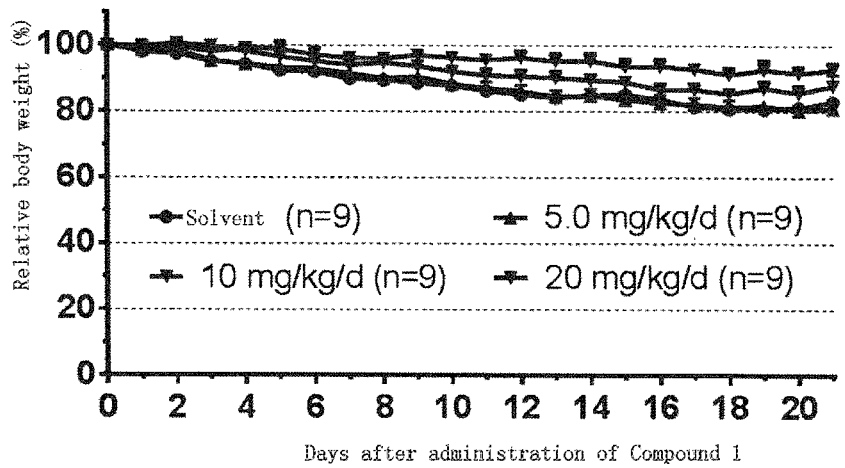
Fig. 6a
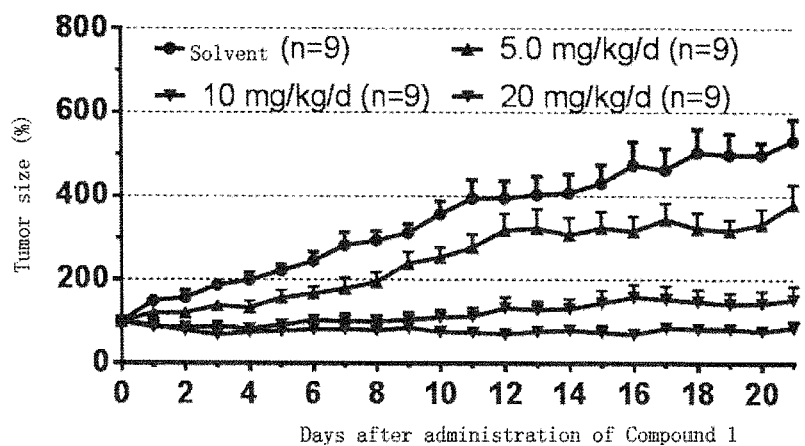
Fig. 6b
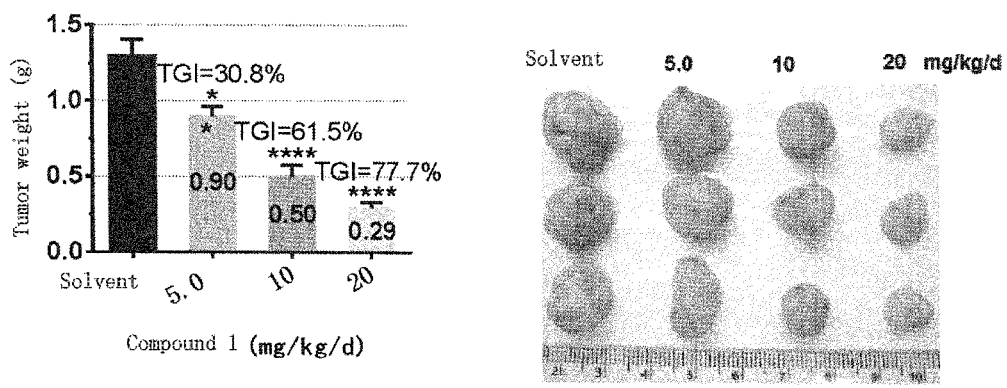
Fig. 6c                    Fig. 6d

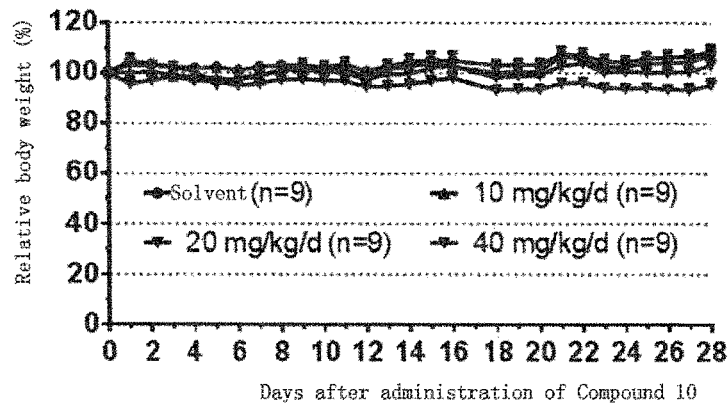
Fig. 7a
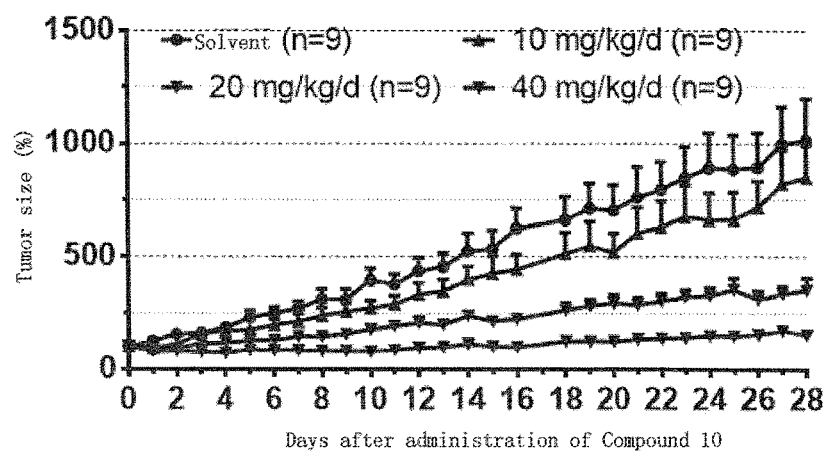
Fig. 7b
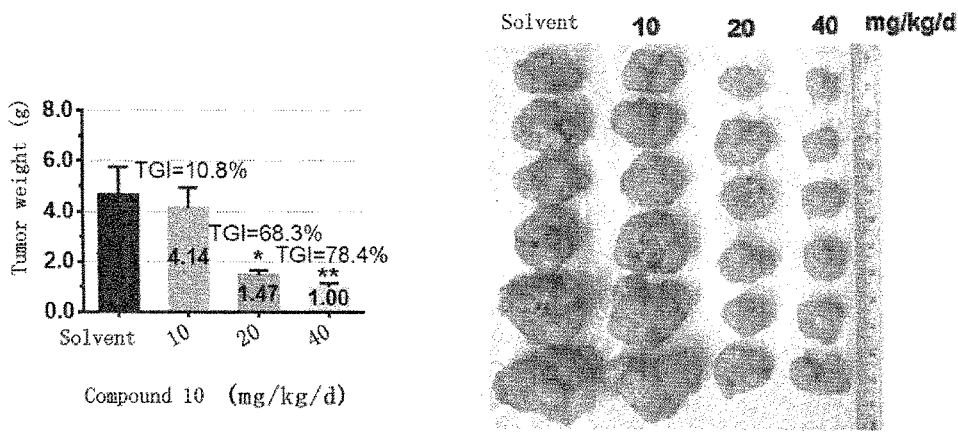
Fig. 7c
Fig. 7d

EGFR AND ALK DUAL INHIBITOR

FIELD OF THE INVENTION

The present disclosure relates to a novel tyrosine kinase inhibitor, especially a dual inhibitor of mutant and/or wild-type EGFR and ALK.

BACKGROUND OF THE INVENTION

Lung cancer is a clinically common malignant tumor in lungs. It is generally divided into two categories: small cell lung cancer (SCLC) and non-small cell lung cancer (NSCLC). The incidence of the non-small cell lung cancer all over the world is increasing year by year, which seriously threatens human health. Non-small cell lung cancer is the leading cause of cancer death in the United States, Japan, and Western European countries. For advanced patients, chemotherapy may improve survival to a certain extent, but chemotherapeutic drugs have significant toxicity to human body. Hence, there is a great need for therapeutic agents that can specifically target key genes involved in tumor growth (Schiller J H et al., N. Engl. J. Med., 346: 92-98, 2002).

ALK is an anaplastic lymphoma kinase (ALK). It was discovered in 2007 that there are rearrangements of echinoderm microtubule-associated protein-like 4 (EML4) gene and ALK gene due to chromosomal inversion in patients with lung cancer. Lung cancer with EML4-ALK gene rearrangement (also known as ALK-positive) is a newly discovered subtype that mainly occurs in NSCLC, accounting for approximately 3%-5% of lung cancer. The fusion protein encoded by the rearranged EML4-ALK fusion gene forms non-ligand dependent dimers, resulting in activation of constitutive ALK. ALK signal can lead to cell proliferation and production by activating RAS-MEK-ERK, JAK3-STAT3, and PI3K-AKT signaling pathways, thereby contributing to oncogenesis and progression of lung cancer. ALK translocation in NSCLC is associated with adenocarcinoma histology, signet ring cell morphology, young patients, and non-smoking history. A large-scale phase I study for Xalkori (crizotinib) which is an ALK inhibitor demonstrated an overall response rate of 57% and a disease control rate of 90% in cancer patients with ALK translocation, which resulted in FDA approval. More effective ALK inhibitors and strategies for targeting acquired drug resistance are under development. Although the proportion of ALK-positive NSCLC in lung cancer is very low, the number of new cases per year in China is still close to 35,000. Therefore, there is a need to accurately identify ALK-positive NSCLC, and offer an appropriate treatment.

EGFR (Epidermal Growth Factor Receptor) is a transmembrane glycoprotein which has tyrosine kinase activity and is widely distributed on cell membranes of various tissues of human body. Activating EGFR mutations are located in the tyrosine kinase domain and may cause constitutive EGFR signal. PI3K-AKT and RAS-MEK-ERK signals activated by EGFR mutation play a crucial role in growth, survival and migration of cancer cells. The most common activating mutations are an in-frame deletion mutation of exon 19 and a missense mutation of codon 858 (causing arginine to be replaced by leucine, L858R). Lung cancers with EGFR mutations are highly sensitive to EGFR tyrosine kinase inhibitors (TKIs). Currently, genotypic screening for EGFR mutations is often used to screen for patients who suffer from stage IV NSCLC and the first-line treatment for whom is to receive EGFR TKIs. The studies currently focus on prolonging the duration of the response and finding effective ways to target drug resistance mechanisms that are developed during disease progression. The most common drug resistance mechanism is EGFR/T790M mutation, which occurs in approximately 50% of resistant tumors. Certain other mechanisms such as MET amplification, PIK3CA mutation and transformation to SCLC have also been described.

By developing drugs that target cancer-specific gene mutations, the diagnosis and treatment of non-small cell lung cancer (NSCLC) have undergone major changes in recent years. Routine genetic testing of somatic mutations in lung cancer bioptic tissues is becoming the standard for providing the best medical care for the patients. Identification of specific mutations such as EGFR and ALK mutations provides guidance for the use of targeted therapies approved by FDA, which may be beneficial clinically. Discovery of other genetic mutations can also guide patients and physicians towards clinical trials of new targeted drugs.

Currently, tyrosine kinase inhibitors (TKI) that target EGFR (e.g., Iressa (Gefitinib) and Tarceva (Erlotinib)) have achieved great success in clinical treatment of non-small cell lung cancer. However, patients treated with TKI inhibitors often suffer from relapse due to the development of TKI resistance. Second-generation EGFR irreversible inhibitors such as Canertinib, Afatinib, Neratinib, Pelitinib etc. have entered clinical trials, but these molecules have poor selectivity for EGFR mutants, resulting in a low clinically tolerated drug dose. As a result, even when administrated at the maximum tolerated dose, the drug cannot reach the effective concentration in the body and thus is ineffective for most drug resistant patients.

In addition, according to the studies, in the treatment of non-small cell lung cancer sensitive to EGFR-TKI with Gefitinib or Erlotinib, patients often develop secondary drug resistance after 6-12 months, and about 50% among them have T790M mutation encoded by exon 20. Studies suggest that T790M mutation blocks the binding of EGFR with small-molecule inhibitors of EGFR (e.g., Gefitinib and Erlotinib) or increases the affinity of EGFR to ATP, resulting in drug resistance (Yun C H et al., Proc Natl Acad Sci USA. 2008 Feb. 12; 105(6):2070-5).

U.S. pharmaceutical giant Pfizer recently announced that the European Commission (EC) has approved product label updates for the extended use of oral targeted anti-cancer drug Crizotinib for the first-line treatment of adult patients with advanced anaplastic lymphoma kinase (ALK)-positive non-small cell lung cancer. Crizotinib is a small-molecule tyrosine kinase inhibitor (TKI) that targets anaplastic lymphoma kinase (ALK), ROS1 and MET, and was approved by FDA in 2011 for the treatment of patients with locally advanced or metastatic ALK-positive non-small cell lung cancer (NSCLC). Crizotinib is the world's first ALK inhibitor marketed and is currently approved in more than 80 countries. Clinically, Crizotinib is recognized as the standard nursing therapy for advanced ALK-positive NSCLC. Marketing of this drug has significantly changed the clinical care of patients with advanced ALK-positive NSCLC. To date, more than 20,000 patients have received Crizotinib therapy globally.

The compounds described herein are dual inhibitors of mutant EGFR and ALK that can be used alone or in combination with other therapeutic agents for the treatment of non-small cell lung cancer. Currently, there are reports of using the compounds described herein for the treatment of drug-resistant non-small cell lung cancer carrying EGFR T790M mutation and/or EGFR L858R mutation and/or EGFR delE746_A750 mutation and for first-line treatment of advanced anaplastic lymphoma kinase (ALK)-positive non-small cell lung cancer.

SUMMARY OF THE INVENTION

A compound of formula (I), or a pharmaceutically acceptable salt, solvate, ester, acid, metabolite or prodrug thereof:

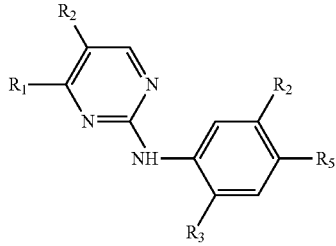

Formula I wherein:
$R_1$ is selected from the group consisting of H,

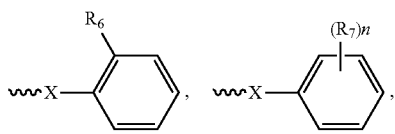

—X—$C_{3-6}$ cycloalkyl, or —X—$C_{1-6}$ alkylene-heteroaryl, wherein X is selected from the group consisting of —O—, —NH—, or —N($C_{1-6}$ alkyl)-, n=1, 2 or 3;
$R_2$ is selected from the group consisting of halo, $C_{1-6}$ alkyl, $C_{1-6}$ haloalkyl, $C_{1-6}$ alkoxy, nitro, amino, cyano or hydroxy;
$R_3$ is selected from the group consisting of H, $C_{1-6}$ alkoxy, $C_{1-6}$ haloalkoxy, or $C_{1-6}$ thioalkoxy;
$R_4$ is selected from the group consisting of —NH—(CO)—$C_{1-6}$ alkyl (e.g.,

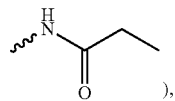

), or —NH—(CO)—$C_{2-6}$ alkenyl (e.g.,

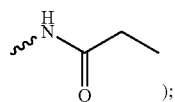

);

$R_5$ is selected from the group consisting of

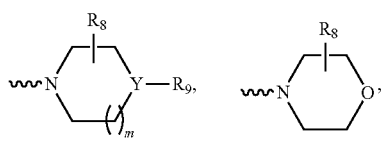

heteroaryl (e.g.,

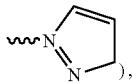

),

—O-heteroaryl (e.g.,

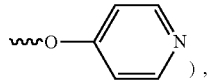

),

—O—$C_{1-6}$ alkylene-$C_{1-6}$ alkylamino (e.g.,

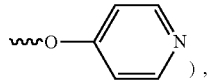

),

—O—$C_{1-6}$ alkylene-heterocyclyl (e.g.,

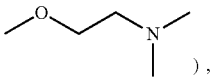

), or $C_{1-6}$ alkylamino substituted with $C_{1-6}$ alkylamino (e.g., (2-(dimethylamino)ethyl)(methyl)amino), wherein Y is selected from the group consisting of CH or N, m=1 or 2;
$R_6$ is selected from the group consisting of H, cyano, —(SO$_2$)—$C_{1-6}$ alkyl (e.g.,

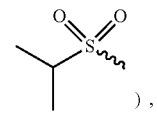

),

—(SO$_2$)—$C_{1-6}$ alkylamino (e.g.,

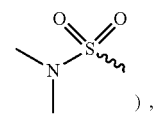

),

—(PO)($C_{1-6}$ alkyl)$_2$ (e.g., dimethylphosphinoyl), —(CO)—NH—$C_{1-6}$ alkyl (e.g., methylaminoacyl), or heteroarylalkoxy in which the heteroatom is optionally substituted with $C_{1-6}$ alkyl (e.g., (1-methyl-1H-imidazol-2-yl)methoxy);
$R_7$ are each independently selected from the group consisting of H, halogen, $C_{1-6}$ alkyl, $C_{1-6}$ haloalkyl, $C_{1-6}$ alkoxy, nitro, amino, cyano, hydroxy, or —NH-(amino-protecting group);
$R_8$ is selected from the group consisting of H, $C_{1-6}$ alkyl, halogen, $C_{1-6}$ haloalkyl, $C_{1-6}$ alkoxy, nitro, amino, cyano, or hydroxy;
$R_9$ is selected from the group consisting of H, $C_{1-6}$ alkyl (e.g., methyl, ethyl, or isopropyl), $C_{1-6}$ haloalkyl (e.g., fluoroethyl), amino-protecting group, $C_{1-6}$ alkoxy $C_{1-6}$ alkyl (e.g., methoxyethyl), $C_{3-8}$ cycloalkyl (e.g., cyclohexyl), $C_{1-6}$ alkylamino (e.g., dimethylamino), $C_{4-8}$ cycloalkylalkyl (e.g., cyclopropylmethyl), aryl $C_{1-6}$ alkyl (e.g., benzyl), heterocyclyl in which the heteroatom is optionally substituted with $C_{1-6}$ alkyl or $C_{1-6}$ alkylsulfonyl (e.g., piperidin-1-yl, N-morpholinyl, 1-methylpiperazin-4-yl, 1-methylpiperidin-4-yl, (1-methylsulfonyl)piperidin-4-yl, or 4-(methylsulfonyl)piperazin-1-ye, $C_{1-6}$ alkylsulfonyl (e.g., methylsulfonyl), or $C_{2-6}$ alkanoyl (e.g., ethanoyl);

the amino-protecting groups are each independently selected from the group consisting of pivaloyl (Piv), tert-butyloxycarbonyl (Boc), benzyloxycarbonyl (Cbz), 9-fluorenylmethyloxycarbonyl (FMOC), benzyl (Bn) or p-methoxyphenyl (PMP).

In preferred embodiments, $R_1$ is

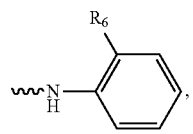

and $R_6$ is selected from the group consisting of —($SO_2$)— $C_{1-6}$ alkyl, —(PO)($C_{1-6}$ alkyl)$_2$, or —(CO)—NH—$C_{1-6}$ alkyl; further preferably, $R_6$ is selected from the group consisting of

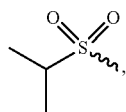

dimethylphosphinoyl, or methylaminoacyl.

In another preferred embodiments, $R_2$ is selected from the group consisting of halogen or $C_{1-6}$ alkyl, more preferably is fluorine, chlorine, bromine or methyl, most preferably is chlorine.

In other preferred embodiments, $R_3$ is $C_{1-6}$ alkoxy, more preferably is methoxy.

In further preferred embodiments, $R_4$ is —NH—(CO)—$C_{2-6}$ alkenyl, and more preferably is

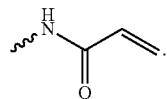

In another preferred embodiments, $R_5$ is

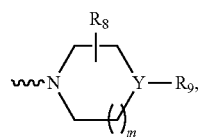

wherein Y is selected from the group consisting of CH or N, m=1 or 2; and wherein Y is more preferably N. Wherein, $R_8$ is selected from the group consisting of H or $C_{1-6}$ alkyl, and more preferably is H or methyl, especially preferably is H. Wherein, $R_9$ is selected from the group consisting of H, $C_{1-6}$ alkyl (e.g., methyl, ethyl, or isopropyl), $C_{1-6}$ alkoxy $C_{1-6}$ alkyl (e.g., methoxyethyl), $C_{3-8}$ cycloalkyl (e.g., cyclohexyl), heterocyclyl (e.g., N-morpholinyl), or $C_{1-6}$ alkylsulfonyl (e.g., methylsulfonyl), and $R_9$ is more preferably H or $C_{1-6}$ alkyl, and $R_9$ is especially preferably methyl, ethyl or isopropyl.

The present disclosure relates to chiral compounds which may have any configuration or may be a mixed racemate.

The present disclosure also relates to a pharmaceutical composition comprising the above compound, and a method and use of the compound for preventing or treating diseases, disorders or conditions regulated by tyrosine kinase activity or affected by tyrosine kinase activity or involving tyrosine kinase activity.

DESCRIPTION OF THE FIGURES

FIGS. 4a-4d illustrate the effect of Compound 1 on tumors of non-small cell lung cancer cell PC-9;

FIGS. 5a-5d illustrate the effect of Compound 1 on tumors of non-small cell lung cancer cell H1975;

FIGS. 6a-6d illustrate the effect of Compound 1 on tumors of non-small cell lung cancer cell H3122;

FIGS. 7a-7d illustrate the effect of Compound 10 on tumors of non-small cell lung cancer cell H3122.

DETAILED DESCRIPTION OF THE INVENTION

Terminology

Figure 1A:
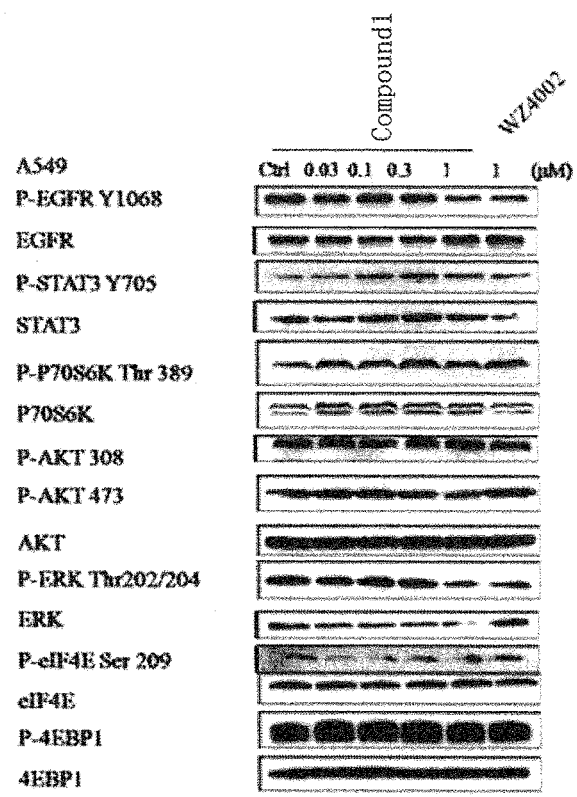
FIGS. 1a-1e illustrate the effect of Compound 1 on cell signaling pathways in cell lines A549, H1975, H3255, PC-9 and H3122.
Figure 1B:
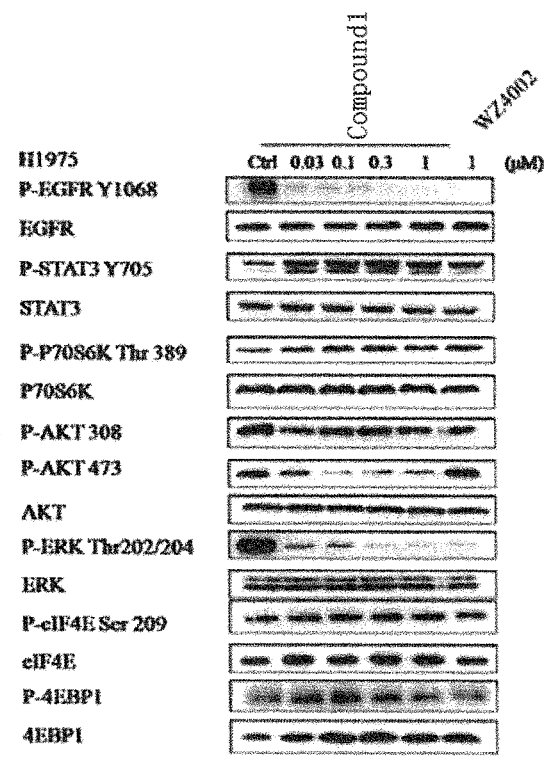
Figure 1C:
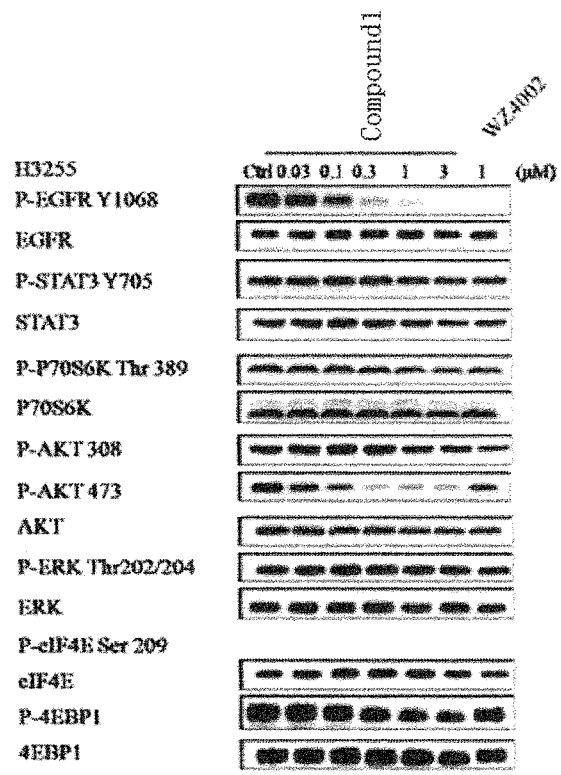
Figure 1D:
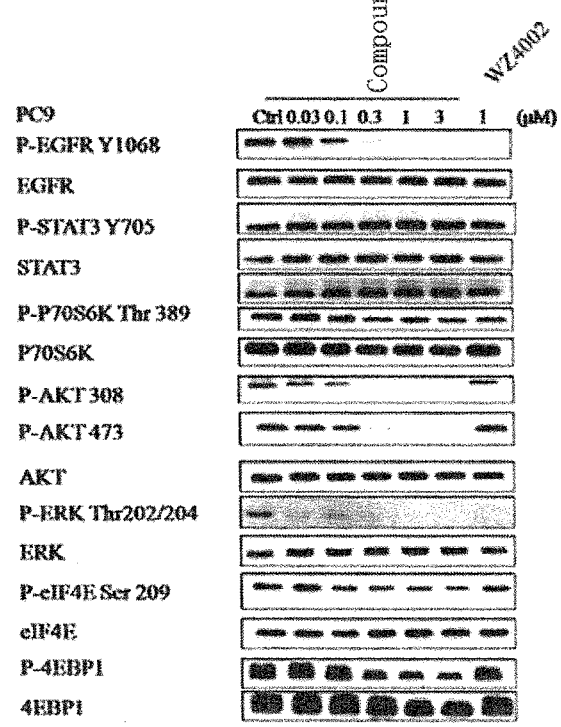

Unless defined otherwise, all technical and scientific terms used herein have the same meaning as is commonly understood by one of skill in the art to which the claimed subject matter belongs.

Unless otherwise indicated, conventional methods of mass spectroscopy, NMR, HPLC, protein chemistry, biochemistry, recombinant DNA techniques and pharmacology, within the skill of the art are employed in the present disclosure. Unless specific definitions are provided, the nomenclature employed in connection with, and the laboratory procedures and techniques of, analytical chemistry, synthetic organic chemistry, and medicinal and pharmaceutical chemistry described herein are those known in the art. The foregoing techniques and procedures can be generally performed of conventional methods well known in the art and as described in various general and more specific references that are cited and discussed throughout the present specification.

The term "alkyl" refers to an aliphatic hydrocarbon group, which may have branched or straight chain. Depending on the structure, an alkyl group can be a monoradical or a diradical (i.e., an alkylene group). In the invention, the alkyl group is preferable a "lower alkyl" having 1 to 8 carbon atoms. Typical alkyl groups include, but are not limited to, methyl, ethyl, propyl, isopropyl, butyl, isobutyl, tertiary butyl, pentyl, hexyl, and the like.

"Alkoxy" refers to an —O-alkyl group, where alkyl is as defined herein. Typical alkoxy groups include, but are not limited to, methoxy, ethoxy, propoxy, butoxy, pentyloxy, hexyloxy, and the like.

The term "amino" refers to an —$NH_2$ group. The term "aminoacyl" refers to —CO—$NH_2$. The term "amide" or "amido" refers to —NR—CO—R', wherein R and R' are independently hydrogen or alkyl.

The term "alkylamino" refers to an amino substituent which is further substituted with one or two alkyl groups, specifically refers to the group —NRR', wherein R and R' are each independently selected from the group consisting of hydrogen or lower alkyl, with the proviso that —NRR' is not —$NH_2$. The term "aralkylamino" as used herein refers to the group —NRR', wherein R is lower aralkyl, and R' is hydrogen, lower alkyl, aryl or lower aralkyl. The term "aminoalkyl" refers to an alkyl substituent which is further substituted with one or more amino groups. The term "hydroxyalkyl" or "hydroxylalkyl" refers to an alkyl substituent which is further substituted with one or more hydroxyl groups. The term "cyanoalkyl" refers to an alkyl substituent which is further substituted with one or more cyano groups. The term "alkylcarbonyl" refers to a carbonyl group which is further substituted with one alkyl group. The term "alkylcarbonylalkyl" refers to an alkyl group which is further substituted with one alkylcarbonyl group. The term "alkoxycarbonyl" refers to a carbonyl group which is further substituted with one alkoxy group. The alkyl or aryl portion of alkylamino, aminoalkyl, hydroxyalkyl, cyanoalkyl, alkylcarbonyl, alkylcarbonylalkyl, and alkoxycarbonyl may be optionally substituted with one or more substituents. The term "alkylsulfonyl" refers to —S($=$O)$_2$—R, wherein R is alkyl.

The term "carbonyl" is an organic functional group (C$=$O) formed by carbon atom and oxygen atom through a double bond linkage. The term "alkanoyl" or "alkylcarbonyl" refers to a carbonyl group which is further substituted with one alkyl group. Typical alkanoyl groups include but not limited to ethanoyl, propionyl, butyryl, pentanoyl, hexanoyl, etc.

The term "aromatic" refers to a planar ring having a delocalized π-electron system containing 4n+2 π electrons, where n is an integer. Aromatic rings can be formed from five, six, seven, eight, nine, or more than nine atoms. Aromatics can be optionally substituted. The term "aromatic" includes both carbocyclic aryl (e.g., phenyl) and heterocyclic aryl (or "heteroaryl" or "heteroaromatic") groups (e.g., pyridine). The term includes monocyclic or fused-ring polycyclic (i.e., rings which share adjacent pairs of carbon atoms) groups.

As used herein, the term "aryl" refers to an aromatic ring wherein each of the atoms forming the ring is a carbon atom. Aryl rings can be formed from five, six, seven, eight, nine, or more than nine carbon atoms. Aryl groups can be optionally substituted. Examples of aryl groups include, but are not limited to phenyl, naphthalenyl, phenanthrenyl, anthracenyl, fluorenyl, and indenyl. Depending on the structure, an aryl group can be a monoradical or a diradical (i.e., an arylene group).

As used herein, the term "heteroalkyl" refers to an alkyl radical, as defined herein, in which one or more skeletal chain atoms is a heteroatom, e.g., oxygen, nitrogen, sulfur, silicon, phosphorus or combinations thereof. The heteroatom(s) may be placed at any interior position of the heteroalkyl group or at the position at which the heteroalkyl group is attached to the remainder of the molecule.

The term "heteroaryl" refers to an aryl group that includes one or more ring heteroatoms selected from nitrogen, oxygen and sulfur. An N-containing "heteroaryl" moiety refers to an aromatic group in which at least one of the skeletal atoms of the ring is a nitrogen atom. Depending on the structure, the heteroaryl group may be a monoradical or a diradical (i.e., a heteroarylene group). Examples of heteroaryl groups include, but are not limited to pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, indazolyl, indolizinyl, phthalazinyl, pyridazinyl, isoindolyl, pteridinyl, purinyl, oxadiazolyl, thiadiazolyl, furyl, benzofuranyl, benzothiophenyl, benzothiazolyl, benzoxazolyl, quinazolinyl, naphthyridinyl, furopyridinyl, and the like.

As used herein, the term "heterocycloalkyl" refers to a non-aromatic ring wherein one or more atoms forming the ring is a heteroatom selected from nitrogen, oxygen and sulfur. Heterocycloalkyl rings can be formed by three, four, five, six, seven, eight, nine, or more than nine atoms. Heterocycloalkyl rings can be optionally substituted. Examples of heterocycloalkyls include, but are not limited to, lactams, lactones, cyclic imides, cyclic thioimides, cyclic carbamates, tetrahydrothiopyran, 4H-pyran, tetrahydropyran, piperidine, 1,3-dioxin, 1,3-dioxane, 1,4-dioxin, 1,4-dioxane, piperazine, 1,3-oxathiane, 1,4-oxathiin, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, morpholine, trioxane, hexahydro-1,3,5-triazine, tetrahydrothiophene, tetrahydrofuran, pyrroline, pyrrolidine, imidazolidine, pyrrolidone, pyrazoline, pyrazolidine, imidazoline, imidazolidine, 1,3-dioxole, 1,3-dioxolane, 1,3-dithiole, 1,3-dithiolane, isoxazoline, isoxazolidine, oxazoline, oxazolidine, oxazolidinone, thiazoline, thiazolidine, and 1,3-oxathiolane. Depending on the structure, a heterocycloalkyl group can be a monoradical or a diradical (i.e., a heterocycloalkylene group).

The term "alkyl(heteroaryl)" means an alkyl radical, as defined herein, substituted with a heteroaryl group, as defined herein.

The term "alkyl(heterocycloalkyl)" means an alkyl radical, as defined herein, substituted with a heterocycloalkyl group, as defined herein.

The term "halo" or "halogen" means fluoro, chloro, bromo and iodo.

The terms "haloalkyl", "haloalkoxy" and "haloheteroalkyl" include alkyl, alkoxy and heteroalkyl structures in which at least one hydrogen is replaced with a halogen atom. In certain embodiments in which two or more hydrogen atoms are replaced with halogen atoms, the halogen atoms are the same or different as one another.

As used herein, the term "cyano" refers to —CN group.

The term "ester" refers to a chemical moiety with formula —COOR, where R is selected from alkyl, cycloalkyl, aryl, heteroaryl (bonded through a ring carbon) and heteroalicyclic (bonded through a ring carbon).

The term "optionally substituted" or "substituted" means that the referenced group may be substituted with one or more additional group(s) which are each independently selected from alkyl, cycloalkyl, aryl, heteroaryl, hydroxy, alkoxy, cyano, halo, amide, nitro, haloalkyl, amino, and the like.

The terms "inhibits", "inhibiting", or "inhibitor" of a kinase, as used herein, refer to inhibition of phosphotransferase activity.

A "metabolite" of a compound disclosed herein is a derivative of that compound that is formed when the compound is metabolized. The term "active metabolite" refers to a biologically active derivative of a compound that is formed when the compound is metabolized. The term "metabolized" as used herein, refers to the sum of the processes (including, but not limited to, hydrolysis reactions and reactions catalyzed by enzymes, such as, oxidation reactions) by which a particular substance is changed by an organism. Thus, enzymes may cause specific structural alterations. For example, cytochrome P450 catalyzes a variety of oxidation and reduction reactions while uridine diphosphate glucuronyl transferases catalyze the transfer of an activated glucuronic acid molecule to aromatic alcohol, aliphatic alcohol, carboxylic acid, amine and free sulfhydryl group. Further information on metabolism may be obtained from *The Pharmacological Basis of Therapeutics,* 9th Edition, McGraw-Hill (1996). Metabolites of the compounds disclosed herein can be identified either by administration of compounds to a host and analysis of tissue samples from the host, or by incubation of compounds with hepatic cells in vitro and analysis of the resulting compounds. Both methods are well known in the art. In some embodiments, metabolites of a compound are formed by oxidation processes and correspond to the corresponding hydroxy-containing compound. In some embodiments, a compound is metabolized to pharmacologically active metabolites. The term "modulate" as used herein, means to interact with a target either directly or indirectly so as to alter the activity of the target, including, by way of example only, to enhance the activity of the target, to inhibit the activity of the target, to limit the activity of the target, or to extend the activity of the target.

As used herein, the term "target protein" refers to a protein molecule or a portion of a protein capable of being bound by a selective binding compound. In certain embodiments, the target protein is tyrosine kinase EGFR (wild-type or various mutants or the combination thereof), ALK (wild-type or various mutants or the combination thereof), KIT (wild-type or various mutants or the combination thereof), ABL (wild-type or various mutants or the combination thereof), FLT3 (wild-type or various mutants or the combination thereof), BLK (wild-type or various mutants or the combination thereof), VEGFR (wild-type or various mutants or the combination thereof), RET (wild-type or various mutants or the combination thereof), PDGFR (wild-type or various mutants or the combination thereof), MEK (wild-type or various mutants or the combination thereof), BCR/ABL (wild-type or various mutants or the combination thereof), JAK (wild-type or various mutants or the combination thereof), BRAF (wild-type or various mutants or the combination thereof).

As used herein, $GI_{50}$ refers to a drug concentration required for 50% growth inhibition of cells, i.e., a drug concentration at which the growth of 50% cancer cells can be inhibited or controlled by the drug.

As used herein, $IC_{50}$ refers to an amount, concentration or dosage of a particular test compound that achieves a 50% inhibition of a maximal response, in an assay that measures such response.

As used herein, $EC_{50}$ refers to a dosage, concentration or amount of a test compound that elicits a dose-dependent response at 50% of maximal expression of a particular response that is induced, provoked or potentiated by the particular test compound.

The Novel Kinase Inhibitor of the Present Disclosure

The present disclosure provides a novel kinase inhibitor, comprising a compound of formula (I), or a pharmaceutically acceptable salt, solvate, ester, acid, metabolite or prodrug thereof:

Formula I

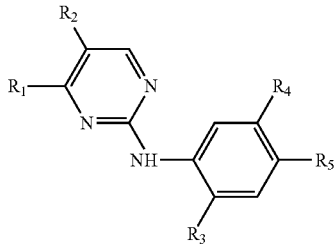

wherein:

$R_1$ is selected from the group consisting of H,

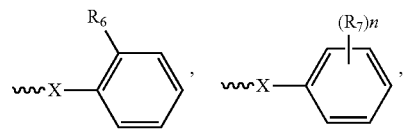

—X—$C_{3-6}$ cycloalkyl, or —X—$C_{1-6}$ alkylene-heteroaryl, wherein X is selected from the group consisting of —O—, —NH— or —N($C_{1-6}$ alkyl)-, n=1, 2 or 3;

$R_2$ is selected from the group consisting of halogen, $C_{1-6}$ alkyl, $C_{1-6}$ haloalkyl, $C_{1-6}$ alkoxy, nitro, amino, cyano or hydroxy;

$R_3$ is selected from the group consisting of H, $C_{1-6}$ alkoxy, $C_{1-6}$ haloalkoxy, or $C_{1-6}$ thioalkoxy;

$R_4$ is selected from the group consisting of —NH—(CO)—$C_{1-6}$ alkyl (e.g.,

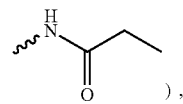), or —NH—(CO)—$C_{2-6}$ alkenyl (e.g.,

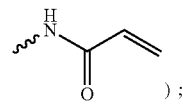);

$R_5$ is selected from the group consisting of

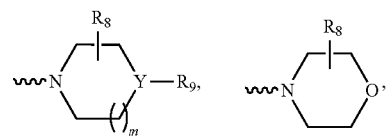

heteroaryl (e.g.,

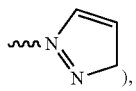),

—O-heteroaryl (e.g.,

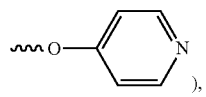),

—O—$C_{1-6}$ alkylene-$C_{1-6}$ alkylamino (e.g.,

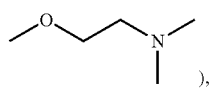),

—O—$C_{1-6}$ alkylene-heterocyclyl (e.g.,

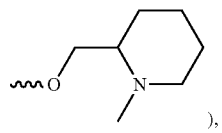), or $C_{1-6}$ alkylamino substituted with $C_{1-6}$ alkylamino (e.g., (2-(dimethylamino)ethyl)(methyl)amino), wherein Y is selected from the group consisting of CH or N, m=1 or 2;

$R_6$ is selected from the group consisting of H, cyano, —(SO$_2$)—$C_{1-6}$ alkyl (e.g.,

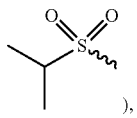),

—(SO$_2$)—$C_{1-6}$ alkylamino (e.g.,

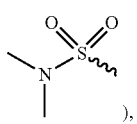),

—(PO)($C_{1-6}$ alkyl)$_2$ (e.g., dimethylphosphinoyl), —(CO)—NH—$C_{1-6}$ alkyl (e.g., methylaminoacyl), or heteroarylalkoxy in which the heteroatom is optionally substituted with $C_{1-6}$ alkyl (e.g., (1-methyl-1H-imidazol-2-yl)methoxy);

$R_7$ are each independently selected from the group consisting of H, halogen, $C_{1-6}$ alkyl, $C_{1-6}$ haloalkyl, $C_{1-6}$ alkoxy, nitro, amino, cyano, hydroxy, or —NH-(amino-protecting group);

$R_8$ is selected from the group consisting of H, $C_{1-6}$ alkyl, halogen, $C_{1-6}$ haloalkyl, $C_{1-6}$ alkoxy, nitro, amino, cyano or hydroxy;

$R_9$ is selected from the group consisting of H, $C_{1-6}$ alkyl (e.g., methyl, ethyl, or isopropyl), $C_{1-6}$ haloalkyl (e.g., fluoroethyl), amino-protecting group, $C_{1-6}$ alkoxy $C_{1-6}$ alkyl (e.g., methoxyethyl), $C_{3-8}$ cycloalkyl (e.g., cyclohexyl), $C_{1-6}$ alkylamino (e.g., dimethylamino), $C_{4-8}$ cycloalkylalkyl (e.g., cyclopropylmethyl), aryl $C_{1-6}$ alkyl (e.g., benzyl), heterocyclyl in which the heteroatom is optionally substituted with $C_{1-6}$ alkyl or $C_{1-6}$ alkylsulfonyl (e.g., piperidin-1-yl, N-morpholinyl, 1-methylpiperazin-4-yl, 1-methylpiperidine-4-yl, (1-methylsulfonyl)piperidin-4-yl, or 4-(methylsulfonyl)piperazin-1-ye, $C_{1-6}$ alkylsulfonyl (e.g., methylsulfonyl), or $C_{2-6}$ alkanoyl (e.g., ethanoyl);

the amino-protecting groups are each independently selected from the group consisting of pivaloyl (Piv), tert-butyloxycarbonyl (Boc), benzyloxycarbonyl (Cbz), 9-fluorenylmethyloxycarbonyl (FMOC), benzyl (Bn) and p-methoxyphenyl (PMP).

In preferred embodiments, $R_1$ is

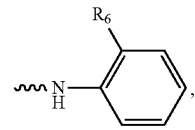

and $R_6$ is selected from the group consisting of —(SO$_2$)—$C_{1-6}$ alkyl, —(PO)($C_{1-6}$ alkyl)$_2$, or —(CO)—NH—$C_{1-6}$ alkyl; further preferably, $R_6$ is selected from the group consisting of

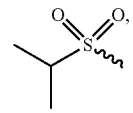

dimethylphosphinoyl, or methylaminoacyl.

In another preferred embodiments, $R_2$ is selected from the group consisting of halogen or $C_{1-6}$ alkyl, more preferably is fluorine, chlorine, bromine or methyl, most preferably is chlorine.

In other preferred embodiments, $R_3$ is $C_{1-6}$ alkoxy, more preferably is methoxy.

In further preferred embodiments, $R_4$ is —NH—(CO)—$C_{2-6}$ alkenyl, and more preferably is

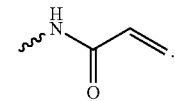

In another preferred embodiments, $R_5$ is

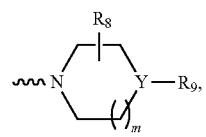

wherein Y is selected from the group consisting of CH or N, m=1 or 2; and wherein Y is more preferably N. Wherein, $R_8$ is selected from the group consisting of H or $C_{1-6}$ alkyl, and more preferably is H or methyl, and especially preferably is H. Wherein, $R_9$ is selected from the group consisting of H, $C_{1-6}$ alkyl (e.g., methyl, ethyl, or isopropyl), $C_{1-6}$ alkoxy $C_{1-6}$ alkyl (e.g., methoxyethyl), $C_{3-8}$ cycloalkyl (e.g., cyclohexyl), heterocyclyl (e.g., N-morpholinyl), or $C_{1-6}$ alkylsulfonyl (e.g., methylsulfonyl), and $R_9$ is more preferably H or $C_{1-6}$ alkyl, and $R_9$ is especially preferably methyl, ethyl or isopropyl.

Described herein is a novel kinase inhibitor. The pharmaceutically acceptable salts, solvates, esters, acids, pharmaceutically active metabolites and prodrugs of these compounds are also described herein.

In additional or further embodiments, the compounds described herein are metabolized upon administration to an organism in need thereof to produce a metabolite that is then used to produce a desired effect, including a desired therapeutic effect.

Compounds described herein may be formed as, and/or used as, pharmaceutically acceptable salts. The type of pharmaceutical acceptable salts, include, but are not limited to: (1) acid addition salts, formed by reacting the free base form of the compound with a pharmaceutically acceptable inorganic acid such as hydrochloric acid, hydrobromic acid, sulfuric acid, nitric acid, phosphoric acid, metaphosphoric acid, and the like; or with an organic acid such as acetic acid, propionic acid, hexanoic acid, cyclopentanepropionic acid, glycolic acid, pyruvic acid, lactic acid, malonic acid, malic acid, citric acid, succinic acid, maleic acid, tartaric acid, fumaric acid, trifluoroacetic acid, benzoic acid, 3-(4-hydroxybenzoyl) benzoic acid, cinnamic acid, mandelic acid, methanesulfonic acid, ethanesulfonic acid, 1,2-ethanedisulfonic acid, 2-hydroxyethanesulfonic acid, benzenesulfonic acid, toluenesulfonic acid, 4-methylbicyclo-[2.2.2] oct-2-ene-1-carboxylic acid, 2-naphthalenesulfonic acid, tertiary butylacetic acid, glucoheptonic acid, 4,4'-methylenebis-(3-hydroxy-2-ene-1-carboxylic acid), 3-phenylpropionic acid, trimethylacetic acid, lauryl sulfuric acid, gluconic acid, glutamic acid, salicylic acid, hydroxynaphthoic acid, stearic acid, muconic acid, and the like; (2) base addition salts formed when an acidic proton present in the parent compound either is replaced by a metal ion, e.g., an alkali metal ion (e.g. lithium, sodium, potassium), an alkaline earth metal ion (e.g. magnesium, or calcium), or an aluminum ion; or coordinates with an organic base. Acceptable organic bases include ethanolamine, diethanolamine, triethanolamine, trimethylamine, N-methylglucamine, and the like. Acceptable inorganic bases include aluminum hydroxide, calcium hydroxide, potassium hydroxide, sodium carbonate, sodium hydroxide, and the like.

The corresponding counterions of the pharmaceutically acceptable salts may be analyzed and identified using various methods including, but not limited to, ion exchange chromatography, ion chromatography, capillary electrophoresis, inductively coupled plasma, atomic absorption spectroscopy, mass spectrometry, or any combination thereof.

The salts are recovered by using at least one of the following techniques: filtration, precipitation with a nonsolvent followed by filtration, evaporation of the solvent, or, in the case of aqueous solutions, lyophilization.

The screening and characterization of the pharmaceutically acceptable salts, polymorphs and/or solvates may be accomplished using a variety of techniques including, but not limited to, thermal analysis, x-ray diffraction, spectroscopy, microscopy and element analysis. The various spectroscopic techniques used include, but are not limited to, Raman, FTIR, UVIS, and NMR (liquid and solid state). The various microscopy techniques include, but are not limited to, IR microscopy and Raman microscopy.

The Pharmaceutical Composition of the Present Disclosure

The present disclosure also provides a pharmaceutical composition comprising at least one compound of formula (I), or a pharmaceutically acceptable salt, solvate, ester, acid, pharmaceutically active metabolite or prodrug of the compound, and a pharmaceutically acceptable carrier or excipient, and optionally other therapeutic agents.

During treatment, it may be used alone or in combination with one or more other therapeutic agents depending on the situation. The drug containing the compound of the present disclosure may be administered to the patients through at least one of injection, oral administration, inhalation, rectal and transdermal administration.

In the embodiments of the present disclosure, when a patient is treated in accordance with the present disclosure, the amount of a given agent will vary depending upon factors such as the particular dosing regimen, the type of the disease or condition and its severity, the characteristics (e.g., weight) of the subject or host in need of treatment, but can be routinely determined in a manner known in the art according to the particular circumstances surrounding the case, including, e.g., the specific agent being administered, the route of administration, the condition being treated, and the subject or host being treated. In general, doses employed for adult human treatment will typically be in the range of 0.02-5000 mg per day, such as about 1-1500 mg per day. The desired dose may be conveniently presented in a single dose or as divided doses administered simultaneously (or over a short period of time) or at appropriate intervals, for example as two, three, four or more sub-doses per day. It will be appreciated by those skilled in the art that, although the above dosage ranges are given, the specific effective amounts may be appropriately adjusted depending on the condition of the patient and the judgment of the practitioner.

Use of the Compound of the Present Disclosure

The compound of formula (I), or a pharmaceutically acceptable salt, solvate, ester, acid, metabolite or prodrug thereof, or the pharmaceutical composition can be used to inhibit the activity of tyrosine kinase EGFR (wild-type or various mutants or the combination thereof), ALK (wild-type or various mutants or the combination thereof), KIT (wild-type or various mutants or the combination thereof), ABL (wild-type or various mutants or the combination thereof), FLT3 (wild-type or various mutants or the combination thereof), BLK (wild-type or various mutants or the combination thereof), VEGFR (wild-type or various mutants or the combination thereof), RET (wild-type or various mutants or the combination thereof), PDGFR (wild-type or various mutants or the combination thereof), MEK (wild-type or various mutants or the combination thereof), BCR/ABL (wild-type or various mutants or the combination thereof), JAK (wild-type or various mutants or the combination thereof), BRAF (wild-type or various mutants or the combination thereof). The compound of formula (I), or a pharmaceutically acceptable salt, solvate, ester, acid, metabolite or prodrug thereof can be used to or formulated to treat one or more diseases selected from the group consisting of non-small cell lung cancer, small cell lung cancer, lung adenocarcinoma, lung squamous carcinoma, pancreatic cancer, prostate cancer, bladder cancer, liver cancer, skin cancer, glioma, breast cancer, melanoma, glioblastoma, rhabdomyosarcoma, ovarian cancer, astrocytoma, Ewing's sarcoma, retinoblastoma, epithelial cell carcinoma, colon cancer, kidney cancer, gastrointestinal stromal tumor, leukemia, histiocytic lymphoma, and nasopharyngeal carcinoma.

More preferably, the compound of formula (I), a pharmaceutically acceptable salt, solvate, ester, acid, metabolite or prodrug thereof, or the pharmaceutical composition described herein, is a dual inhibitor of mutant EGFR and ALK, which can be used alone or in combination with other therapeutic agents for the treatment of diseases, in particular non-small cell lung cancer. In particular, the compound of the present disclosure can be used to treat diseases (e.g., non-small cell lung cancer) carrying EGFR wild-type gene, or carrying EGFR T790M mutant gene and/or EGFR L858R mutant gene and/or EGFR delE746_A750 mutant gene, or to treat diseases (e.g., non-small cell lung cancer) carrying ALK wild-type gene, or carrying ALK F1174L mutant gene and/or ALK F1196M mutant gene and/or EML4-ALK mutant gene and/or NPM-ALK mutant gene, and can be used for first-line treatment of advanced anaplastic lymphoma kinase (ALK)-positive non-small cell lung cancer.

Preparation of the Compound

Compounds of formula (I) may be synthesized using standard synthetic techniques known to those of skill in the art or using methods known in the art in combination with methods described herein. In additions, solvents, temperatures and other reaction conditions presented herein may vary according to those of skill in the art. As a further guide the following synthetic methods may also be utilized.

The reactions can be employed in a linear sequence to provide the compounds described herein or they may be used to synthesize fragments which are subsequently joined by the methods described herein and/or known in the art.

In certain embodiments, provided herein are methods of making and methods of using tyrosine kinase inhibitor compounds described herein. In certain embodiments, compounds described herein can be synthesized using the following synthetic schemes. Compounds may be synthesized using methodologies analogous to those described below by the use of appropriate alternative starting materials.

The starring materials used for the synthesis of the compounds described herein may be synthesized or can be obtained from commercial sources. The compounds described herein, and other related compounds having different substituents can be synthesized using techniques and materials known to those of skill in the art. General methods for the preparation of compounds as disclosed herein may be derived from known reactions in the field, and the reactions may be modified by the use of appropriate reagents and conditions, as would be recognized by the skilled person, for the introduction of the various moieties into the molecules as provided herein.

The products of the reactions may be isolated and purified, if desired, using conventional techniques, including, but not limited to, filtration, distillation, crystallization, chromatography and the like. Such products may be characterized using conventional means, including physical constants and spectral data.

A non-limiting example of a synthetic approach towards the preparation of compounds of formula (I) is shown in Scheme I.

Using the synthetic methods described herein, as well as those known in the art, tyrosine kinase inhibitors as disclosed herein are obtained in good yields and purity. The compounds prepared by the methods disclosed herein are purified by conventional means known in the art, such as, filtration, recrystallization, chromatography, distillation, and combinations thereof.

Sites on the aromatic ring portion of compounds of formula (I) can be susceptible to various metabolic reactions, therefore incorporation of appropriate substituents on the aromatic ring structures, such as, by way of example only, halogens can reduce, minimize or eliminate this metabolic pathway.

EXAMPLES

The following specific and non-limiting examples are to be construed as merely illustrative, and do not limit the present disclosure in any way whatsoever. Without further elaboration, it is believed that one skilled in the art can, based on the description herein, utilize the present disclosure to its fullest extent.

Synthesis of the Compounds of the Present Disclosure

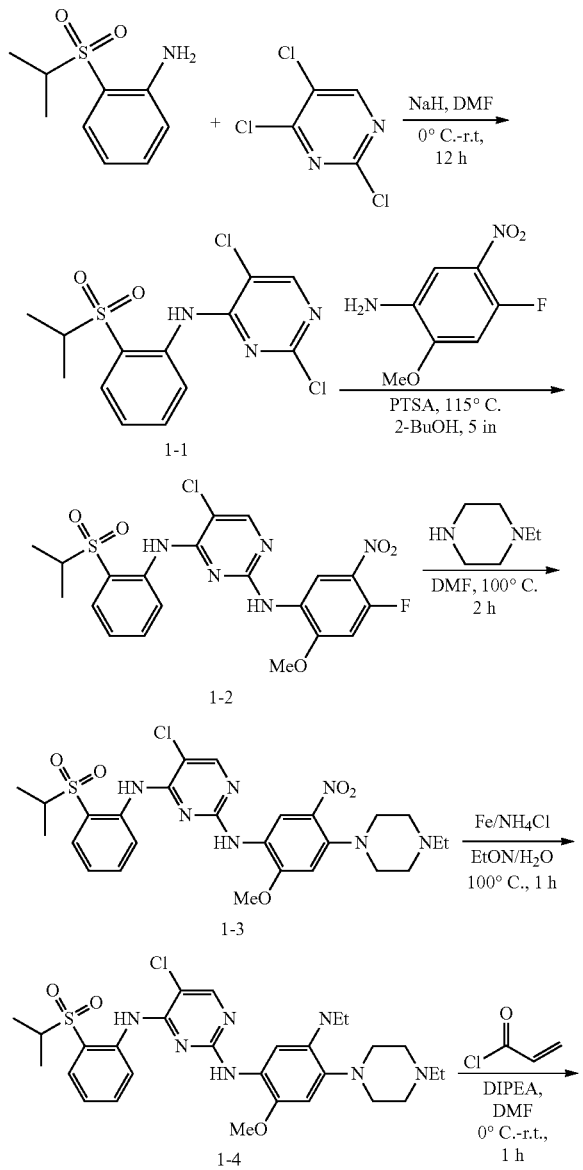

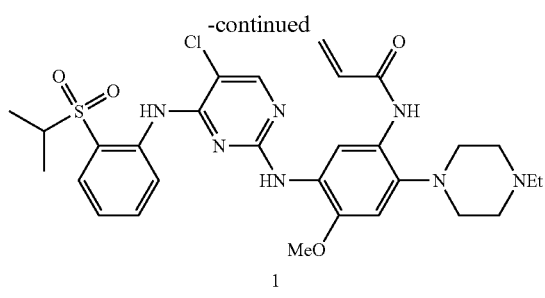

1

Step 1: Preparation of 2,5-dichloro-N-(2-(isopropyl-sulfonyl) phenyl)pyrimidine-4-amine Intermediate 1-1

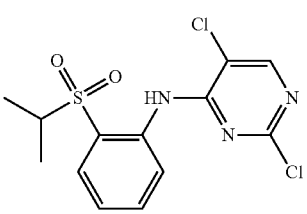 [SMILES: CC(C)S(=O)(=O)c1ccccc1Nc1nc(Cl)ncc1Cl]

2-(isopropylsulfonyl)phenylamine (9.96 g, 50 mmol) was weighed and dissolved in N,N-dimethylformamide (DMF, 100 mL), to which sodium hydride (NaH, 2.4 g, 100 mmol) was slowly added on an ice bath and stirred for 0.5 h. A solution of 2,4,5-trichloropyrimidine (11.0 g, 60 mmol) dissolved in 20 mL of DMF was slowly added dropwise on an ice bath. After the addition, the mixture was reacted overnight at room temperature, washed with water, and extracted with ethyl acetate. After drying and concentration, the crude material was purified by column chromatography to give a white solid 1-1 (6.9 g, 40%). MS(ESI): m/z 346.0 (M+H)+. $^1$H NMR (400 MHz, CDCl3) δ 10.07 (s, 1H), 8.63 (d, J=8.0 Hz, 1H), 8.30 (s, 1H), 7.92 (d, J=7.4 Hz, 1H), 7.73 (t, J=7.4 Hz, 1H), 7.33 (t, J=7.0 Hz, 1H), 3.22 (heptet, J=6.0 Hz, 1H), 1.32 (d, J=6.0 Hz, 6H). $^{13}$C NMR (100 MHz, CDCl3) δ 157.8, 156.3, 155.6, 137.3, 135.2, 131.4, 124.5, 124.2, 122.7, 115.2, 56.1, 15.3.

Step 2: Preparation of 5-chloro-N$^2$-(4-fluoro-2-methoxy-5-nitrophenyl)-N$^4$-(2-(isopropylsulfonyl) phenyl)pyrimidine-2,4-diamine Intermediate 1-2

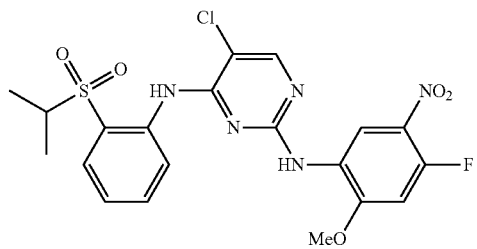 [SMILES: COc1cc(F)c([N+](=O)[O-])cc1Nc1ncc(Cl)c(Nc2ccccc2S(=O)(=O)C(C)C)n1]

The intermediate 1-1 (138 mg, 0.4 mmol), 4-fluoro-2-methoxy-5-nitrophenylamine (74.4 mg, 0.3 mmol), and p-methylbenzenesulfonic acid (PTSA, 68.8 mg, 0.3 mmol) were dissolved in 4 mL of sec-butanol, and reacted for 5 hours at 115° C. The resulting product was concentrated and purified by column chromatography to give a solid 1-2 (100.9 mg, 51%). MS(ESI): m/z 496.1 (M+H)+. $^1$H NMR (400 MHz, CDCl3) δ 9.80 (s, 1H), 8.46-8.44 (m, 1H), 8.41 (s, 1H), 8.30 (br, 1H), 7.85 (d, J=7.0 Hz, 1H), 7.62-7.35 (m, 3H), 7.14 (s, 1H), 3.95 (s, 3H), 3.46 (heptet, J=6.0 Hz, 1H), 1.32 (d, J=6.0 Hz, 6H).

Step 3: Preparation of 5-chloro-N$^2$-(4-(4-ethylpiper-azin-1-yl)-2-methoxy-5-nitrophenyl)-N$^4$-(2-(isopropylsulfonyl)phenyl)pyrimidine-2,4-diamine Intermediate 1-3

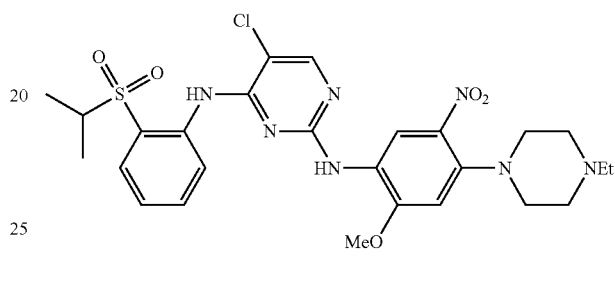

The intermediate 1-2 (99 mg, 0.2 mmol), N-ethyl piperazine (45.6 mg, 0.4 mmol), and potassium carbonate (55.2 mg, 0.4 mmol) were dissolved in 2 ml of DMF and reacted for 2 hours at 100° C. The resulting product was washed with water, extracted with ethyl acetate, dried and purified by column chromatography to give the target solid 1-3 (94.2 mg, 80%). MS(ESI): m/z 590.2 (M+H)+.

Step 4: Preparation of N$^2$-(5-amino-4-(4-ethylpiper-azin-1-yl)-2-methoxyphenyl)-5-chloro-N$^4$-(2-(isopropylsulfonyl)phenyl)pyrimidine-2,4-diamine Intermediate 1-4

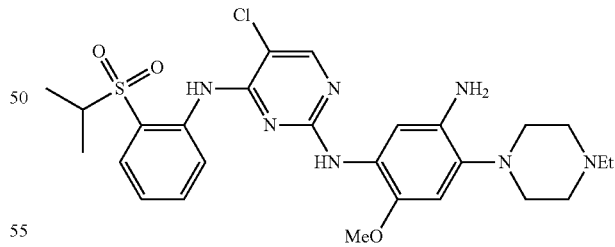

The intermediate 1-3 (94.2 mg, 0.16 mmol), reductive iron powder (Fe, 89.6 mg, 1.6 mmol), and ammonium chloride (53.4 mg, 0.96 mmol) were dissolved in 6 ml of ethanol and 2 ml of water and reacted at 100° C. for 1 hour. The resulting product was concentrated and purified by column chromatography to give a solid 1-4 (37.6 mg, 0.067 mmol). MS(ESI): m/z 560.3 (M+H)+.

Example 1: Preparation of N-(5-(5-chloro-4-(2-(isopropylsulfonyl)phenylamino)pyrimidin-2-ylamino)-2-(4-ethylpiperazin-1-yl)-4-methoxyphenyl)acrylamide Compound 1

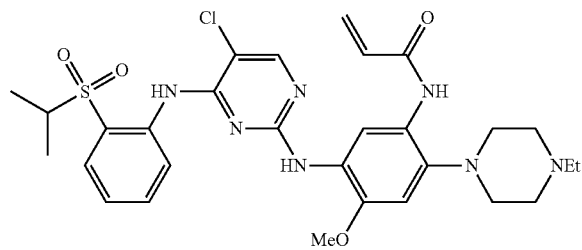

The intermediate 1-4 (37.6 mg, 0.067 mmol), and N,N-diisopropylethylamine (DIPEA, 17.5 mg, 0.13 mmol) were dissolved in 1 mL of DMF and to which acryloyl chloride (9 mg, 0.1 mmol) was added dropwise on an ice bath. The mixture was reacted for half an hour at room temperature, washed with water, extracted, and purified to give Compound 1 (30 mg, 0.049 mmol). MS(ESI): m/z 614.2 (M+H)+. $^1$H NMR (400 MHz, DMSO-d6) δ 9.54 (s, 1H), 9.02 (s, 1H), 8.51 (br, 2H), 8.23 (s, 1H), 8.16 (br, 1H), 7.78 (d, J=7.6 Hz, 1H), 7.56-7.54 (m, 1H), 7.26 (t, J=7.6 Hz, 1H), 6.86 (s, 1H), 6.65-6.63 (m, 1H), 6.16 (d, J=14.6 Hz, 1H), 5.72 (d, J=10.0 Hz, 1H), 3.79 (s, 3H), 3.46 (heptet, J=6.0 Hz, 1H), 3.34 (s, 2H), 3.18-2.60 (m, 8H), 1.24-1.17 (m, 9H).

Example 2: Preparation of N-(5-(5-chloro-4-(2-(isopropylsulfonyl)phenylamino)pyrimidin-2-ylamino)-4-methoxy-2-(4-methylpiperazin-1-yl)phenyl)acrylamide Compound 2

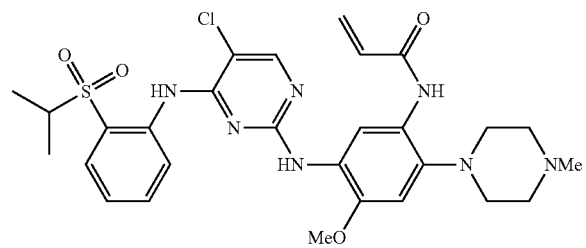 [SMILES: C=CC(=O)Nc1cc(Nc2ncc(Cl)c(Nc3ccccc3S(=O)(=O)C(C)C)n2)c(OC)cc1N1CCN(C)CC1]

Compound 2 (23.5 mg) was obtained by using a process similar as that for preparing Compound 1, except that N-ethyl piperazine was replaced with N-methyl piperazine. MS(ESI): m/z 600.2 (M+H)+. $^1$H NMR (400 MHz, DMSO-d6) δ 9.53 (s, 1H), 8.97 (s, 1H), 8.53-8.47 (m, 2H), 8.23 (s, 1H), 8.11 (s, 1H), 7.77 (d, J=7.6 Hz, 1H), 7.56-7.54 (m, 1H), 7.26 (t, J=7.6 Hz, 1H), 6.86 (s, 1H), 6.63-6.58 (m, 1H), 6.16 (d, J=14.6 Hz, 1H), 5.72 (d, J=10.0 Hz, 1H), 3.79 (s, 3H), 3.46 (heptet, J=6.0 Hz, 1H), 2.90 (s, 3H), 3.18-2.60 (m, 8H), 1.24-1.17 (d, J=6.0 Hz, 6H).

Example 3: Preparation of tert-butyl 4-(2-acrylamido-4-(5-chloro-4-(2-(isopropylsulfonyl)phenylamino)pyrimidin-2-ylamino)-5-methoxyphenyl)piperazine-1-carbonate Compound 3

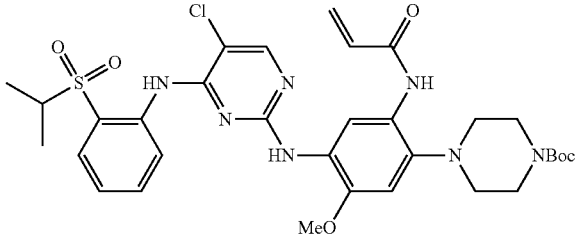

Compound 3 (35.2 mg) was obtained by using a process similar as that for preparing Compound 1, except that N-ethyl piperazine was replaced with N-Boc piperazine. MS(ESI): m/z 686.3 (M+H)+. $^1$H NMR (400 MHz, DMSO-d6) δ 9.52 (s, 1H), 9.03 (s, 1H), 8.50 (br, 2H), 8.22 (s, 1H), 8.19 (s, 1H), 7.76 (d, J=7.6 Hz, 1H), 7.54-7.52 (m, 1H), 7.25 (t, J=7.6 Hz, 1H), 6.89 (s, 1H), 6.64 (dd, J=16.6 Hz, J=10.0 Hz, 1H), 6.15 (d, J=16.6 Hz, 1H), 5.70 (d, J=10.0 Hz, 1H), 3.77 (s, 3H), 3.54 (br, 4H), 3.42 (heptet, J=6.0 Hz, 1H), 2.81 (br, 4H), 1.43 (s, 9H), 1.16 (d, J=6.0 Hz, 6H).

Example 4: Preparation of N-(5-(5-chloro-4-(2-(isopropylsulfonyl) phenylamino)pyrimidin-2-ylamino)-4-methoxy-2-(piperazin-1-yl)phenyl) acrylamide Compound 4

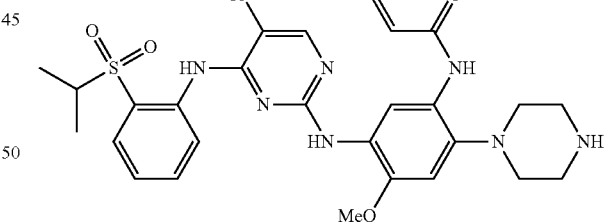

The compound 3 was dissolved in 2 mL of dichloromethane, and 0.5 mL of trifluoroacetic acid was added thereto. The mixture was stirred overnight at room temperature to give Compound 4 (19.8 mg). MS(ESI): m/z 586.2 (M+H)+. $^1$H NMR (400 MHz, DMSO-d6) δ 9.51 (s, 1H), 9.07 (s, 1H), 8.53-8.50 (m, 2H), 8.21 (s, 1H), 8.11 (s, 1H), 7.76 (d, J=7.6 Hz, 1H), 7.52-7.50 (m, 1H), 7.26-7.23 (m, 1H), 6.80 (s, 1H), 6.73-6.66 (m, 1H), 6.15 (d, J=16.2 Hz, 1H), 5.71 (d, J=10.0 Hz, 1H), 3.78 (s, 3H), 3.42 (heptet, J=6.0 Hz, 1H), 3.35 (br, 4H), 3.05 (br, 4H), 1.15 (d, J=6.0 Hz, 6H).

Example 5: Preparation of N-(5-(5-chloro-4-(2-(isopropylsulfonyl)phenylamino)pyrimidin-2-ylamino)-4-methoxy-2-(4-(methylsulfonyl)piperazin-1-yl)phenyl)acrylamide Compound 5

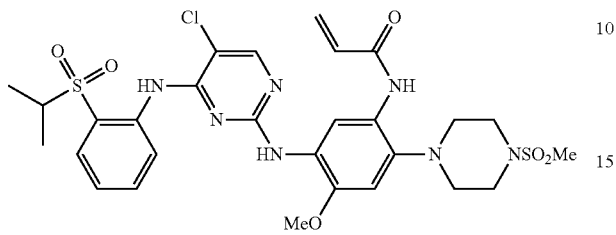

Compound 5 (28.3 mg) was obtained by using a process similar as that for preparing Compound 1, except that N-ethyl piperazine was replaced with N-methylsulfonyl piperazine. MS(ESI): m/z 664.2 (M+H)$^+$. $^1$H NMR (400 MHz, DMSO-d6) δ 9.52 (s, 1H), 9.02 (s, 1H), 8.50 (br, 2H), 8.22 (s, 1H), 8.19 (s, 1H), 7.77 (d, J=8.0 Hz, 1H), 7.54-7.52 (m, 1H), 7.25 (t, J=7.6 Hz, 1H), 6.92 (s, 1H), 6.65 (dd, J=16.8 Hz, J=10.0 Hz, 1H), 6.15 (d, J=16.8 Hz, 1H), 5.72 (d, J=10.0 Hz, 1H), 3.77 (s, 3H), 3.46 (heptet, J=6.0 Hz, 1H), 3.36 (br, 4H), 2.96 (br, 4H), 1.16 (d, J=6.0 Hz, 6H).

Example 6: Preparation of N-(5-(5-chloro-4-(2-(isopropylsulfonyl) phenylamino)pyrimidin-2-ylamino)-4-methoxy-2-(piperidin-1-yl)phenyl) acrylamide Compound 6

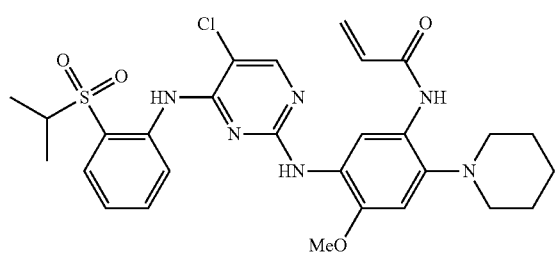

Compound 6 (25.4 mg) was obtained by using a process similar as that for preparing Compound 1, except that N-ethyl piperazine was replaced with piperidine. MS(ESI): m/z 585.2 (M+H)$^+$. $^1$H NMR (400 MHz, DMSO-d6) δ 9.52 (s, 1H), 8.95 (s, 1H), 8.53 (br, 1H), 8.48 (s, 1H), 8.21 (s, 1H), 8.12 (s, 1H), 7.77 (d, J=7.6 Hz, 1H), 7.55-7.51 (m, 1H), 7.25 (t, J=7.6 Hz, 1H), 6.83 (s, 1H), 6.61 (dd, J=16.6 Hz, J=9.8 Hz, 1H), 6.14 (d, J=16.6 Hz, 1H), 5.69 (d, J=9.8 Hz, 1H), 3.76 (s, 3H), 3.42 (heptet, J=6.0 Hz, 1H), 2.80 (br, 4H), 1.72 (br, 4H), 1.55 (br, 2H), 1.16 (d, J=6.0 Hz, 6H).

Example 7: Preparation of N-(5-(5-chloro-4-(2-(isopropylsulfonyl) phenylamino)pyrimidin-2-ylamino)-4-methoxy-2-morpholinylphenyl) acrylamide Compound 7

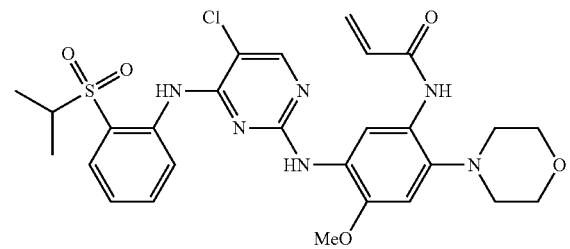

Compound 7 (24.1 mg) was obtained by using a process similar as that for preparing Compound 1, except that N-ethyl piperazine was replaced with morpholine. MS(ESI): m/z 587.3 (M+H)$^+$. $^1$H NMR (400 MHz, DMSO-d6) δ 9.53 (s, 1H), 9.08 (s, 1H), 8.53-8.50 (m, 2H), 8.23 (s, 1H), 8.15 (s, 1H), 7.77 (d, J=8.0 Hz, 1H), 7.55-7.53 (m, 1H), 7.26 (t, J=7.6 Hz, 1H), 6.89 (s, 1H), 6.64 (dd, J=16.8 Hz, J=10.2 Hz, 1H), 6.16 (d, J=16.8 Hz, 1H), 5.71 (d, J=10.2 Hz, 1H), 3.81 (s, 4H), 3.80 (s, 3H), 3.42 (heptet, J=6.0 Hz, 1H), 2.88 (br, 4H), 1.17 (d, J=6.0 Hz, 6H).

Example 8: Preparation of N-(5-(5-chloro-4-(2-(isopropylsulfonyl) phenylamino)pyrimidin-2-ylamino)-4-methoxy-2-(4-(4-methylpiperazin-1-yl) piperidin-1-yl)phenyl)acrylamide Compound 8

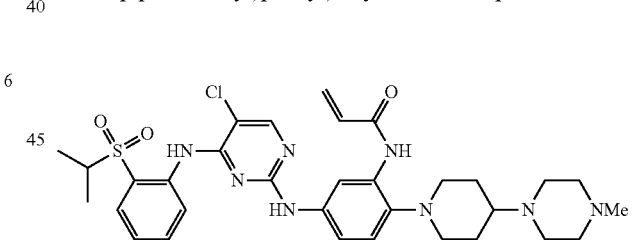

Compound 8 (30.5 mg) was obtained by using a process similar as that for preparing Compound 1, except that N-ethyl piperazine was replaced with 1-methyl-4-(4-piperidyl)piperazine. MS(ESI): m/z 683.3 (M+H)$^+$. $^1$H NMR (400 MHz, DMSO-d6) δ 9.52 (s, 1H), 8.96 (s, 1H), 8.51 (br, 1H), 8.48 (s, 1H), 8.21 (s, 1H), 8.12 (s, 1H), 7.76 (d, J=8.0 Hz, 1H), 7.53-7.51 (m, 1H), 7.25 (t, J=7.6 Hz, 1H), 6.83 (s, 1H), 6.65 (dd, J=17.0 Hz, J=9.8 Hz, 1H), 6.15 (d, J=17.0 Hz, 1H), 5.70 (d, J=9.8 Hz, 1H), 3.76 (s, 3H), 3.42 (heptet, J=6.0 Hz, 1H), 3.07-1.74 (m, 20H), 1.16 (d, J=6.0 Hz, 6H).

Example 9: Preparation of N-(5-(5-chloro-4-(2-(isopropylsulfonyl) phenylamino)pyrimidin-2-ylamino)-2-(4-(2-fluoroethyl)piperazin-1-yl)-4-methoxyphenyl)acrylamide Compound 9

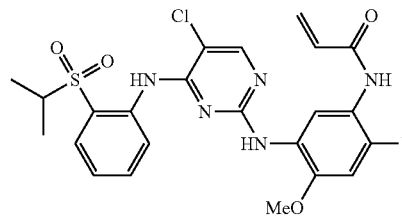

9

Compound 9 (21.3 mg) was obtained by using a process similar as that for preparing Compound 1, except that N-ethyl piperazine was replaced with 1-(2-fluoroethyl)-piperazine. MS(ESI): m/z 632.2 (M+H)+. $^1$H NMR (400 MHz, DMSO-d6) δ 9.53 (s, 1H), 8.99 (s, 1H), 8.54-8.47 (m, 2H), 8.23 (s, 1H), 8.12 (s, 1H), 7.77 (d, J=7.6 Hz, 1H), 7.57-7.53 (m, 1H), 7.26 (t, J=7.6 Hz, 1H), 6.89 (s, 1H), 6.61 (dd, J=17.4 Hz, J=9.8 Hz, 1H), 6.15 (d, J=17.4 Hz, 1H), 5.71 (d, J=10.0 Hz, 1H), 4.66-4.50 (m, 2H), 3.79 (s, 3H), 3.44 (heptet, J=6.0 Hz, 1H), 2.90 (br, 4H), 2.76-2.69 (m, 6H), 1.17 (d, J=6.0 Hz, 6H).

Example 10: Preparation of N-(5-(5-chloro-4-(2-(isopropylsulfonyl)phenylamino)pyrimidin-2-ylamino)-4-methoxy-2-(4-methyl-1,4-homopiperazin-1-yl)phenyl)acrylamide Compound 10

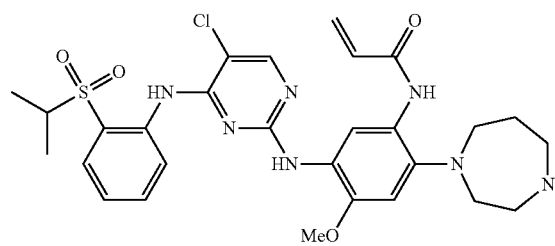

10

Compound 10 (21.3 mg) was obtained by using a process similar as that for preparing Compound 1, except that N-ethyl piperazine was replaced with N-methyl homopiperazine. MS(ESI): m/z 614.2 (M+H)+. $^1$H NMR (400 MHz, DMSO-d6) δ 9.64 (s, 1H), 9.53 (s, 1H), 8.50 (s, 1H), 8.38 (s, 1H), 8.23 (s, 1H), 8.05 (s, 1H), 7.79-7.77 (s, 1H), 7.64 (s, 1H), 7.27 (s, 1H), 7.10-7.04 (m, 1H), 6.90 (s, 1H), 6.18-6.14 (m, 1H), 5.70-5.67 (m, 1H), 3.80 (s, 3H), 3.50-1.98 (m, 14H), 1.17 (d, J=6.0 Hz, 6H).

Example 11: Preparation of N-(5-(5-chloro-4-(2-(isopropylsulfonyl)phenylamino)pyrimidin-2-ylamino)-2-(4-isopropylpiperazin-1-yl)-4-methoxy-phenyl)acrylamide Compound 11

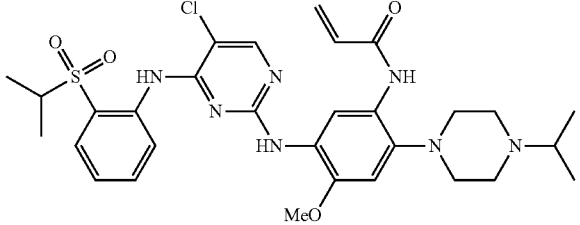

11

Compound 11 (25.6 mg) was obtained by using a process similar as that for preparing Compound 1, except that N-ethyl piperazine was replaced with N-isopropyl piperazine. MS(ESI): m/z 628.3 (M+H)+. $^1$H NMR (400 MHz, DMSO-d6) δ 9.54 (s, 1H), 9.30 (s, 1H), 8.55-8.51 (m, 2H), 8.23 (s, 2H), 7.78-7.27 (m, 3H), 6.94-6.87 (m, 1H), 6.80 (s, 1H), 6.63-6.58 (m, 1H), 6.16 (d, J=16.0 Hz, 1H), 5.70 (d, J=10.0 Hz, 1H), 3.79 (s, 3H), 3.43-2.74 (m, 10H), 1.36-1.17 (m, 12H).

Example 12: Preparation of N-(5-(5-chloro-4-(2-(isopropylsulfonyl) phenylamino)pyrimidin-2-ylamino)-2-(4-(dimethylamino)piperidin-1-yl)-4-methoxyphenyl)acrylamide Compound 12

12

Compound 12 (28.4 mg) was obtained by using a process similar as that for preparing Compound 1, except that N-ethyl piperazine was replaced with 4-(dimethylamino) piperidine. MS(ESI): m/z 628.3 (M+H)+. $^1$H NMR (400 MHz, DMSO-d6) δ 9.53 (s, 1H), 9.01 (s, 1H), 8.54-8.48 (m, 2H), 8.23 (s, 1H), 8.16 (s, 1H), 7.78 (d, J=7.6 Hz, 1H), 7.56-7.53 (m, 1H), 7.26 (t, J=7.6 Hz, 1H), 6.85 (s, 1H), 6.66 (dd, J=16.4 Hz, J=10.0 Hz, 1H), 6.17 (d, J=16.4 Hz, 1H), 5.73 (d, J=10.0 Hz, 1H), 3.78 (s, 3H), 3.43 (heptet, J=6.0 Hz, 1H), 3.14-1.88 (m, 15H), 1.17 (d, J=6.0 Hz, 6H).

Example 13: Preparation of N-(5-(5-chloro-4-(2-(isopropylsulfonyl) phenylamino)pyrimidin-2-ylamino)-4-methoxy-2-(4-(2-methoxyethyl) piperazin-1-yl)phenyl)acrylamide Compound 13

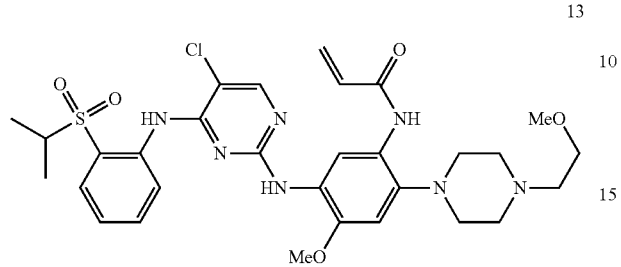

13

Compound 13 (29.1 mg) was obtained by using a process similar as that for preparing Compound 1, except that N-ethyl piperazine was replaced with 1-(2-methoxyethyl) piperazine. MS(ESI): m/z 644.3 (M+H)+. $^1$H NMR (400 MHz, DMSO-d6) δ 9.54 (s, 1H), 8.98 (s, 1H), 8.52-8.47 (m, 2H), 8.23 (s, 1H), 8.11 (s, 1H), 7.77 (d, J=7.6 Hz, 1H), 7.56-7.54 (m, 1H), 7.29-7.25 (m, 1H), 6.88 (s, 1H), 6.60 (dd, J=16.0 Hz, J=9.6 Hz, 1H), 6.15 (d, J=16.0 Hz, 1H), 5.71 (d, J=9.6 Hz, 1H), 3.78 (s, 3H), 3.49-2.57 (m, 13H), 1.24-1.17 (d, J=6.0 Hz, 6H).

Example 14: Preparation of N-(5-(5-chloro-4-(2-(isopropylsulfonyl) phenylamino)pyrimidin-2-ylamino)-2-(4-(cyclopropylmethyl)piperazin-1-yl)-4-methoxyphenyl)acrylamide Compound 14

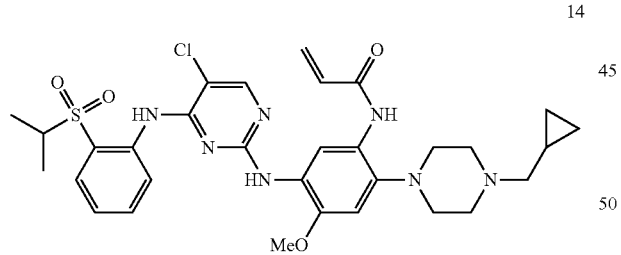

14

Compound 14 (25.4 mg) was obtained by using a process similar as that for preparing Compound 1, except that N-ethyl piperazine was replaced with 1-cyclopropylmethyl piperazine. MS(ESI): m/z 640.3 (M+H)+. $^1$H NMR (400 MHz, DMSO-d6) δ 9.54 (s, 1H), 8.99 (s, 1H), 8.53-8.47 (m, 2H), 8.23 (s, 1H), 8.12 (s, 1H), 7.77 (d, J=7.6 Hz, 1H), 7.56-7.54 (m, 1H), 7.26 (t, J=7.6 Hz, 1H), 6.87 (s, 1H), 6.59 (dd, J=16.6 Hz, J=9.6 Hz, 1H), 6.15 (d, J=16.6 Hz, 1H), 5.71 (d, J=9.6 Hz, 1H), 3.79 (s, 3H), 3.44-2.27 (m, 11H), 1.17 (d, J=6.0 Hz, 6H), 0.88-0.13 (m, 5H).

Example 15: Preparation of N-(5-(5-chloro-4-(2-(isopropylsulfonyl) phenylamino)pyrimidin-2-ylamino)-2-(4-cyclohexylpiperazin-1-yl)-4-methoxyphenyl)acrylamide Compound 15

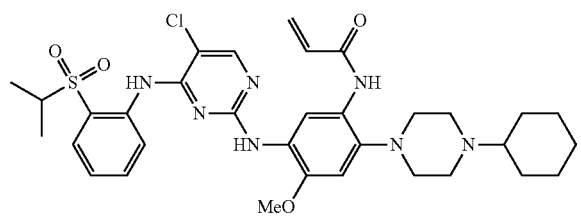

15

Compound 15 (28.7 mg) was obtained by using a process similar as that for preparing Compound 1, except that N-ethyl piperazine was replaced with 1-cyclohexyl piperazine. MS(ESI): m/z 668.3 (M+H)+. $^1$H NMR (400 MHz, DMSO-d6) δ 9.53 (s, 1H), 9.02 (s, 1H), 8.50 (br, 2H), 8.23 (s, 1H), 8.14 (s, 1H), 7.77 (d, J=7.6 Hz, 1H), 7.56-7.54 (m, 1H), 7.26 (t, J=7.6 Hz, 1H), 6.85 (s, 1H), 6.66-6.60 (m, 1H), 6.15 (d, J=16.0 Hz, 1H), 5.71 (d, J=9.6 Hz, 1H), 3.79 (s, 3H), 3.44-1.17 (m, 26H).

Example 16: Preparation of N-(2-(4-benzylpiperazin-1-yl)-5-(5-chloro-4-(2-(isopropylsulfonyl)phenylamino)pyrimidin-2-ylamino)-4-methoxyphenyl) acrylamide Compound 16

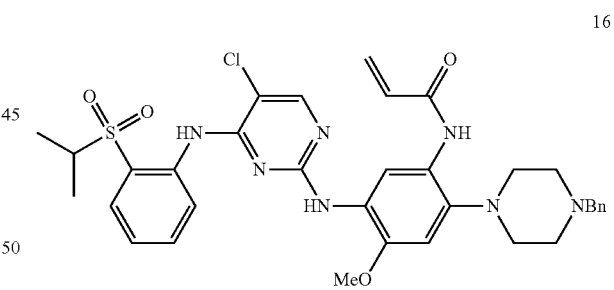

16

Compound 16 (31.2 mg) was obtained by using a process similar as that for preparing Compound 1, except that N-ethyl piperazine was replaced with 1-benzyl piperazine. MS(ESI): m/z 676.3 (M+H)+. $^1$H NMR (400 MHz, DMSO-d6) δ 9.53 (s, 1H), 9.00 (s, 1H), 8.53-8.47 (m, 2H), 8.23 (s, 1H), 8.12 (s, 1H), 7.77 (d, J=7.6 Hz, 1H), 7.56-7.54 (m, 1H), 7.36-7.26 (m, 6H), 6.89 (s, 1H), 6.60 (dd, J=16.8 Hz, J=9.6 Hz, 1H), 6.15 (d, J=16.6 Hz, 1H), 5.71 (d, J=9.6 Hz, 1H), 3.78 (s, 3H), 3.57 (s, 2H), 3.43 (heptet, J=6.0 Hz, 1H), 2.89 (br, 4H), 2.61 (br, 4H), 1.17 (d, J=6.0 Hz, 6H).

Example 17: Preparation of N-(5-(5-chloro-4-(2-(isopropylsulfonyl) phenylamino)pyrimidin-2-ylamino)-4-methoxy-2-(pyridin-4-yloxy)phenyl) acrylamide Compound 17

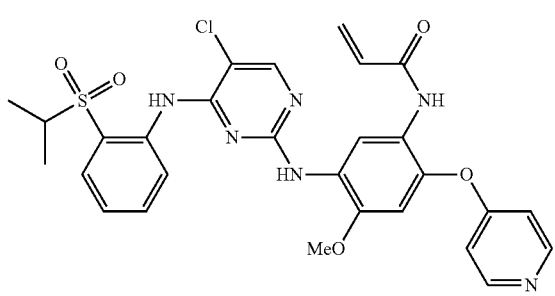

Compound 17 (19.2 mg) was obtained by using a process similar as that for preparing Compound 1, except that N-ethyl piperazine was replaced with 4-hydroxypyridine. MS(ESI): m/z 595.2 (M+H)⁺. ¹H NMR (400 MHz, DMSO-d6) δ 9.71 (s, 1H), 9.56 (s, 1H), 8.53 (br, 1H), 8.48 (s, 1H), 8.34 (s, 1H), 8.00 (s, 1H), 7.82 (d, J=4.6 Hz, 1H), 7.67 (t, J=7.2 Hz, 1H), 7.57 (t, J=7.4 Hz, 2H), 7.32 (t, J=7.0 Hz, 1H), 7.22 (s, 1H), 6.34-6.14 (m, 4H), 5.71 (d, J=9.6 Hz, 1H), 3.91 (s, 3H), 3.43 (heptet, J=6.0 Hz, 1H), 1.17 (d, J=6.0 Hz, 6H).

Example 18: Preparation of N-(5-(5-chloro-4-(3-(trifluoromethyl) phenylamino)pyrimidin-2-ylamino)-4-methoxy-2-(4-methylpiperazin-1-yl) phenyl)acrylamide Compound 18

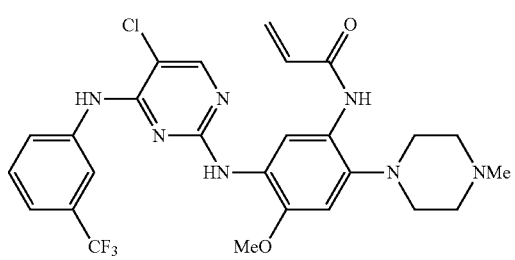

Compound 18 (21.3 mg) was obtained by using a process similar as that for preparing Compound 1, except that 2-(isopropylsulfonyl)phenylamine was replaced with 3-trifluoromethylphenylamine. MS(ESI): m/z 562.3 (M+H)⁺. ¹H NMR (400 MHz, DMSO-d6) δ 9.00 (s, 2H), 8.21-8.13 (m, 4H), 7.90 (s, 1H), 7.37-7.23 (m, 2H), 6.80 (s, 1H), 7.67-6.61 (m, 1H), 6.15 (d, J=17.0 Hz, 1H), 5.71 (d, J=10.0 Hz, 1H), 3.77 (s, 3H), 3.25-2.72 (m, 8H).

Example 19: Preparation of N-(5-(5-chloro-4-(methyl(3-(trifluoromethyl)phenyl)amino)pyrimidin-2-ylamino)-4-methoxy-2-(4-methylpiperazin-1-yl) phenyl)acrylamide Compound 19

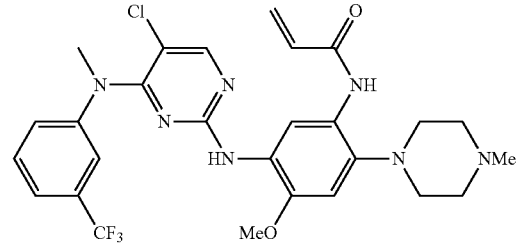

Compound 19 (22.6 mg) was obtained by using a process similar as that for preparing Compound 18, except that the intermediate compound obtained in Step 1 was methylated before being subjected to the subsequent reactions. MS(ESI): m/z 575.3 (M+H)⁺. ¹H NMR (400 MHz, DMSO-d6) δ 9.00 (s, 1H), 8.60 (s, 1H), 8.10 (s, 2H), 7.60-7.49 (m, 4H), 6.86 (s, 1H), 7.65-6.58 (m, 1H), 6.20 (d, J=17.5 Hz, 1H), 5.71 (d, J=10.0 Hz, 1H), 3.88 (s, 3H), 3.71 (s, 3H), 2.93-2.51 (m, 8H).

Example 20: Preparation of N-(5-(5-chloro-4-(2-(trifluoromethyl) phenoxy)pyrimidin-2-ylamino)-4-methoxy-2-(4-methylpiperazin-1-yl) phenyl)acrylamide Compound 20

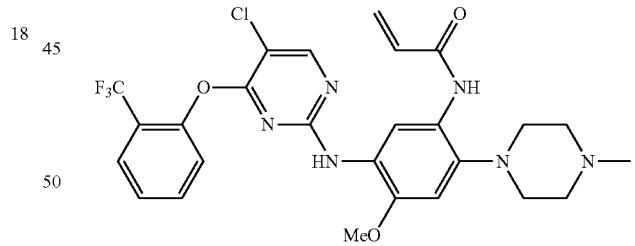

Compound 20 (21.3 mg) was obtained by using a process similar as that for preparing Compound 2, except that 2-(isopropylsulfonyl)phenylamine was replaced with 2-trifluoromethylphenol. MS(ESI): m/z 562.3 (M+H)⁺. ¹H NMR (400 MHz, DMSO-d6) δ 8.92 (s, 1H), 8.53 (s, 1H), 8.42 (s, 1H), 7.86-7.45 (m, 5H), 7.71-6.65 (m, 1H), 6.24 (d, J=17.5 Hz, 1H), 5.76 (d, J=9.2 Hz, 1H), 3.73 (s, 3H), 3.74-2.50 (m, 11H).

Example 21: Preparation of N-(5-(5-chloro-4-(3-chloro-4-fluorophenylamino)pyrimidin-2-ylamino)-4-methoxy-2-(4-methylpiperazin-1-yl)phenyl)acrylamide Compound 21

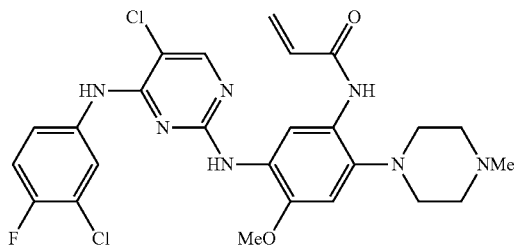

Compound 21 (25.1 mg) was obtained by using a process similar as that for preparing Compound 2, except that 2-(isopropylsulfonyl)phenylamine was replaced with 3-chloro-4-fluorophenylamine. MS(ESI): m/z 546.2 (M+H)+. 1H NMR (400 MHz, DMSO-d6) δ 9.02 (s, 1H), 8.86 (s, 1H), 8.23-7.19 (m, 7H), 6.83-6.71 (m, 2H), 6.17 (d, J=16.8 Hz, 1H), 5.71 (d, J=10.0 Hz, 1H), 3.81 (s, 3H), 3.33-2.81 (m, 11H).

Example 22: Preparation of N-(5-(5-chloro-4-(2,6-difluorophenylamino)pyrimidin-2-ylamino)-4-methoxy-2-(4-methylpiperazin-1-yl)phenyl)acrylamide Compound 22

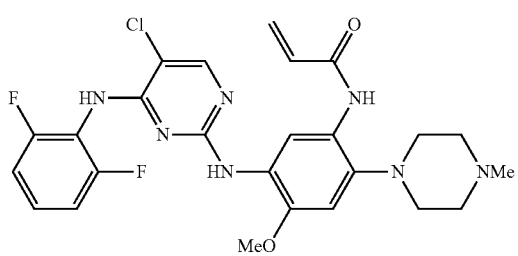

Compound 22 (27.5 mg) was obtained by using a process similar as that for preparing Compound 2, except that 2-(isopropylsulfonyl)phenylamine was replaced with 2,6-difluorophenylamine. MS(ESI): m/z 530.2 (M+H)+. 1H NMR (400 MHz, DMSO-d6) δ 8.86 (s, 1H), 8.78 (s, 1H), 8.10 (s, 1H), 7.90 (s, 1H), 7.67 (s, 1H), 7.32-7.08 (m, 3H), 6.71 (s, 1H), 6.62 (dd, J=16.8 Hz, J=10.2 Hz, 1H), 6.22 (d, J=16.8 Hz, 1H), 5.75 (d, J=10.2 Hz, 1H), 3.77 (s, 3H), 2.94-2.30 (m, 11H).

Example 23: Preparation of N-(5-(5-chloro-4-(2-pivalamidophenylamino)pyrimidin-2-ylamino)-4-methoxy-2-(4-methylpiperazin-1-yl)phenyl)acrylamide Compound 23

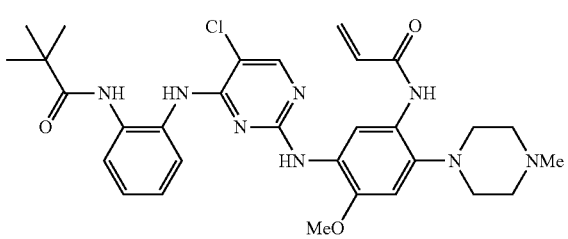

Compound 23 (29.0 mg) was obtained by using a process similar as that for preparing Compound 2, except that 2-(isopropylsulfonyl)phenylamine was replaced with 2-aminophenylpivalamide. MS(ESI): m/z 593.3 (M+H)+. 1H NMR (400 MHz, DMSO-d6) δ 9.36 (s, 1H), 8.97 (s, 1H), 8.24 (s, 1H), 8.11-8.09 (m, 2H), 7.98 (s, 1H), 5.74 (d, J=7.4 Hz, 1H), 7.24-7.12 (m, 3H), 6.79 (s, 1H), 6.64 (dd, J=16.0 Hz, J=10.0 Hz, 1H), 6.16 (d, J=16.0 Hz, 1H), 5.74 (d, J=10.0 Hz, 1H), 3.78 (s, 3H), 2.89-2.36 (m, 11H), 1.21 (s, 9H).

Example 24: Preparation of N-(5-(4-(2-(isopropylsulfonyl)phenylamino)-5-methylpyrimidin-2-ylamino)-4-methoxy-2-(4-(4-methylpiperazin-1-yl)piperidin-1-yl)phenyl)acrylamide Compound 24

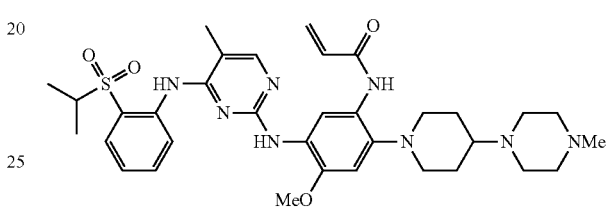

Compound 24 (28.1 mg) was obtained by using a process similar as that for preparing Compound 1, except that 2,4,5-trichloropyrimidine was replaced with 2,4-dichloro-5-methylpyrimidine in Step 1, and N-ethyl piperazine was replaced with 1-methyl-4-(4-piperidyl)piperazine in Step 3. MS(ESI): m/z 663.3 (M+H)+. 1H NMR (400 MHz, DMSO-d6) δ 9.02 (s, 1H), 8.95 (s, 1H), 8.61 (d, J=8.0 Hz, 1H), 8.31 (s, 1H), 7.98 (s, 1H), 7.88 (s, 1H), 7.74 (d, J=7.8 Hz, 1H), 7.53 (t, J=7.8 Hz, 1H), 7.20-7.16 (m, 1H), 6.80 (s, 1H), 6.64 (dd, J=17.0 Hz, J=10.6 Hz, 1H), 6.13 (d, J=17.0 Hz, 1H), 5.69 (d, J=10.6 Hz, 1H), 3.78 (s, 3H), 3.42 (heptet, J=6.0 Hz, 1H), 3.07-1.74 (m, 23H), 1.16 (d, J=6.0 Hz, 6H).

Example 25: Preparation of N-(5-(5-chloro-4-(2-(isopropylsulfonyl) phenylamino)pyrimidin-2-ylamino)-2-(4-(4-methylpiperazin-1-yl)piperidin-1-yl)phenyl)acrylamide Compound 25

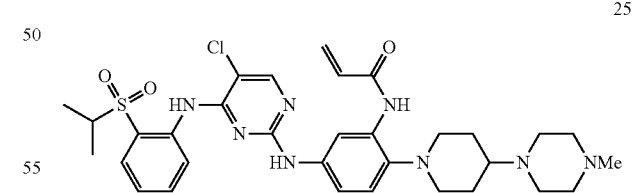

Compound 25 (33.5 mg) was obtained by using a process similar as that for preparing Compound 1, except that 4-fluoro-2-methoxy-5-nitrophenylamine was replaced with 4-fluoro-3-nitrophenylamine in Step 2, and N-ethyl piperazine was replaced with 1-methyl-4-(4-piperidyl)piperazine in Step 3. MS(ESI): m/z 653.3 (M+H)+. 1H NMR (400 MHz, DMSO-d6) δ 10.04 (s, 1H), 9.57 (s, 1H), 8.54 (d, J=8.2 Hz, 1H), 8.32 (br, 1H), 8.20 (s, 1H), 7.81 (d, J=8.0 Hz, 1H), 7.54-7.51 (m, 1H), 7.7.35-7.28 (m, 2H), 7.10 (d, J=8.4 Hz, 1H), 6.42 (dd, J=16.2 Hz, J=9.0 Hz, 1H), 6.18 (d, J=16.2

Hz, 1H), 5.71 (d, J=9.0 Hz, 1H), 3.42 (heptet, J=6.0 Hz, 1H), 3.01-1.50 (m, 20H), 1.16 (d, J=6.0 Hz, 6H).

Example 26: Preparation of N-(5-(4-(2-(isopropyl-sulfonyl) phenylamino)-5-methylpyrimidin-2-ylamino)-2-(4-(4-methylpiperazin-1-yl) piperidin-1-yl)phenyl)acrylamide Compound 26

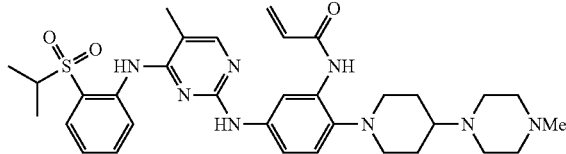

Compound 26 (34.6 mg) was obtained by using a process similar as that for preparing Compound 1, except that 2,4,5-trichloropyrimidine was replaced with 2,4-dichloro-5-methylpyrimidine in Step 1, 4-fluoro-2-methoxy-5-nitrophenylamine was replaced with 4-fluoro-3-nitrophenylamine in Step 2, and N-ethyl piperazine was replaced with 1-methyl-4-(4-piperidyl)piperazine in Step 3. MS(ESI): m/z 633.4 (M+H)+. 1H NMR (400 MHz, DMSO-d6) δ 10.05 (s, 1H), 9.09 (s, 1H), 8.68 (d, J=8.6 Hz, 1H), 8.36 (s, 1H), 8.08 (s, 1H), 7.98 (s, 1H), 7.80 (d, J=7.8 Hz, 1H), 7.59-7.56 (m, 1H), 7.34-7.07 (m, 3H), 6.45 (dd, J=17.0 Hz, J=10.0 Hz, 1H), 6.18 (d, J=17.0 Hz, 1H), 5.69 (d, J=10.0 Hz, 1H), 3.42 (heptet, J=6.0 Hz, 1H), 3.07-1.74 (m, 23H), 1.18 (d, J=6.0 Hz, 6H).

Example 27: Preparation of N-(5-(5-chloro-4-(2-(isopropylsulfonyl)phenylamino)pyrimidin-2-ylamino)-2-(2-(dimethylamino)ethoxy)-4-methoxy-phenyl)acrylamide Compound 27

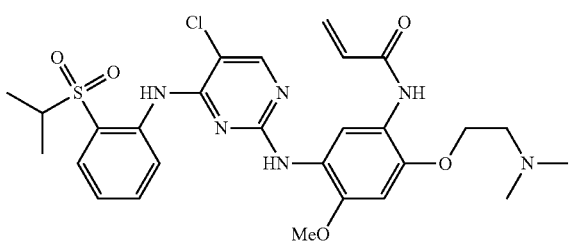

Compound 27 (28.9 mg) was obtained by using a process similar as that for preparing Compound 1, except that N-ethyl piperazine was replaced with 2-(dimethylamino) ethanol. MS(ESI): m/z 589.2 (M+H)+. 1H NMR (400 MHz, DMSO-d6) δ 9.96 (s, 1H), 9.53 (s, 1H), 8.53 (s, 1H), 8.20-8.18 (m, 2H), 7.77-7.10 (m, 5H), 6.87 (s, 1H), 6.14 (d, J=17.0 Hz, 1H), 5.65 (d, J=10.6 Hz, 1H), 4.43 (br, 2H), 3.81 (s, 3H), 3.60 (br, 2H), 3.43 (heptet, J=6.0 Hz, 1H), 2.84 (s, 6H), 1.17 (d, J=6.0 Hz, 6H).

Example 28: Preparation of (R)—N-(5-(5-chloro-4-(2-(isopropylsulfonyl)phenylamino)pyrimidin-2-ylamino)-4-methoxy-2-(3-methylpiperazin-1-yl)phenyl)acrylamide Compound 28

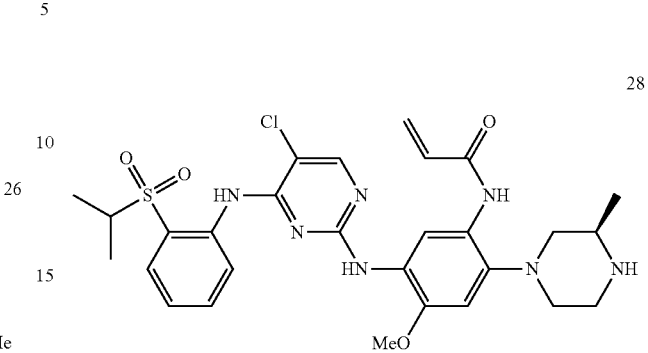

Compound 28 (15.3 mg) was obtained by using a process similar as that for preparing Compound 4, except that N-Boc piperazine was replaced with (R)-2-methyl-N-Boc piperazine. MS(ESI): m/z 600.2 (M+H)+. 1H NMR (400 MHz, DMSO-d6) δ 9.51 (s, 1H), 9.06 (s, 1H), 8.54-8.50 (m, 2H), 8.24-8.21 (m, 1H), 7.80-5.68 (m, 7H), 3.80 (s, 3H), 3.42-1.16 (m, 19H).

Example 29: Preparation of (S)—N-(5-(5-chloro-4-(2-(isopropylsulfonyl)phenylamino)pyrimidin-2-ylamino)-4-methoxy-2-(3-methylpiperazin-1-yl)phenyl)acrylamide Compound 29

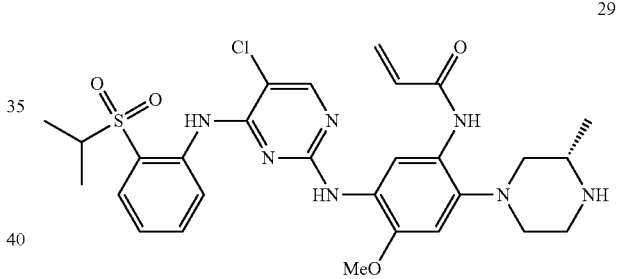

Compound 29 (12.0 mg) was obtained by using a process similar as that for preparing Compound 4, except that N-Boc piperazine was replaced with (S)-2-methyl-N-Boc piperazine. MS(ESI): m/z 600.2 (M+H)+. 1H NMR (400 MHz, DMSO-d6) δ 9.54 (s, 1H), 9.08 (s, 1H), 8.60-8.52 (m, 2H), 8.23 (s, 1H), 7.80-6.83 (m, 4H), 6.68 (dd, J=17.0 Hz, J=9.2 Hz, 1H), 6.17 (d, J=17.0 Hz, 1H), 5.73 (d, J=9.2 Hz, 1H), 3.80 (s, 3H), 3.54-1.17 (m, 19H).

Example 30: Preparation of N-(5-(5-chloro-4-(2-(isopropylsulfonyl) phenylamino)pyrimidin-2-ylamino)-4-methoxy-2-(4-(4-methylpiperazin-1-yl) piperidin-1-yl)phenyl)propionamide Compound 30

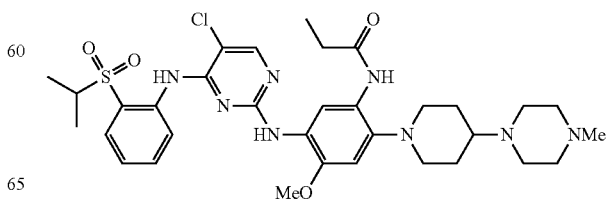

Compound 30 (29.4 mg) was obtained by using a process similar as that for preparing Compound 8, except that acryloyl chloride was replaced with propionyl chloride. MS(ESI): m/z 685.4 (M+H)+. 1H NMR (400 MHz, DMSO-d6) δ 9.55 (s, 1H), 8.69 (s, 1H), 8.53 (br, 1H), 8.50 (s, 1H), 8.22 (s, 1H), 8.05 (s, 1H), 7.80-7.27 (m, 3H), 6.82 (s, 1H), 3.76 (s, 3H), 3.45-1.01 (m, 32H).

Example 31: Preparation of N-(5-(4-(2-(isopropyl-sulfonyl)phenylamino)-5-methylpyrimidin-2-ylamino)-4-methoxy-2-(4-(4-methylpiperazin-1-yl)piperidin-1-yl)phenyl)propionamide Compound 31

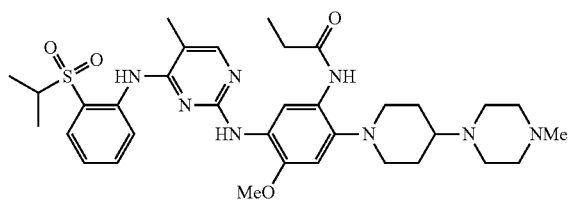

31

Compound 31 (29.0 mg) was obtained by using a process similar as that for preparing Compound 24 except that acryloyl chloride was replaced with propionyl chloride. MS(ESI): m/z 665.3 (M+H)+0.1H NMR (400 MHz, DMSO-d6) δ 9.03 (s, 1H), 8.65 (s, 1H), 8.62 (s, 1H), 8.23 (s, 1H), 7.98 (s, 1H), 7.87 (s, 1H), 7.76-7.19 (m, 3H), 6.78 (s, 1H), 3.76 (s, 3H), 3.44-1.01 (m, 35H).

Example 32: Preparation of N-(5-(5-chloro-4-(2-(N,N-dimethylsulfamido)phenylamino)pyrimidin-2-ylamino)-4-methoxy-2-(4-methylpiperazin-1-yl)phenyl)acrylamide Compound 32

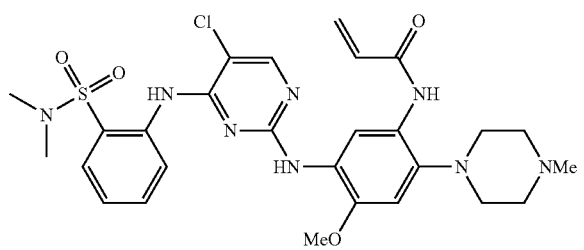

32

Compound 32 (35.2 mg) was obtained by using a process similar as that for preparing Compound 2, except that the raw material 2-(isopropylsulfonyl)phenylamine was replaced with 2-(N,N-dimethylsulfonyl)phenylamine. MS(ESI): m/z 601.2 (M+H)+. 1H NMR (400 MHz, DMSO-d6) δ 9.38 (s, 1H), 8.96 (s, 1H), 8.50-8.44 (m, 2H), 8.20 (s, 1H), 8.12 (s, 1H), 7.75-6.57 (m, 5H), 6.15 (d, J=16.6 Hz, 1H), 5.71 (d, J=9.6 Hz, 1H), 3.79 (s, 3H), 2.89 (br, 4H), 2.66 (s, 6H), 2.61 (br, 4H), 2.31 (s, 3H).

Example 33: Preparation of N-(5-(5-chloro-4-(2-(isopropylsulfonyl)phenylamino)pyrimidin-2-ylamino)-2-(1H-imidazol-1-yl)-4-methoxyphenyl)acrylamide Compound 33

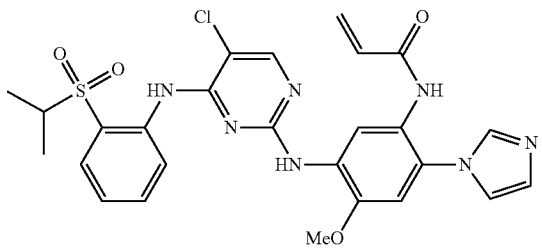

33

Compound 33 (3.8 mg) was obtained by using a process similar as that for preparing Compound 1, except that N-ethyl piperazine was replaced with imidazole. MS(ESI): m/z 568.1 (M+H)+.

Example 34: Preparation of N-(5-(5-chloro-4-(2-(isopropylsulfonyl) phenylamino)pyrimidin-2-ylamino)-4-methoxy-2-((1-methylpiperidin-2-yl)methoxy)phenyl)acrylamide Compound 34

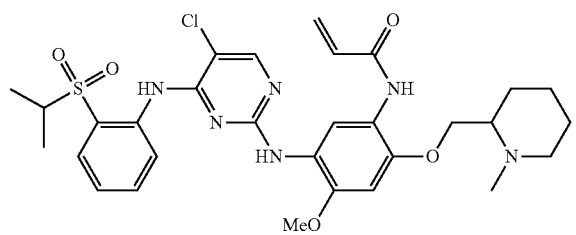

34

Compound 34 (4.5 mg) was obtained by using a process similar as that for preparing Compound 1, except that N-ethyl piperazine was replaced with (N-methyl-piperidin-2-yl)-methanol. MS(ESI): m/z 629.2 (M+H)+.

Example 35: Preparation of N-(5-(5-chloro-4-(thiophen-2-ylmethylamino)pyrimidin-2-ylamino)-4-methoxy-2-(4-methylpiperazin-1-yl)phenyl)acrylamide Compound 35

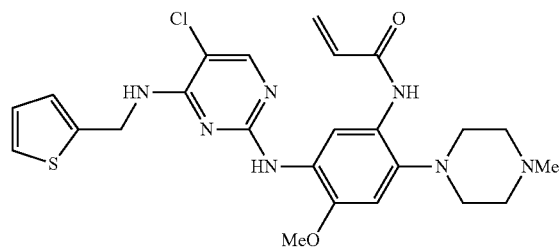

35

Compound 35 (30.2 mg) was obtained by using a process similar as that for preparing Compound 2, except that the intermediate was obtained by replacing 2-(isopropylsulfonyl)phenylamine with thiophene-2-methylamine in ethanol and adding 2 equivalents of N,N-diisopropylethylamine in Step 1. MS(ESI): m/z 514.2 (M+H)+. 1H NMR (400 MHz, DMSO-d6) δ 8.97 (s, 1H), 8.73 (s, 1H), 7.94 (s, 1H), 7.80 (s, 1H), 7.64 (s, 1H), 7.29 (s, 1H), 6.89-6.83 (m, 3H), 6.58 (dd, J=17.0 Hz, J=10.4 Hz, 1H), 6.19 (d, J=17.0 Hz, 1H), 5.70 (d, J=10.4 Hz, 1H), 4.80 (s, 2H), 3.85 (s, 3H), 2.87-2.32 (m, 11H).

Example 36: Preparation of N-(5-(5-chloro-4-(cyclopropylamino)pyrimidin-2-ylamino)-4-methoxy-2-(4-methylpiperazin-1-yl)phenyl)acrylamide Compound 36

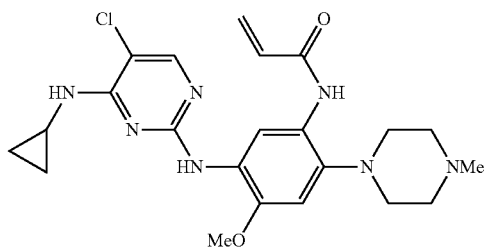

Compound 36 (5.3 mg) was obtained by using a process similar as that for preparing Compound 35, except that thiophene-2-methylamine was replaced with cyclopropylamine. MS(ESI): m/z 458.2 (M+H)+.

Example 37: Preparation of N-(5-(5-chloro-4-(2-(isopropylsulfonyl)phenylamino)pyrimidin-2-ylamino)-2-(4-ethylpiperazin-1-yl)-4-isopropoxyphenyl)acrylamide Compound 37

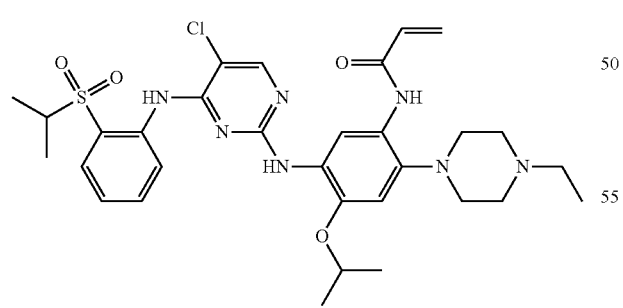

A process similar as that for preparing Compound 1 was used, except that 4-fluoro-2-methoxy-5-nitrophenylamine was replaced with 4-N-ethylpiperidyl-2-isopropoxy-5-nitrophenylamine. MS(ESI): m/z 642.26 (M+H)+.

Example 38: Preparation of N-(5-(5-chloro-4-(2-(isopropylsulfonyl)phenylamino)pyrimidin-2-ylamino)-4-methoxy-2-(4-propylpiperazin-1-yl)phenyl)acrylamide Compound 38

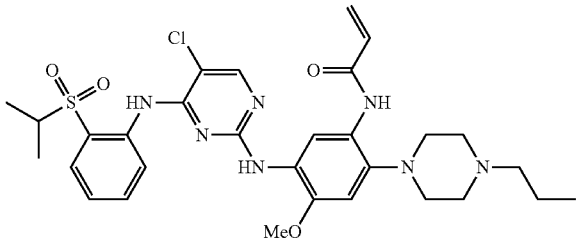 [SMILES: C=CC(=O)Nc1cc(Nc2ncc(Cl)c(Nc3ccccc3S(=O)(=O)C(C)C)n2)c(OC)cc1N1CCN(CCC)CC1]

A process similar as that for preparing Compound 1 was used. MS(ESI): m/z 629.2 (M+H)+.

Example 39: Preparation of N-(5-(5-chloro-4-(2-(isopropylsulfonyl)phenylamino)pyrimidin-2-ylamino)-4-ethoxy-2-(4-ethylpiperazin-1-yl)phenyl)acrylamide Compound 39

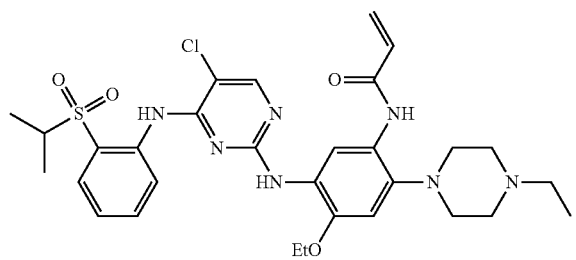 [SMILES: C=CC(=O)Nc1cc(Nc2ncc(Cl)c(Nc3ccccc3S(=O)(=O)C(C)C)n2)c(OCC)cc1N1CCN(CC)CC1]

A process similar as that for preparing Compound 1 was used. MS(ESI): m/z 629.2 (M+H)+.

Example 40: Preparation of N-(5-(5-chloro-4-((2-(isopropylsulfonyl)phenylamino)pyrimidin-2-ylamino)-2-(4-isobutylpiperazin-1-yl)-4-methoxyphenyl)acrylamide Compound 40

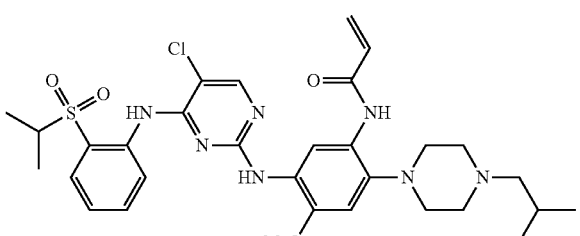

A process similar as that for preparing Compound 1 was used. MS(ESI): m/z 643.2 (M+H)+.

Example 41: Preparation of N-(5-(5-chloro-4-(2-(isopropylsulfonyl)phenylamino)pyrimidin-2-ylamino)-2-(4-ethylpiperidin-1-yl)-4-(trifluoromethoxy)phenyl)acrylamide Compound 41

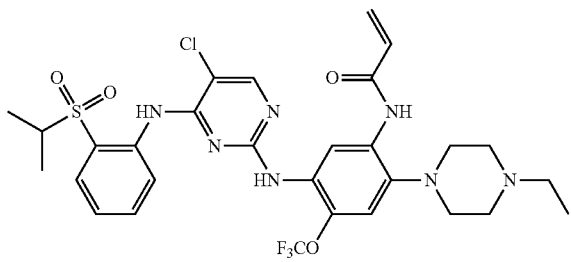 [SMILES: C=CC(=O)Nc1cc(Nc2ncc(Cl)c(Nc3ccccc3S(=O)(=O)C(C)C)n2)c(OC(F)(F)F)cc1N1CCN(CC)CC1]

A process similar as that for preparing Compound 1 was used. MS(ESI): m/z 669.1 (M+H)+.

Example 42: Preparation of N-(5-(5-chloro-4-(2-(isopropylsulfonyl)phenylamino)pyrimidin-2-ylamino)-2-(1-ethylpiperidine-4-yl)-4-methoxyphenyl)acrylamide Compound 42

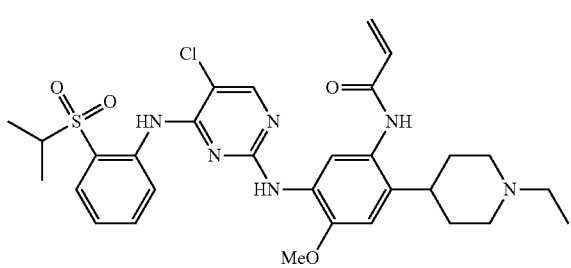 [SMILES: C=CC(=O)Nc1cc(Nc2ncc(Cl)c(Nc3ccccc3S(=O)(=O)C(C)C)n2)c(OC)cc1C1CCN(CC)CC1]

A process similar as that for preparing Compound 1 was used. MS(ESI): m/z 614.2 (M+H)+.

Example 43: Preparation of N-(5-(5-chloro-4-(2-(isopropylsulfonyl)phenylamino)pyrimidin-2-ylamino)-2-(1-ethylpiperidin-4-yl)-4-isopropoxyphenyl)acrylamide Compound 43

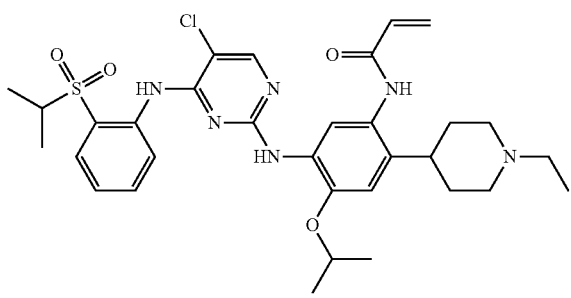 [SMILES: C=CC(=O)Nc1cc(Nc2ncc(Cl)c(Nc3ccccc3S(=O)(=O)C(C)C)n2)c(OC(C)C)cc1C1CCN(CC)CC1]

A process similar as that for preparing Compound 1 was used. MS(ESI): m/z 640.2599 (M+H)+.

Example 44: Preparation of N-(5-(5-chloro-4-(2-(isopropylsulfonyl) phenylamino)pyrimidin-2-ylamino)-4-isopropoxy-2-(1-methylpiperidine-4-yl) phenyl)acrylamide Compound 44

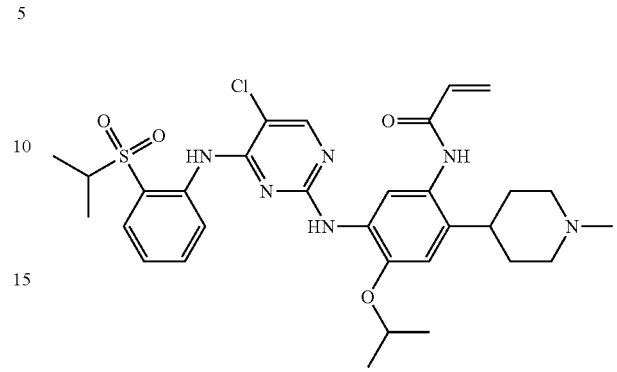

A process similar as that for preparing Compound 1 was used. MS(ESI): m/z 626.2442 (M+H)+.

Example 45: Preparation of N-2-(1-ethylpiperidin-4-yl)-4-isopropoxy-5-(4(2-(isopropylsulfonyl)phenylamino)-5-methylpyrimidin-2-ylamino)phenyl) acrylamide Compound 45

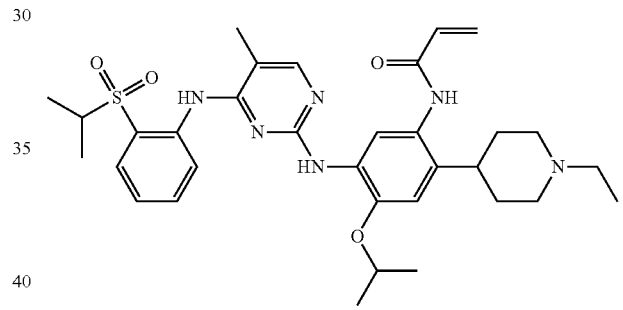

A process similar as that for preparing Compound 1 was used. MS(ESI): m/z 620.3145 (M+H)+.

Example 46: Preparation of N-(4-isopropoxy-5-(4-(2-(isopropylsulfonyl)phenylamino)-5-methylpyrimidin-2-ylamino)-2-(1-methylpiperidin-4-yl)phenyl)acrylamide Compound 46

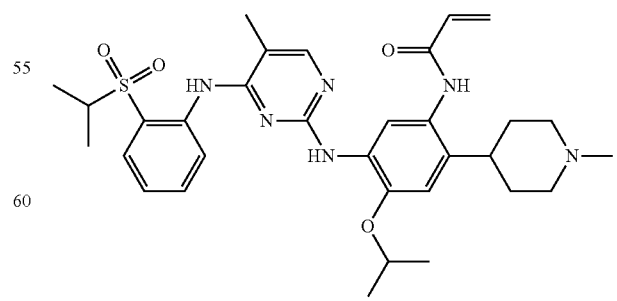

A process similar as that for preparing Compound 1 was used. MS(ESI): m/z 606.2988 (M+H)+.

Example 47: Preparation of N-(5-(5-chloro-4-(2-(dimethylphosphinoyl)phenylamino)pyrimidin-2-ylamino)-2-(4-ethylpiperazin-1-yl)-4-methoxyphenyl)acrylamide 47

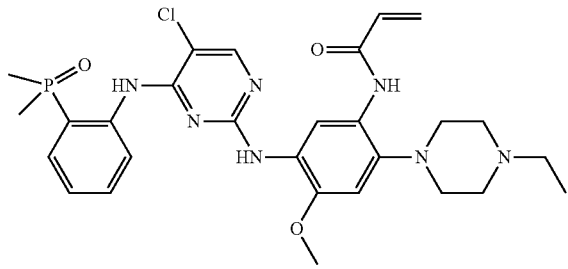 [SMILES: C=CC(=O)Nc1cc(Nc2ncc(Cl)c(Nc3ccccc3P(C)(C)=O)n2)c(OC)cc1N1CCN(CC)CC1]

A process similar as that for preparing Compound 1 was used. MS(ESI): m/z 584.23 (M+H)+.

Example 48: Preparation of N-(5-(5-chloro-4-(2-(dimethylphosphinoyl)phenylamino)pyrimidin-2-ylamino)-4-methoxy-2-(4-(piperidin-1-yl)piperidin-1-yl)phenyl)acrylamide 48

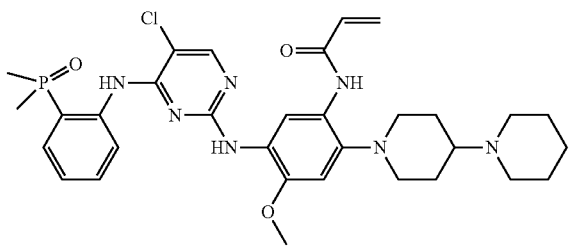 [SMILES: C=CC(=O)Nc1cc(Nc2ncc(Cl)c(Nc3ccccc3P(C)(C)=O)n2)c(OC)cc1N1CCC(N2CCCCC2)CC1]

A process similar as that for preparing Compound 1 was used. MS(ESI): m/z 638.27 (M+H)+.

Example 49: Preparation of N-(5-(5-chloro-4-(2-(dimethylphosphinoyl)phenylamino)pyrimidin-2-ylamino)-2-(4-(dimethylamino)piperidin-1-yl)-4-methoxyphenyl)acrylamide 49

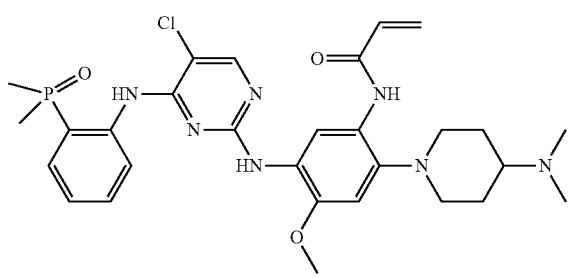

A process similar as that for preparing Compound 1 was used. MS(ESI): m/z 598.24 (M+H)+.

Example 50: Preparation of N-(5-(5-chloro-4-((2-(dimethylphosphinoyl)phenylamino)pyrimidin-2-ylamino)-4-methoxy-2-(4-(4-methylpiperazin-1-yl)piperidin-1-yl)phenyl)acrylamide 50

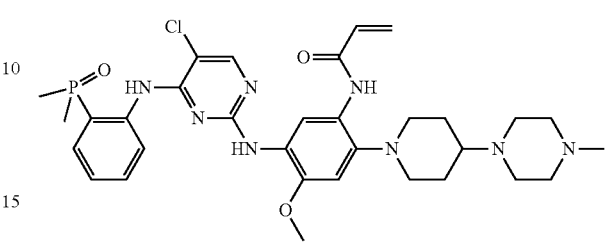

A process similar as that for preparing Compound 1 was used. MS(ESI): m/z 653.28 (M+H)+.

Example 51: Preparation of N-(5-(5-chloro-4-(2-(dimethylphosphinoyl)phenylamino)pyrimidin-2-ylamino)-4-methoxy-2-(4-morpholinylpiperidin-1-yl)phenyl)acrylamide 51

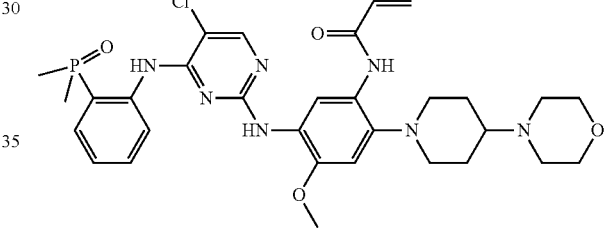

A process similar as that for preparing Compound 1 was used. MS(ESI): m/z 640.25 (M+H)+.

Example 52: Preparation of N-(5-(5-chloro-4-(2-(dimethylphosphinoyl)phenylamino)pyrimidin-2-ylamino)-4-methoxy-2-(4-methyl-1,4-homopiperazin-1-yl)phenyl)acrylamide 52

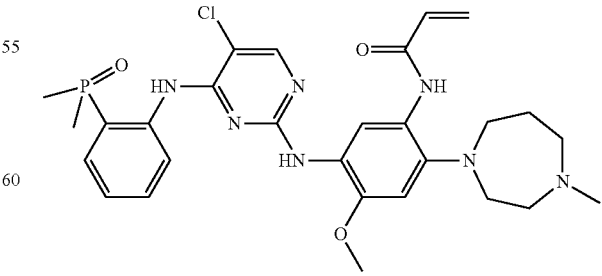

A process similar as that for preparing Compound 1 was used. MS(ESI): m/z 584.23 (M+H)+.

Example 53: Preparation of N-(5-(5-chloro-4-(2-(dimethylphosphinoyl)phenylamino)pyrimidin-2-ylamino)-4-methoxy-2-(4-(1-methylpiperidin-4-yl)piperazin-1-yl)phenyl)acrylamide 53

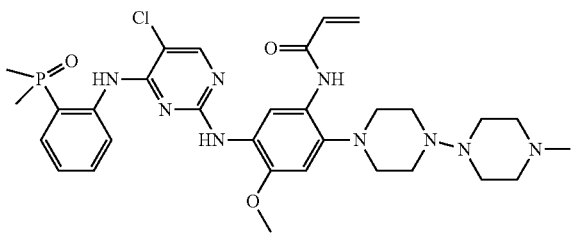

A process similar as that for preparing Compound 1 was used. MS(ESI): m/z 653.28 (M+H)+.

Example 54: Preparation of N-(5-(5-chloro-4-(2-(dimethylphosphinoyl)phenylamino)pyrimidin-2-ylamino)-4-methoxy-2-(4-(1-methylsulfonyl)piperidin-4-yl)piperazin-1-yl)phenyl)acrylamide 54

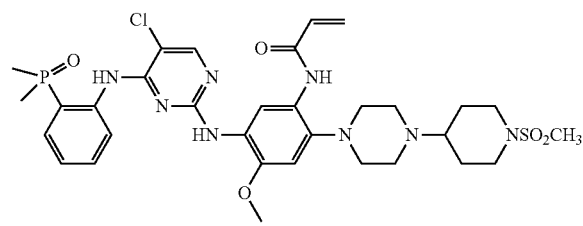

A process similar as that for preparing Compound 1 was used. MS(ESI): m/z 717.25 (M+H)+.

Example 55: Preparation of N-(5-(5-chloro-4-(2-cyanophenylamino)pyrimidin-2-ylamino)-2-(4-ethyl-piperazin-1-yl)-4-methoxyphenyl)acrylamide 55

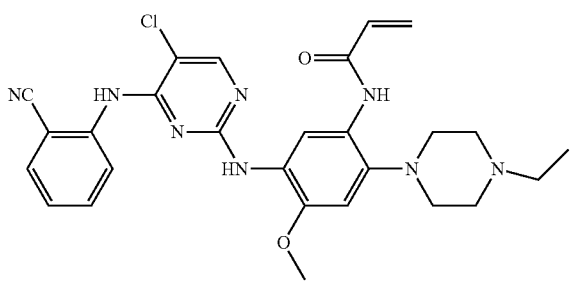

A process similar as that for preparing Compound 1 was used. MS(ESI): m/z 533.21 (M+H)+.

Example 56: Preparation of N-(5-(5-chloro-4-(2-cyanophenylamino)pyrimidin-2-ylamino)-4-methoxy-2-(4-(methylsulfonyl) piperazin-1-yl)phenyl)acrylamide 56

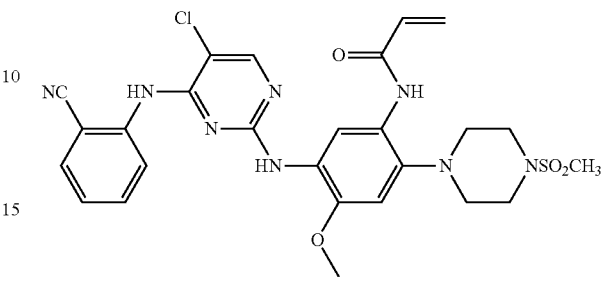

A process similar as that for preparing Compound 1 was used. MS(ESI): m/z 583.16 (M+H)+.

Example 57: Preparation of N-(5-(5-chloro-4-(2-cyanophenylamino) pyrimidin-2-ylamino)-4-methoxy-2-(4-(4-methylpiperazin-1-yl)piperidin-1-yl)phenyl)acrylamide 57

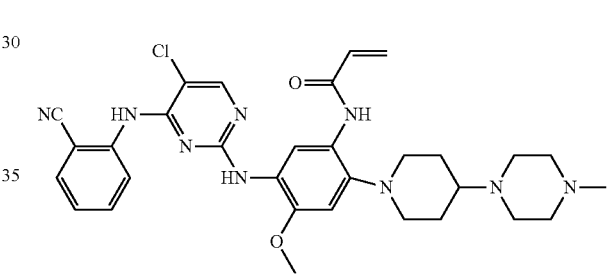

A process similar as that for preparing Compound 1 was used. MS(ESI): m/z 602.27 (M+H)+.

Example 58: Preparation of N-(5-(5-chloro-4-(2-cyanophenylamino)pyrimidin-2-ylamino)-4-methoxy-2-(4-methylpiperazin-1-yl)phenyl)acrylamide 58

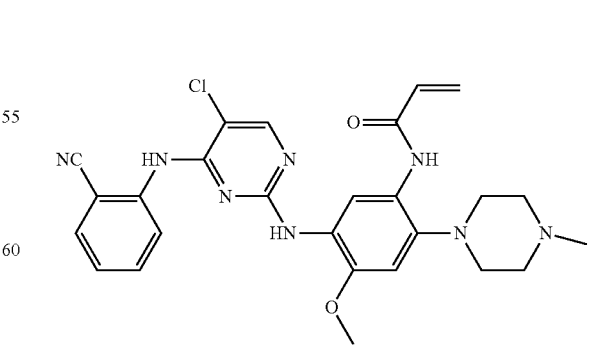

A process similar as that for preparing Compound 1 was used. MS(ESI): m/z 519.20 (M+H)+.

Example 59: Preparation of N-(5-(5-chloro-4-(2-cyanophenylamino) pyrimidin-2-ylamino)-4-methoxy-2-(4-(4-(methylsulfonyl)piperazin-1-yl)piperidin-1-yl)phenyl)acrylamide 59

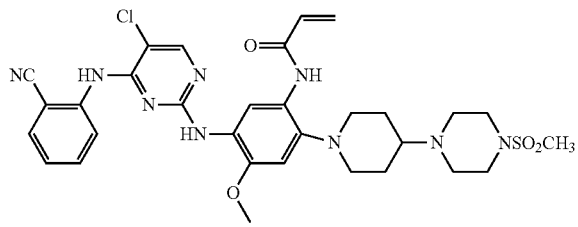

A process similar as that for preparing Compound 1 was used. MS(ESI): m/z 666.23 (M+H)+.

Example 60: Preparation of N-(5-(5-chloro-4-(2-cyanophenylamino) pyrimidin-2-ylamino)-4-methoxy-2-(4-(1-methylpiperidin-4-yl)piperazin-1-yl)phenyl)acrylamide 60

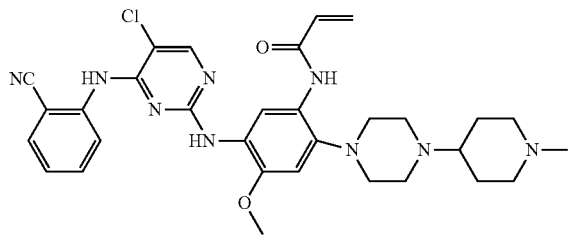 [SMILES: C=CC(=O)Nc1cc(Nc2ncc(Cl)c(Nc3ccccc3C#N)n2)c(OC)cc1N1CCC(N2CCN(C)CC2)CC1]

A process similar as that for preparing Compound 1 was used. MS(ESI): m/z 602.27 (M+H)+.

Example 61: Preparation of N-(5-(5-chloro-4-(2-cyanophenylamino) pyrimidin-2-ylamino)-4-methoxy-2-morpholinylphenyl)acrylamide 61

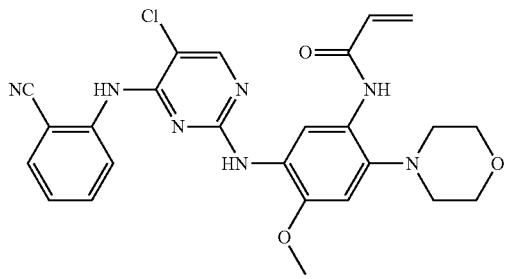 [SMILES: C=CC(=O)Nc1cc(Nc2ncc(Cl)c(Nc3ccccc3C#N)n2)c(OC)cc1N1CCOCC1]

A process similar as that for preparing Compound 1 was used. MS(ESI): m/z 506.17 (M+H)+.

Example 62: Preparation of N-(5-(5-chloro-4-(2-cyanophenylamino)pyrimidin-2-ylamino)-2-(4-isopropylpiperazin-1-yl)-4-methoxyphenyl)acrylamide 62

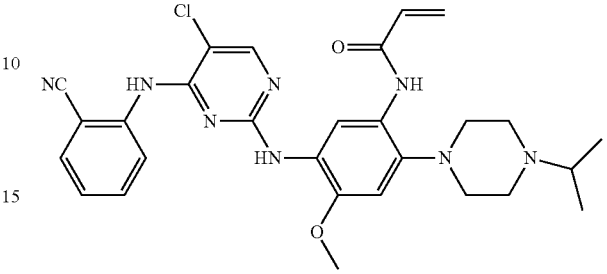

A process similar as that for preparing Compound 1 was used. MS(ESI): m/z 547.23 (M+H)+.

Example 63: Preparation of N-(5-(5-chloro-4-(2-cyanophenylamino) pyrimidin-2-ylamino)-4-methoxy-2-(4-morpholinylpiperidin-1-yl)phenyl) acrylamide 63

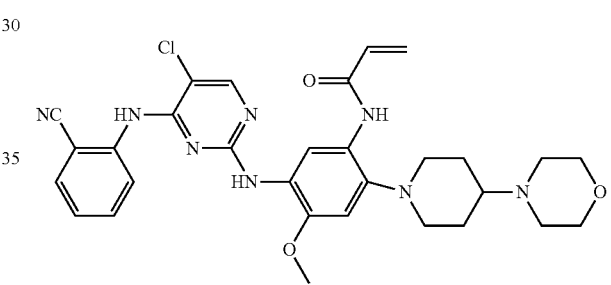

A process similar as that for preparing Compound 1 was used. MS(ESI): m/z 589.24 (M+H)+.

Example 64: Preparation of 2-(2-(5-acrylamido-2-methoxy-4-(4-methylpiperazin-1-yl)phenylamino)-5-chloropyrimidin-4-ylamino)-N-methylbenzamide 64

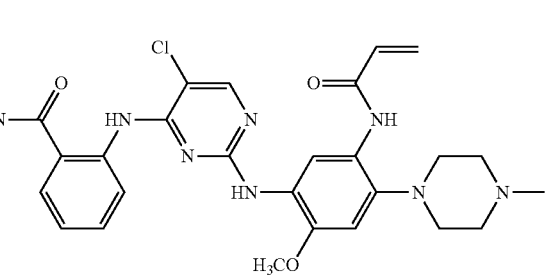

A process similar as that for preparing Compound 1 was used. MS(ESI): m/z 551.22 (M+H)+.

Example 65: Preparation of 2-(2-(5-acrylamido-4-(4-ethylpiperazin-1-yl)-2-methoxyphenylamino-5-chloropyrimidin-4-ylamino)-N-methylbenzamide 65

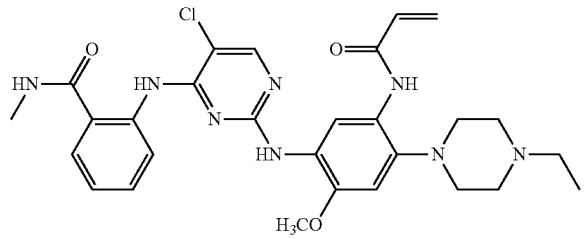 [SMILES: C=CC(=O)Nc1cc(Nc2ncc(Cl)c(Nc3ccccc3C(=O)NC)n2)c(OC)cc1N1CCN(CC)CC1]

A process similar as that for preparing Compound 1 was used. MS(ESI): m/z 565.24 (M+H)+.

Example 66: Preparation of 2-(2-(5-acrylamido-2-methoxy-4-(4-(4-methylpiperazin-1-yl)piperidin-1-yl)phenylamino)-5-chloropyrimidin-4-ylamino)-N-methylbenzamide 66

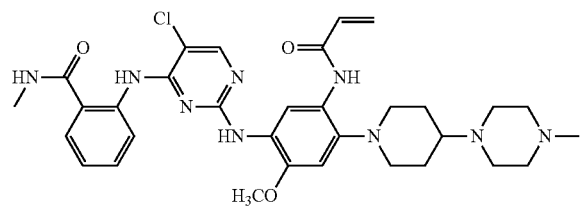

A process similar as that for preparing Compound 1 was used. MS(ESI): m/z 634.30 (M+H)+.

Example 67: Preparation of 2-(2-(5-acrylamido-2-methoxy-4-(4-morpholinylpiperidin-1-yl)phenylamino)-5-chloropyrimidin-4-ylamino)-N-methylbenzamide 67

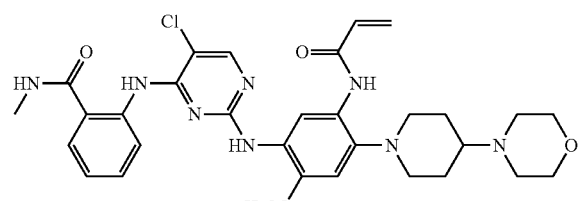

A process similar as that for preparing Compound 1 was used. MS(ESI): m/z 621.27 (M+H)+.

Example 68: Preparation of 2-(2-(4-(4-ethanoylpiperazin-1-yl)-5-acrylamido-2-methoxyphenylamino)-5-chloropyrimidin-4-ylamino)-N-methylbenzamide 68

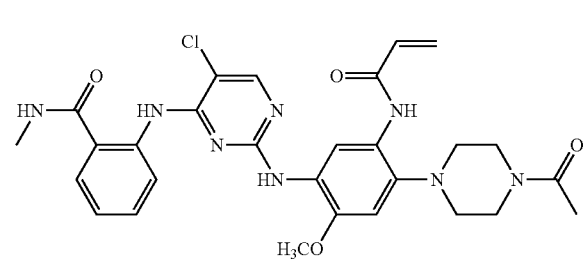 [SMILES: C=CC(=O)Nc1cc(Nc2ncc(Cl)c(Nc3ccccc3C(=O)NC)n2)c(OC)cc1N1CCN(C(C)=O)CC1]

A process similar as that for preparing Compound 1 was used. MS(ESI): m/z 579.22 (M+H)+.

Example 69: Preparation of 2-(2-(5-acrylamido-4-(4-isopropylpiperazin-1-yl)-2-methoxyphenylamino)-5-chloropyrimidin-4-ylamino)-N-methylbenzamide 69

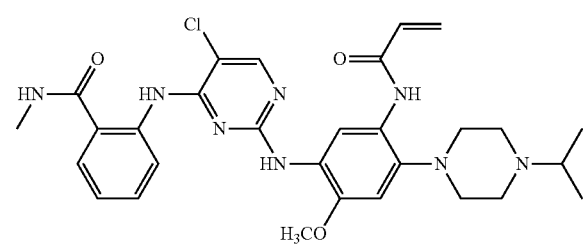

A process similar as that for preparing Compound 1 was used. MS(ESI): m/z 579.26 (M+H)+.

Example 70: Preparation of 2-(2-(5-acrylamido-4-(4-cyclohexylpiperazin-1-yl)-2-methoxyphenylamino)-5-chloropyrimidin-4-ylamino)-N-methylbenzamide 70

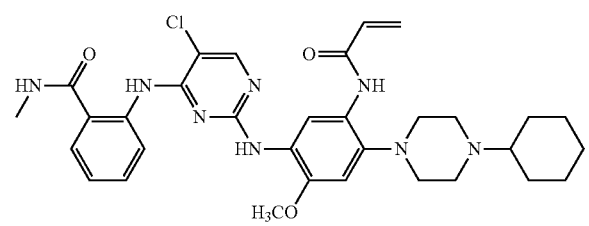 [SMILES: C=CC(=O)Nc1cc(Nc2ncc(Cl)c(Nc3ccccc3C(=O)NC)n2)c(OC)cc1N1CCN(C2CCCCC2)CC1]

A process similar as that for preparing Compound 1 was used. MS(ESI): m/z 619.29 (M+H)+.

Example 71: Preparation of 2-(2-(5-acrylamido-4-((2-(dimethylamino)ethyl)(methyl)amino)-2-methoxyphenylamino)-5-chloropyrimidin-4-ylamino)-N-methylbenzamide 71

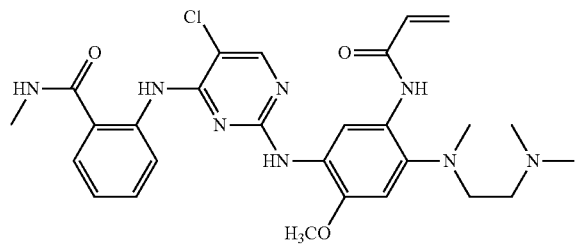

A process similar as that for preparing Compound 1 was used. MS(ESI): m/z 553.24 (M+H)+.

Example 72: Preparation of 2-(2-(5-acrylamido-2-methoxy-4-(4-(1-methylpiperidin-4-yl)piperazin-1-yl)phenylamino)-5-chloropyrimidin-4-ylamino)-N-methylbenzamide 72

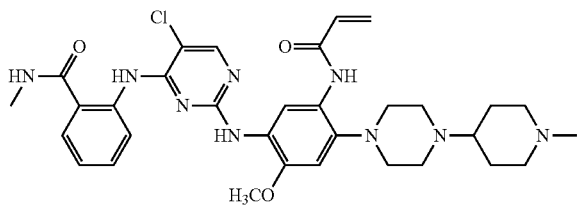

A process similar as that for preparing Compound 1 was used. MS(ESI): m/z 634.30 (M+H)+.

Example 73: Preparation of N-(5-(5-chloro-4-(2-((1-methyl-1H-imidazol-2-yl)methoxy)phenylamino)pyrimidin-2-ylamino)-4-methoxy-2-(4-methylpiperazin-1-yl)phenyl)acrylamide 73

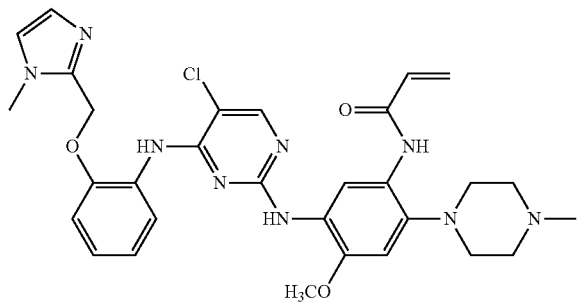

A process similar as that for preparing Compound 1 was used. MS(ESI): m/z 604.25 (M+H)+.

Example 74: Preparation of N-(5-(5-chloro-4-(2-((1-methyl-1H-imidazol-2-yl)methoxy)phenylamino)pyrimidin-2-ylamino)-2-(4-ethylpiperazin-1-yl)-4-methoxyphenyl)acrylamide 74

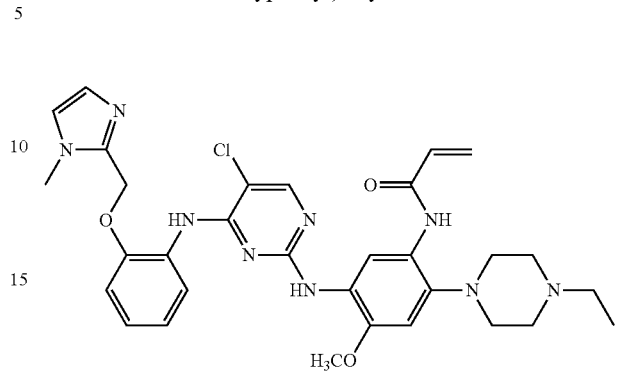

A process similar as that for preparing Compound 1 was used. MS(ESI): m/z 618.27 (M+H)+.

Example 75: Preparation of N-(2-(4-ethanoylpiperazin-1-yl)-5-(5-chloro-4-(2-((1-methyl-1H-imidazol-2-yl)methoxy)phenylamino)pyrimidin-2-ylamino)-4-methoxyphenyl)acrylamide 75

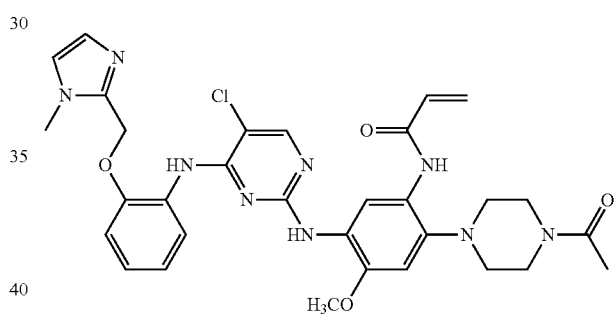

A process similar as that for preparing Compound 1 was used. MS(ESI): m/z 632.25 (M+H)+.

Example 76: Preparation of N-(5-(5-chloro-4-(2-((1-methyl-1H-imidazol-2-yl)methoxy)phenylamino)pyrimidin-2-ylamino)-4-methoxy-2-morpholinylphenyl)acrylamide 76

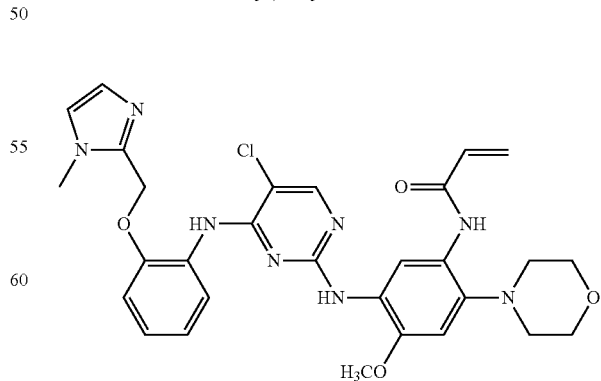

A process similar as that for preparing Compound 1 was used. MS(ESI): m/z 591.22 (M+H)+.

Example 77: Preparation of N-(5-(5-chloro-4-(2-((1-methyl-1H-imidazol-2-yl)methoxy)phenylamino)pyrimidin-2-ylamino)-2-(4-isopropylpiperazin-1-yl)4-methoxyphenyl)acrylamide 77

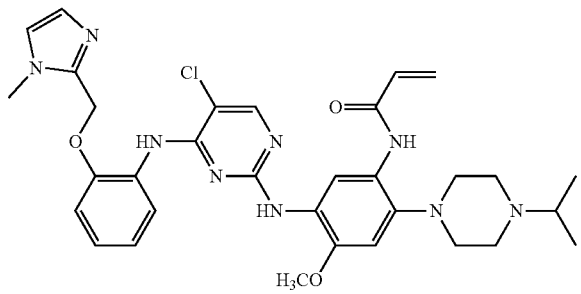 [SMILES: C=CC(=O)Nc1cc(Nc2ncc(Cl)c(Nc3ccccc3OCc3nccn3C)n2)c(OC)cc1N1CCN(C(C)C)CC1]

A process similar as that for preparing Compound 1 was used. MS(ESI): m/z 632.28 (M+H)+.

Example 78: Preparation of N-(5-(5-chloro-4-(2-((1-methyl-1H-imidazol-2-yl)methoxy)phenylamino)pyrimidin-2-ylamino)-2-(4-(dimethylamino)piperidin-1-yl)-4-methoxyphenyl)acrylamide 78

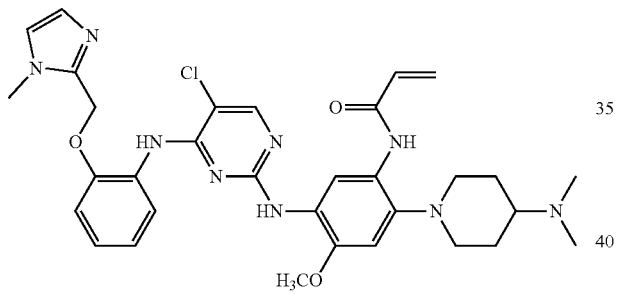

A process similar as that for preparing Compound 1 was used. MS(ESI): m/z 632.28 (M+H)+.

Example 79: Preparation of N-(5-(5-chloro-4-(2-((1-methyl-1H-imidazol-2-yl)methoxy)phenylamino)pyrimidin-2-ylamino)-4-methoxy-2-(4-(4-methylpiperazin-1-yl)piperidin-1-yl)phenyl)acrylamide 79

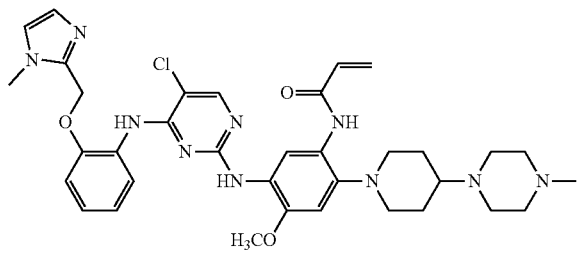

A process similar as that for preparing Compound 1 was used. MS(ESI): m/z 687.32 (M+H)+.

Example 80: Preparation of N-(5-(5-chloro-4-(2-((1-methyl-1H-imidazol-2-yl)methoxy)phenylamino)pyrimidin-2-ylamino)-4-methoxy-2-(4-morpholinylpiperidin-1-yl)phenyl)acrylamide 80

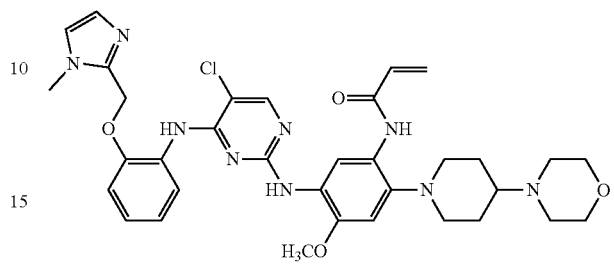

A process similar as that for preparing Compound 1 was used. MS(ESI): m/z 674.29 (M+H)+.

Example 81: Preparation of N-(5-(5-chloro-4-(2-((1-methyl-1H-imidazol-2-yl)methoxy)phenylamino)pyrimidin-2-ylamino)-2-(4-cyclohexylpiperazin-1-yl)-4-methoxyphenyl)acrylamide 81

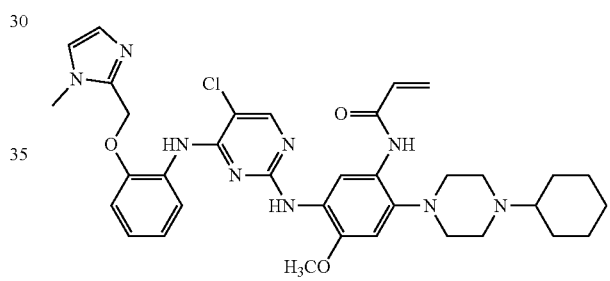

A process similar as that for preparing Compound 1 was used. MS(ESI): m/z 672.31 (M+H)+.

Example 82: Preparation of N-(2-(4-ethylpiperazin-1-yl)-5-(5-fluoro-4-(2-(isopropylsulfonyl)phenylamino)pyrimidin-2-ylamino)-4-methoxyphenyl)acrylamide 82

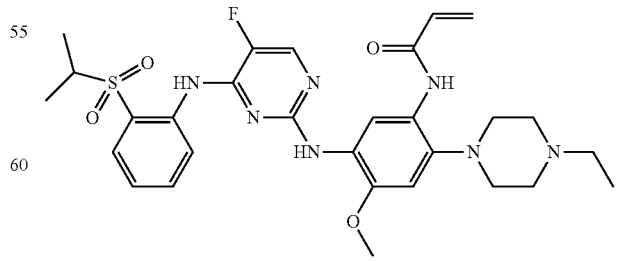

A process similar as that for preparing Compound 1 was used. MS(ESI): m/z 598.26 (M+H)+.

Example 83: Preparation of N-(5-(5-bromo-4-(2-(isopropylsulfonyl)phenylamino)pyrimidin-2-ylamino)-2-(4-ethylpiperazin-1-yl)-4-methoxyphenyl)acrylamide 83

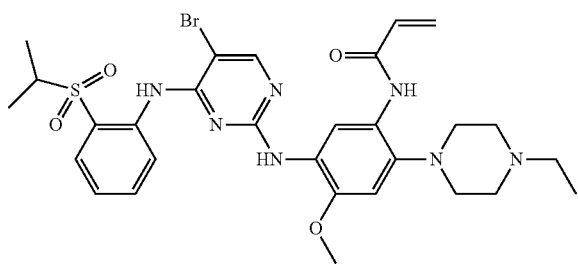 [SMILES: C=CC(=O)Nc1cc(Nc2ncc(Br)c(Nc3ccccc3S(=O)(=O)C(C)C)n2)c(OC)cc1N1CCN(CC)CC1]

A process similar as that for preparing Compound 1 was used. MS(ESI): m/z 658.18 (M+H)+.

Example 84: Preparation of N-(2-(4-ethylpiperazin-1-yl)-5-(4-(2-(isopropylsulfonyl)phenylamino)-5-methylpyrimidin-2-ylamino)-4-methoxyphenyl)acrylamide 84

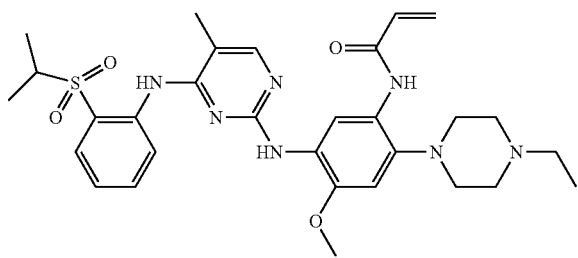 [SMILES: C=CC(=O)Nc1cc(Nc2ncc(C)c(Nc3ccccc3S(=O)(=O)C(C)C)n2)c(OC)cc1N1CCN(CC)CC1]

A process similar as that for preparing Compound 1 was used. MS(ESI): m/z 594.28 (M+H)+.

Example 85: Effect of the Novel Kinase Inhibitors on the Growth of Cancer Cells By testing the effect of the novel kinase inhibitors on the proliferation of cancer cells, the selectivity of the compounds of the present disclosure in inhibiting the proliferation of cancer cells was further assessed. In this example, human non-small cell lung cancer cell NCI-H1975 (expressing EGFR L858R/T790M double mutant gene), human skin squamous carcinoma cell A431 (expressing wild-type EGFR gene), non-small cell lung cancer NCI-H3255 (expressing EGFR L858R mutant gene), non-small cell lung cancer cell NCI-H3122 (expressing ALK gene), human non-small cell lung cancer cell A549 (expressing wild-type EGFR gene), human non-small cell lung cancer cell NCI-H2122 (expressing wild-type EGFR gene), human non-small cell lung cancer cell NCI-H460 (expressing wild-type EGFR gene), human non-small cell lung cancer cell PC-9 (expressing EGFR delE746_A750 mutant gene), Chinese hamster ovary cell CHO (*Cricetulus griseus*, hamster, Chinese, ovary), Chinese hamster lung cell CHL, human non-small cell lung cancer cell HCC827 (expressing mutant EGFR del19 gene), human lung adenocarcinoma cell HCC4006 (expressing mutant EGFR del19 gene), human non-small cell lung cancer cell NCI-H2228 (expressing wild-type ALK gene), and mouse primary B cell BaF3 were used, and the above cells were all purchased from ATCC (US). In addition, mouse BaF3-TEL-ALK (stably expressing ALK kinase), mouse BaF3-ALK-F1174L (stably expressing mutant ALK F1174L kinase), mouse BaF3-NPM-ALK (stably expressing ALK kinase), mouse BaF3-TEL-EGFR (stably expressing EGFR kinase), mouse BaF3-TEL-EGFR-T790M (stably expressing EGFR T790M mutant kinase), mouse BaF3-FL-EGFR-Del19 (stably expressing EGFR delE746_A750 mutant kinase), mouse BaF3-TEL-EGFR-L858R (stably expressing EGFR L858R mutant kinase), mouse BaF3-FL-EGFR-T790M-L858R (stably expressing EGFR T790M/L858R mutant kinase), mouse BaF3-TEL-INSR (stably expressing INSR protein), mouse BaF3-TEL-IGF1R (stably expressing IGF1R Protein), mouse BaF3-EML4-ALK (stably expressing EML4-ALK Protein), mouse BaF3-TEL-JAK3 (stably expressing JAK3 kinase protein), mouse BaF3-TEL-CSF1R (stably expressing CSF1R protein), and mouse BaF3-TEL-ALK-F1196M (stably expressing ALK F1196M mutant kinase) were also used in this example. The above cell lines were all established by our laboratory via the following process: kinase proteins or protein domain sequences of human ALK, ALK F1174L, EGFR, EGFR T790M, EGFR delE746_A750, EGFR L858, EGFR T790M/L858R, INSR, IGF1R, EML4-ALK, JAK3, CSF1R, ALK F1196M were amplified respectively by PCR, and were respectively inserted into MSCV-Puro vector (Clontech) with N-terminal TEL fragments and/or NPM fragments and/or TPR fragments; the resultants were stably transfected into mouse BaF3 cells by the means of retrovirus, and the IL-3 growth factors were removed, and eventually the ALK, ALK F1174L, EGFR, EGFR T790M, EGFR delE746_A750, EGFR L858, EGFR T790M/L858R, INSR, IGF1R, EML4-ALK, JAK3, CSF1R, ALK F1196M-transferred protein dependent cell lines were obtained.

In the example, different concentrations (0.000508 μM, 0.00152 μM, 0.00457 μM, 0.0137 μM, 0.0411 μM, 0.123 μM, 0.370 μM, 1.11 μM, 3.33 μM, 10 μM) of compounds of the present disclosure and TAE-684, WZ4002 and Crizotinib (the latter three were purchased from Shanghai Haoyuan Chemexpress Co., Ltd.) were respectively added into the above cells, and were incubated for 72 hrs. The number of viable cells was determined quantitatively by a microplate reader using Cell Titer-Glo® (Promega, US) chemiluminescence cell viability assay kit. Wherein, TAE-684 and Crizotinib are existing ALK inhibitors, WZ4002 is a drug that has been reported to inhibit EGFR/T790M mutation. The test results were shown in Table 1.

TABLE 1

Effect of the novel kinase inhibitors on the growth of cancer cells (the result was expressed as GI50 value in μM)

| Cell Lines | Compound 1 GI50(μM) | Compound 2 GI50(μM) | Compound 3 GI50(μM) | Compound 4 GI50(μM) | Compound 5 GI50(μM) | Compound 6 GI50(μM) |
|---|---|---|---|---|---|---|
| NCI-H1975 | 0.067 | 0.043 | 0.38 | 0.024 | 0.04 | 0.24 |
| PC-9 | 0.0007 | 0.005 | 0.25 | 0.045 | 0.039 | 0.027 |

TABLE 1-continued

Effect of the novel kinase inhibitors on the growth of cancer cells (the result was expressed as GI50 value in μM)

| Cell lines | | | | | | |
|---|---|---|---|---|---|---|
| A431 | 0.062 | 0.25 | 1.2 | 0.43 | 1.1 | 0.54 |
| CHO | 0.2 | 0.5 | >10 | >10 | 5.2 | 0.36 |
| CHL | 1.8 | 2 | >10 | 4.9 | 2.3 | >10 |
| NCI-H460 | | | | | | |
| NCI-H2122 | 0.009 | 3.6 | 0.71 | 1.3 | 0.17 | 0.88 |
| A549 | 0.41 | 0.87 | >10 | 2.2 | 3.3 | 0.33 |
| NCI-H3255 | | | | | | |
| HCC827 | 0.003 | 0.01 | 0.37 | 0.016 | 0.044 | 0.051 |
| HCC4006 | | | 1.1 | | 0.16 | 0.26 |
| NCI-H3122 | | 0.033 | 0.032 | 0.007 | <0.3 nM | 0.029 |
| NCI-H2228 | | 0.25 | 0.56 | 0.0074 | 0.24 | 0.2 |
| BaF3 | 1.4 | 1.6 | 4.7 | 2 | 2.8 | 0.34 |
| BaF3-TEL-ALK | <0.0003 | >10 | 0.024 | 0.008 | 0.01 | 0.015 |
| BaF3-ALK-F1174L | | 0.67 | 1.3 | 1.5 | 2.3 | 0.31 |
| BaF3-NPM-ALK | <0.0003 | | | | | |
| BaF3-TEL-EGFR | | 0.45 | | | | |
| BaF3-TEL-EGFR-T790M | 0.032 | 0.012 | 0.29 | 0.062 | 0.053 | 0.018 |
| BaF3-FL-EGFR-Del19 | <0.0003 | <0.0003 | 0.13 | 0.015 | 0.007 | 0.006 |
| BaF3-TEL-EGFR-L858R | <0.003 | | | | | |
| BaF3-FL-EGFR-T790M-L858R | | | | | | |

| Cell lines | Compound 7 GI50(μM) | Compound 8 GI50(μM) | Compound 9 GI50(μM) | Compound 10 GI50(μM) | Compound 11 GI50(μM) | Compound 13 GI50(μM) |
|---|---|---|---|---|---|---|
| NCI-H1975 | 1.2 | 0.045 | 0.059 | 0.015 | 0.025 | 0.041 |
| PC-9 | 0.09 | 0.053 | 0.043 | 0.015 | 0.024 | 0.012 |
| A431 | 0.84 | 0.37 | 0.32 | 0.17 | 0.14 | 0.47 |
| CHO | 2.9 | 0.46 | 1 | 0.99 | 1.3 | 0.47 |
| CHL | 9.1 | 0.8 | 4.3 | 3.5 | 1.1 | 3.7 |
| NCI-H460 | | 0.66 | | | | |
| NCI-H2122 | 1.03 | 0.20 | 0.68 | 0.19 | 0.19 | |
| A549 | 0.36 | | 1.3 | 0.51 | 0.21 | 0.63 |
| NCI-H3255 | | 0.11 | | | | |
| HCC827 | 0.11 | 0.0027 | 0.035 | | | 0.015 |
| HCC4006 | | 0.014 | | | | |
| NCI-H3122 | | <0.3 nM | 0.042 | <0.0003 | <0.0003 | <0.0003 |
| NCI-H2228 | 0.031 | 0.35 | 0.26 | <0.003 | <0.003 | 0.0059 |
| BaF3 | | 0.46 | 2.9 | 1.2 | 0.45 | 1.4 |
| BaF3-TEL-ALK | | <0.0003 | >10 | 0.003 | <0.003 | >10 |
| BaF3-ALK-F1174L | 0.63 | 0.029 | 0.54 | 1.5 | 0.53 | |
| BaF3-NPM-ALK | 0.001 | <0.003 | | 0.001 | <0.0003 | <0.0003 |
| BaF3-TEL-EGFR | | 0.43 | 0.65 | | | |
| BaF3-TEL-EGFR-T790M | | 0.046 | 0.047 | | | |
| BaF3-FL-EGFR-Del19 | | 0.002 | <0.0003 | | | |
| BaF3-TEL-EGFR-L858R | | | | | | |
| BaF3-FL-EGFR-T790M-L858R | | | | 0.002 | 0.002 | |

| Cell lines | Compound 14 GI50(μM) | Compound 15 GI50(μM) | Compound 16 GI50(μM) | Compound 18 GI50(μM) | Compound 21 GI50(μM) |
|---|---|---|---|---|---|
| NCI-H1975 | 0.1 | 0.077 | 0.31 | 0.26 | 0.1 |
| PC-9 | | 0.036 | 0.23 | 0.16 | 0.031 |
| A431 | 0.35 | 0.37 | 4.2 | 4.6 | 1.1 |
| CHO | 0.3 | 0.17 | 1.3 | 5.4 | 6.2 |
| CHL | 2 | 1.4 | >10 | 4.2 | >10 |
| NCI-H460 | | | | | |
| NCI-H2122 | 4.3 | | 1.1 | 3.4 | 1.4 |
| A549 | 0.13 | 0.39 | 4.5 | >10 | >10 |
| NCI-H3255 | | | | | |
| HCC827 | 0.032 | 0.038 | | 0.046 | 0.028 |
| HCC4006 | | | | | |
| NCI-H3122 | <0.0003 | <0.0003 | 0.02 | 0.77 | 0.3 |
| NCI-H2228 | 0.028 | 0.07 | 0.066 | 0.17 | 0.078 |
| BaF3 | | 0.3 | 4.1 | 4.3 | 6.8 |
| BaF3-TEL-ALK | | 0.0075 | 0.016 | 0.18 | 0.043 |
| BaF3-ALK-F1174L | | | | 1.7 | 0.74 |
| BaF3-NPM-ALK | <0.0003 | <0.0003 | 0.016 | | |
| BaF3-TEL-EGFR | | | | | |
| BaF3-TEL-EGFR-T790M | | | | 0.08 | 0.035 |
| BaF3-FL-EGFR-Del19 | | | | <0.0003 | <0.0003 |
| BaF3-TEL-EGFR-L858R | | | | | |
| BaF3-FL-EGFR-T790M-L858R | | | | | |

| Cell lines | Compound 24 GI50(μM) | Compound 28 GI50(μM) | Compound 29 GI50(μM) | Compound 30 GI50(μM) | Compound 32 GI50(μM) |
|---|---|---|---|---|---|
| NCI-H1975 | 0.059 | 0.14 | 0.12 | 0.88 | 0.031 |
| PC-9 | 0.05 | 0.071 | 0.062 | 0.053 | <0.003 |

TABLE 1-continued

Effect of the novel kinase inhibitors on the growth of cancer cells (the result was expressed as GI50 value in μM)

| Cell lines | | | | | |
|---|---|---|---|---|---|
| A431 | 0.44 | 0.071 | 0.1 | 0.84 | 0.22 |
| CHO | 1.7 | 1.7 | 1.5 | 1.9 | 0.34 |
| CHL | 0.66 | 3.3 | 3.7 | 0.73 | 1.6 |
| NCI-H460 | 0.68 | | | 0.44 | |
| NCI-H2122 | 0.23 | 0.621 | 0.68 | 0.15 | 0.37 |
| A549 | | 0.48 | 0.69 | | 0.6 |
| NCI-H3255 | 0.13 | | | 0.64 | |
| HCC827 | 0.0062 | 0.064 | 0.059 | 0.15 | <0.003 |
| HCC4006 | 0.014 | | | 0.26 | |
| NCI-H3122 | <0.3 nM | | | <0.3 nM | 0.011 |
| NCI-H2228 | 0.33 | 0.031 | 0.073 | 0.28 | 0.49 |
| BaF3 | 1.6 | | | 0.47 | 1.1 |
| BaF3-TEL-ALK | <0.0003 | | | <0.0003 | >10 |
| BaF3-ALK-F1174L | 0.016 | 1 | 0.95 | 0.073 | 0.53 |
| BaF3-NPM-ALK | 0.002 | 0.001 | 0.003 | <0.003 | |
| BaF3-TEL-EGFR | 0.81 | | | 0.41 | 0.5 |
| BaF3-TEL-EGFR-T790M | 0.1 | | | 0.23 | 0.01 |
| BaF3-FL-EGFR-Del19 | 0.002 | | | 0.12 | <0.0003 |
| BaF3-TEL-EGFR-L858R | | | | | |
| BaF3-FL-EGFR-T790M-L858R | | | | | |

| Cell lines | TAE-684 GI50(μM) | WZ4002 GI50(μM) | Crizotinib GI50(μM) |
|---|---|---|---|
| NCI-H1975 | 0.72 | 0.021 | |
| PC-9 | 0.54 | 0.027 | |
| A431 | 1.3 | 2.2 | 1 |
| CHO | | | 6.4 |
| CHL | | | 1.9 |
| NCI-H460 | 0.47 | 8.1 | |
| NCI-H2122 | 0.31 | 5.7 | |
| A549 | 1.5 | | |
| NCI-H3255 | 1.0 | 0.39 | |
| HCC827 | 0.37 | 0.0012 | |
| HCC4006 | 0.44 | 0.0072 | |
| NCI-H3122 | <0.3 nM | 3.2 | 0.073 |
| NCI-H2228 | 0.58 | 1.1 | |
| BaF3 | 1.1 | 2.2 | |
| BaF3-TEL-ALK | <0.0003 | | |
| BaF3-ALK-F1174L | 0.14 | | |
| BaF3-NPM-ALK | <0.003 | 1.4 | 0.042 |
| BaF3-TEL-EGFR | 0.56 | 1.6 | |
| BaF3-TEL-EGFR-T790M | 0.42 | 0.046 | |
| BaF3-FL-EGFR-Del19 | | | |
| BaF3-TEL-EGFR-L858R | | | |
| BaF3-FL-EGFR-T790M-L858R | | | |

| Cell lines | Compound 47 GI50(μM) | Compound 48 GI50(μM) | Compound 49 GI50(μM) | Compound 64 GI50(μM) | Compound 65 GI50(μM) |
|---|---|---|---|---|---|
| NCI-H1975 | 0.026 | 0.041 | 0.22 | 0.05 | 0.0051 |
| PC-9 | 0.005 | 0.032 | 0.12 | 0.0072 | 0.0042 |
| A549 | 1.7 | 5.3 | 8.6 | 0.37 | 0.22 |
| NCI-H3255 | 0.14 | 0.2 | 0.35 | | |
| HCC827 | <0.0003 | 0.005 | 0.015 | 0.013 | 0.013 |
| NCI-H3122 | 0.037 | 0.078 | 0.14 | 0.0044 | 0.0035 |
| NCI-H2228 | | | | | |
| BaF3 | >10 | 5.3 | >10 | 2.9 | 2.1 |
| BaF3-TEL-ALK | 0.074 | 0.19 | 0.45 | 0.01 | 0.0031 |
| BaF3-ALK-F1174L | | | | | |
| BaF3-NPM-ALK | 0.31 | 0.38 | 0.6 | | |
| BaF3-TEL-EGFR-T790M | | | | 0.028 | 0.03 |
| BaF3-TEL-INSR | 0.072 | 0.29 | 0.92 | 0.0023 | <0.0003 |
| BaF3-TEL-IGF1R | | | | 0.014 | 0.002 |
| BaF3-EML4-ALK | | | | 0.013 | 0.0086 |
| BaF3-TEL-JAK3 | | | | 0.059 | 0.045 |
| BaF3-TEL-CSF1R | | | | | |
| BaF3-TEL-ALK-F1196M | | | | | |

| Cell lines | Compound 67 GI50(μM) | Compound 68 GI50(μM) | Compound 69 GI50(μM) | Compound 70 GI50(μM) | Compound 71 GI50(μM) | Compound 72 GI50(μM) |
|---|---|---|---|---|---|---|
| NCI-H1975 | 0.014 | 0.25 | 0.079 | 0.065 | 0.012 | 0.12 |
| PC-9 | 0.0096 | 0.097 | 0.015 | 0.035 | 0.002 | 0.12 |
| A549 | 0.45 | 1.7 | | | | |
| NCI-H3255 | | | | | | |

TABLE 1-continued

Effect of the novel kinase inhibitors on the growth of cancer cells (the result was expressed as GI50 value in μM)

| | | | | | | |
|---|---|---|---|---|---|---|
| HCC827 | 0.014 | 0.083 | 0.062 | 0.14 | 0.016 | 0.21 |
| NCI-H3122 | 0.0044 | 0.012 | 0.0045 | 0.0076 | 0.0043 | 0.018 |
| NCI-H2228 | | | | | | |
| BaF3 | 5.4 | 5.7 | 1.1 | 1 | 0.94 | 1.7 |
| BaF3-TEL-ALK | 0.013 | 0.12 | | | | |
| BaF3-ALK-F1174L | | | | | | |
| BaF3-NPM-ALK | | | | | | |
| BaF3-TEL-EGFR-T790M | 0.028 | 0.25 | | | | |
| BaF3-TEL-INSR | 0.0018 | 0.014 | 0.049 | <0.0003 | 0.0084 | 0.049 |
| BaF3-TEL-IGF1R | 0.0077 | 0.041 | | | | |
| BaF3-EML4-ALK | 0.035 | 0.16 | 0.0014 | 0.0045 | 0.012 | 0.071 |
| BaF3-TEL-JAK3 | 0.11 | 0.27 | 0.037 | 0.058 | 0.009 | 0.29 |
| BaF3-TEL-CSF1R | | | 0.1 | 0.17 | 0.15 | 0.37 |
| BaF3-TEL-ALK-F1196M | | | | | | |

| Cell lines | Compound 82 GI50(μM) | Compound 83 GI50(μM) | Compound 84 GI50(μM) |
|---|---|---|---|
| NCI-H1975 | 0.048 | <0.0003 | 0.043 |
| PC-9 | 0.014 | 0.058 | 0.006 |
| A549 | | | |
| NCI-H3255 | | | |
| HCC827 | | | |
| NCI-H3122 | 0.002 | 0.002 | 0.002 |
| NCI-H2228 | | | |
| BaF3 | 3 | 0.38 | 6.6 |
| BaF3-TEL-ALK | 0.001 | 0.001 | 0.001 |
| BaF3-ALK-F1174L | | | |
| BaF3-NPM-ALK | 0.001 | <0.0003 | 0.002 |
| BaF3-TEL-EGFR-T790M | | | |
| BaF3-TEL-INSR | 0.007 | <0.0003 | 0.004 |
| BaF3-TEL-IGF1R | | | |
| BaF3-EML4-ALK | | | |
| BaF3-TEL-JAK3 | | | |
| BaF3-TEL-CSF1R | | | |
| BaF3-TEL-ALK-F1196M | 0.006 | <0.0003 | 0.002 |

The experimental results showed that the compounds of the present disclosure had a strong inhibitory effect not only on ALK, EGFR kinase proteins and ALK, EGFR mutant kinase proteins-dependent BaF3 cell lines, but also on cancer cells carrying EGFR and/or EGFR mutation and/or ALK and/or ALK mutation. These results demonstrated that the compounds of the present disclosure are dual inhibitors of EGFR and ALK.

Example 86: Effect of the Novel Kinase Inhibitors on Signaling Pathway in Cells

In four cell lines (all purchased from ATCC) including non-small cell lung cancer cell line A549 (expressing wild-type EGFR gene), non-small cell lung cancer cell line H1975 (expressing EGFR L858R/T790M double mutant gene), non-small cell lung cancer cell line H3255 (expressing EGFR L858R mutant gene) and non-small cell lung cancer cell line PC-9 (expressing EGFR delE746_A750 mutant gene), the effect of Compound 1 on EGFR or other protein kinases related to signaling pathways of EGFR such as Stat3, AKT, ErK, eIF4E, 4EBP1, P70S6K was assessed by assaying a number of cellular biochemical and functional endpoints. The above cell lines were respectively treated with different concentrations of 0 μM, 0.03 μM, 0.1 μM, 0.3 μM, 1 μM, 3 μM of Compound 1 (in DMSO), 1 μM of WZ4002 (in DMSO) and blank control (DMSO) for 4 h, and the samples were collected. The effect of Compound 1 on phosphorylation of Stat3Y705, AKT T308, AKT 5473, Erk T202/204, EGFR Y1068, P70S6K Thr389, eIF4E Ser209, Erk T202/204, 4EBP1 (Thr37/46) in these cell lines was assayed (FIGS. 1a to 1d).

Figure 1E:
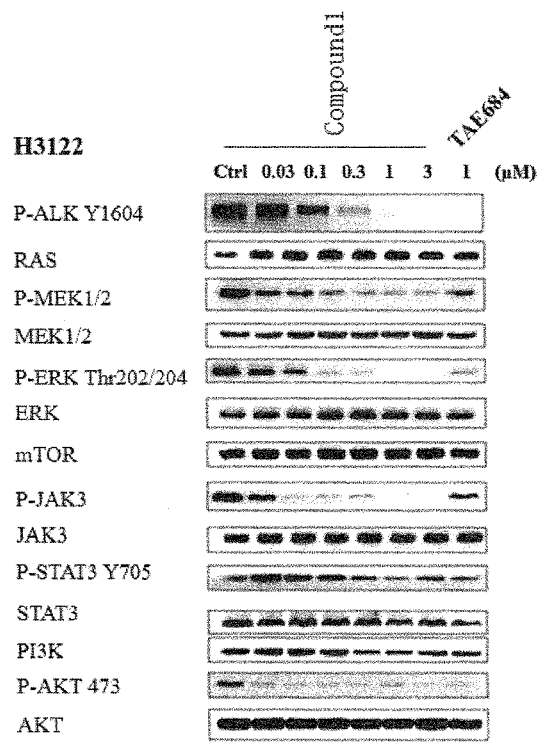

In non-small cell lung cancer cell line H3122 (expressing ALK gene), the effect of Compound 1 on other protein kinases that are closely related to ALK such as Stat3, Ras, MEK1/2, ErK, mTOR, PI3K, JAK3, AKT in this cell was assessed by assaying a number of cellular biochemical and functional endpoints. The lung cancer cell H3122 (expressing ALK gene) was treated with different concentrations of 0 μM, 0.03 μM, 0.1 μM, 0.3 μM, 1 μM, 3 μM of Compound 1 (in DMSO), 1 μM of TAE-684 (in DMSO) and blank control (DMSO) for 4 h, and the samples were collected. The effect of Compound 1 on phosphorylation of Stat3 Y705, Ras, MEK1/2S217/221, Erk T202/204, mTOR, PI3K, JAK3Tyr980/981, AKT T308, AKT 5473 in this cell line was assayed (FIG. 1e).

Figure 1F:
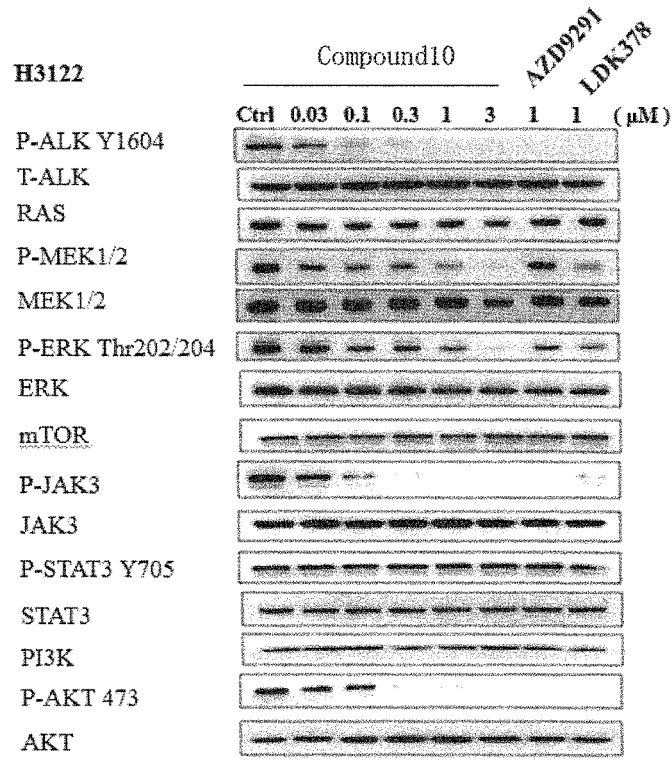
FIGS. 1f-1g illustrate the effect of Compound 10 on signaling pathways in cell lines H3122 and H1975.

In non-small cell lung cancer cell line H3122 (expressing ALK gene), the effect of Compound 10 on ALK and other protein kinases that are closely related to ALK such as Stat3, Ras, MEK1/2, ErK, mTOR, PI3K, JAK3, AKT in this cell was assessed by assaying a number of cellular biochemical and functional endpoints. The lung cancer cell H3122 (expressing ALK gene) was treated with different concentrations of 0 μM, 0.03 μM, 0.1 μM, 0.3 μM, 1 μM, 3 μM of Compound 10 (in DMSO), 1 μM of AZD9291 (in DMSO) (purchased from Shanghai Haoyuan Chemexpress Co., Ltd.), 1 μM of LDK378 (in DMSO) (purchased from Shanghai Haoyuan Chemexpress Co., Ltd.), and blank control (DMSO) for 4 h, and the samples were collected. The effect of Compound 10 on phosphorylation of ALK Y1604, Stat3 Y705, Ras, MEK1/25217/221, Erk T202/204, mTOR, PI3K, JAK3 Tyr980/981, AKT T308, AKT S473 in this cell line was assayed (FIG. 1f).

Figure 1G:
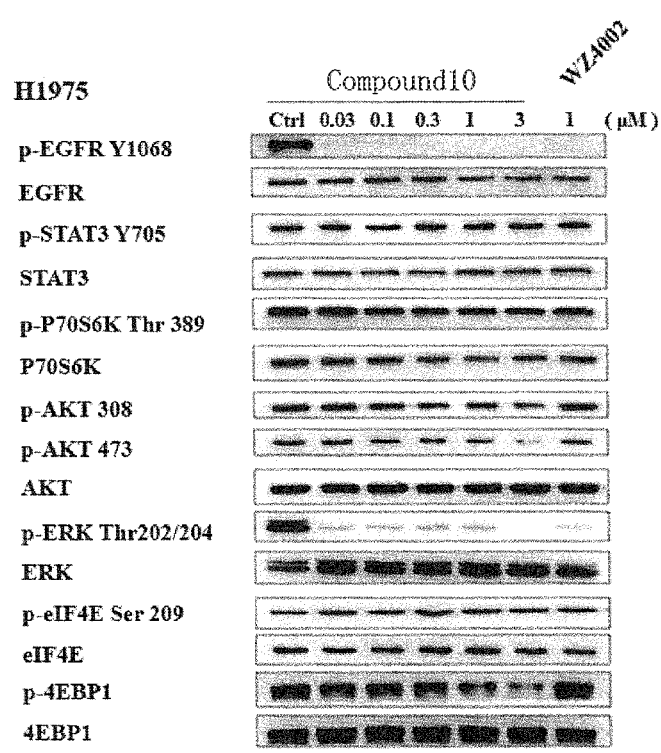
Figure 2A:
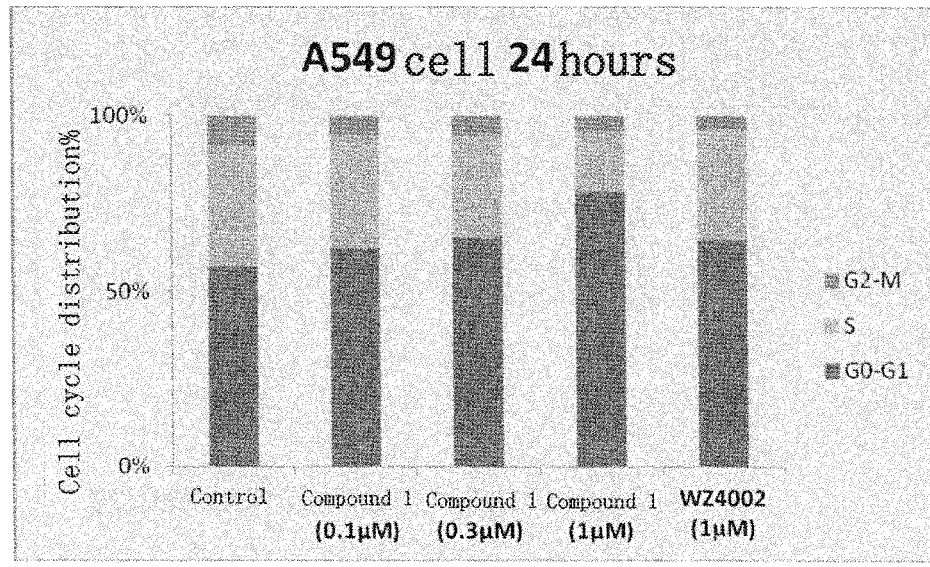
FIGS. 2a-2f illustrate the effect of Compound 1 on cell cycle in cell lines A549, H1975, PC-9, H3255 and H3122.
Figure 2B:
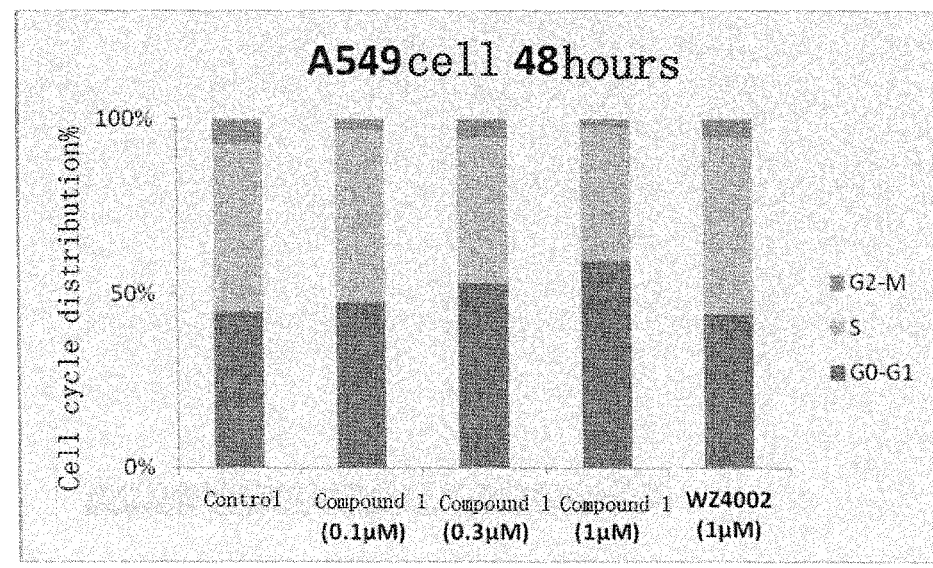
Figure 2C:
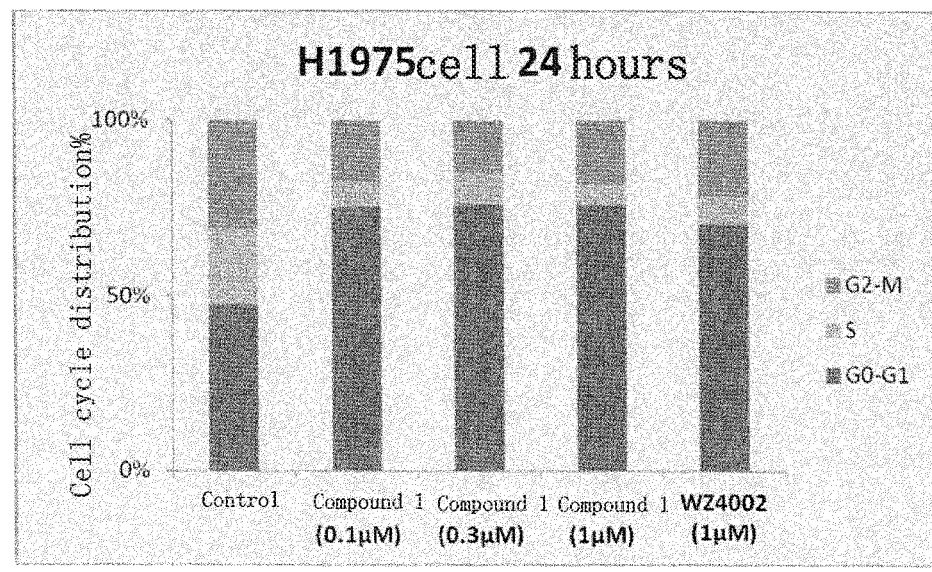
Figure 2D:
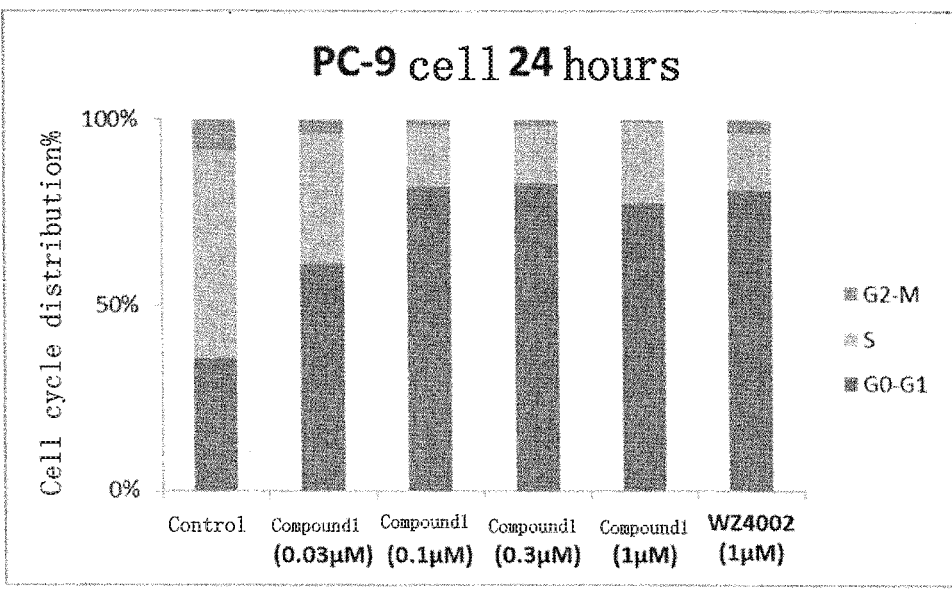
Figure 2E:
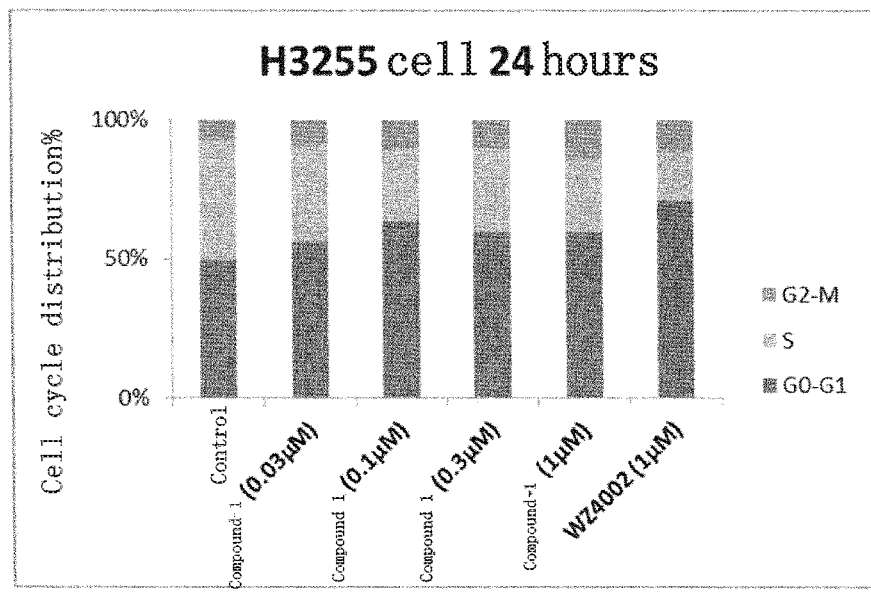
Figure 2F:
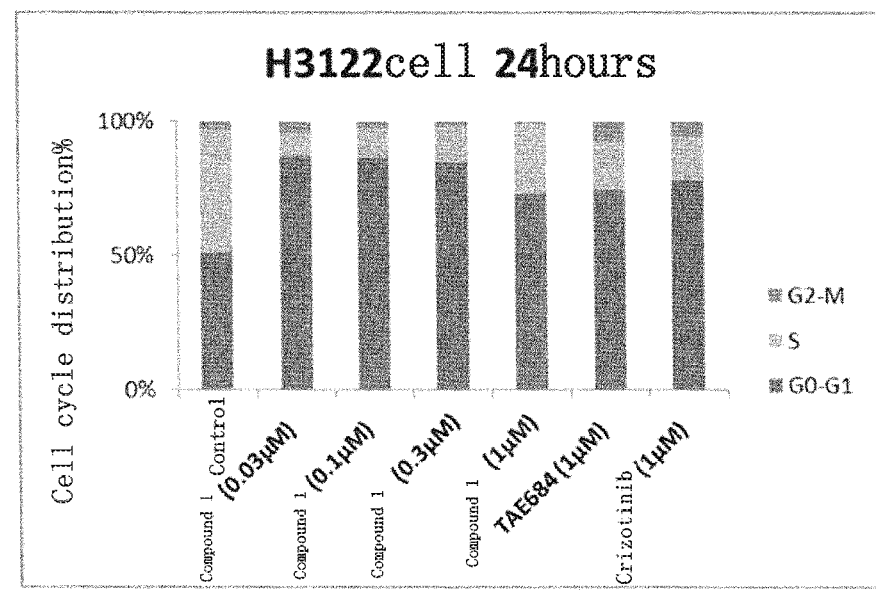
Figure 2G:
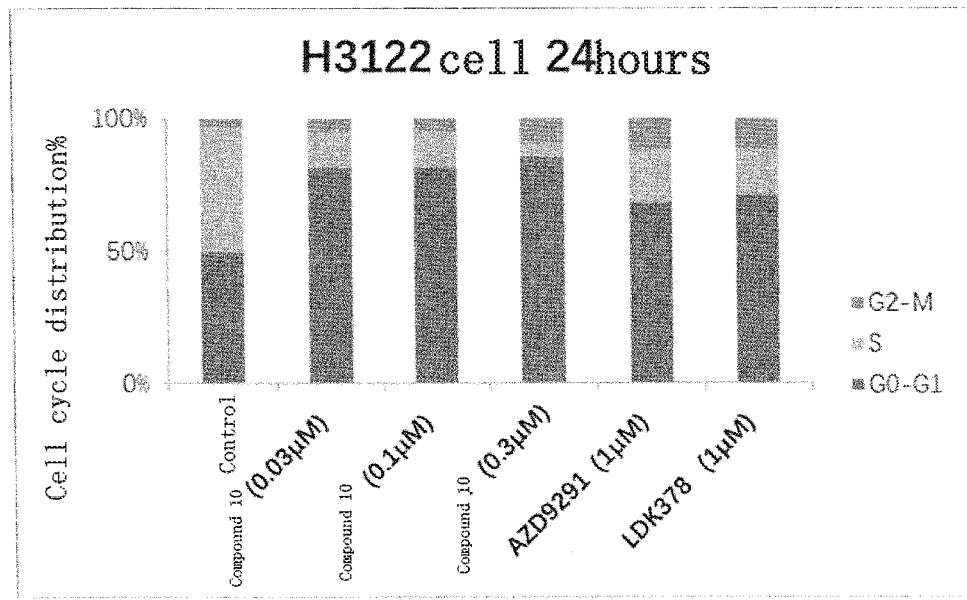
FIGS. 2g-2h illustrate the effect of Compound 10 on cell cycle in cell lines H3122 and H1975.
Figure 2H:
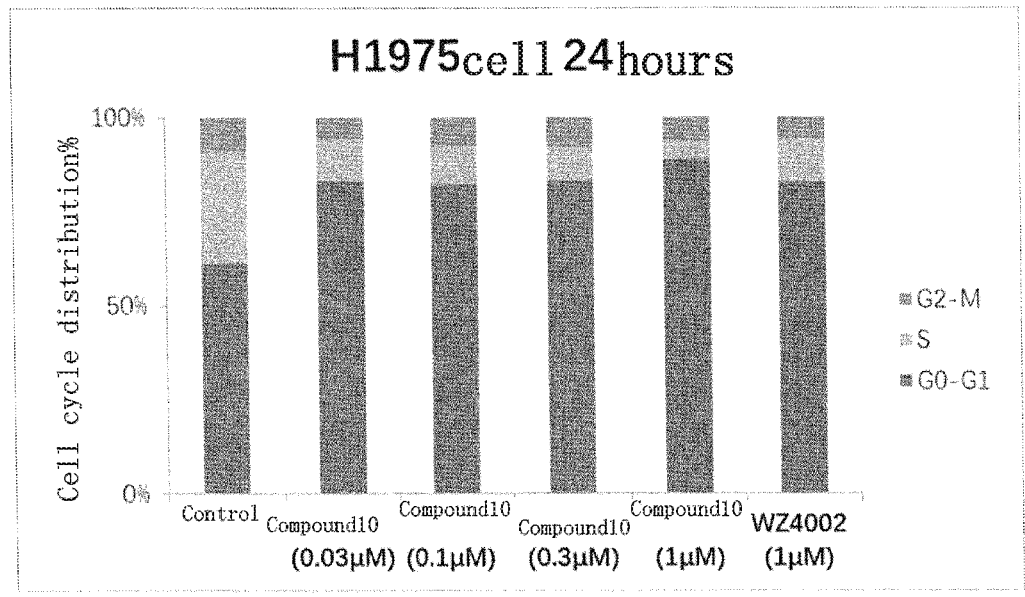

In non-small cell lung cancer cell line H1975 (expressing EGFR L858R/T790M double mutant gene), the effect of Compound 10 on EGFR and other protein kinases that are closely related to the signaling pathways of EGFR such as Stat3, AKT, ErK, eIF4E, 4EBP1, P70S6K in this cell was assessed by assaying a number of cellular biochemical and functional endpoints. This cell line was treated with different concentrations of 0 μM, 0.03 μM, 0.1 μM, 0.3 μM, 1 μM, 3 μM of Compound 10 (in DMSO), 1 μM of WZ4002 (in DMSO) and blank control (DMSO) for 4 h, and the samples were collected. The effect of Compound 10 on phosphorylation of Stat3Y705, AKT T308, AKT S473, Erk T202/204, EGFR Y1068, P70S6K Thr389, eIF4E Ser209, Erk T202/204, 4EBP1 (Thr37/46) in this cell line was assayed (FIG. 1g).

The experimental results were shown in FIG. 1. In non-small cell lung cancer cell A549 (expressing wild-type EGFR), Compound 1 has little effect not only on phosphorylation of EGFR protein, but also on phosphorylation of the proteins including STAT3, S6K, AKT, ERK, eIF4E in the related signaling pathways. The control WZ4002 behaved similarly at the concentration of 1 μM. In the non-small cell lung cancer cell line H1975 (expressing EGFR L858R/T790M double mutant gene), Compound 1 and Compound 10 were able to completely inhibit the phosphorylation of EGFR protein and also affect the phosphorylation of AKT and ERK proteins downstream of EGFR at a concentration of 0.03 μM, which behaved similarly as the drug WZ4002 reported to inhibit EGFR/T790M mutation. In non-small cell lung cancer cell line H3255 (expressing EGFR L858R mutant gene) and non-small cell lung cancer cell line PC-9 (expressing EGFR delE746_A750 mutant gene), Compound 1 was able to significantly inhibit the phosphorylation of EGFR protein and also affect phosphorylation of AKT and ERK proteins downstream of EGFR at a concentration of 0.3 μM, which behaved similarly as the drug WZ4002 reported to inhibit EGFR/T790M mutation. In non-small cell lung cancer cell line H3122 (expressing ALK gene), Compound 1 and Compound 10 were able to significantly inhibit the phosphorylation of ALK protein at concentrations of 0.1 μM and 0.03 μM, respectively, and Compound 1 and Compound 10 almost completely inhibited the phosphorylation of ALK protein at concentrations of 0.3 μM and 0.1 μM, respectively. Meanwhile, Compound 1 and Compound 10 showed evident effects on other protein kinases that are closely related to ALK protein, such as Stat3, Ras, MEK1/2, ErK, JAK3, AKT, which behaved similarly as the known ALK inhibitors TAE684, LDK378, AZD9291.

Example 87: Effect of the Novel Kinase Inhibitors on Cell Cycle

In order to study which growth phase the cell was halted after administration of the drugs, five cell lines including non-small cell lung cancer cell line A549 (expressing wild-type EGFR gene), non-small cell lung cancer cell line H1975 (expressing EGFR L858R/T790M double mutant gene), non-small cell Lung cancer cell line PC-9 (expressing EGFR delE746_A750 mutant gene), non-small cell lung cancer cell line H3255 (expressing EGFR L858R mutant gene) and non-small cell lung cancer cell NCI-H3122 (expressing ALK gene) were tested for effect of Compound 1 on cell cycle distribution. Two cell lines including non-small cell lung cancer cell NCI-H3122 (expressing ALK gene) and non-small cell lung cancer cell line H1975 (expressing EGFR L858R/T790M double mutant gene) were tested for effect of Compound 10 on cell cycle distribution. The above cell lines were treated with different concentrations (in DMSO) of Compound 1 and/or Compound 10, 1 μM (in DMSO) of mutant EGFR inhibitor AZD9291 and/or EGFR/T790M kinase inhibitor WZ4002, 1 μM (in DMSO) of ALK kinase inhibitor TAE684 and/or 1 μM (in DMSO) of ALK kinase inhibitor LDK378 and/or 1 μM (in DMSO) of ALK/MET/ROS1 kinase inhibitor Crizotinib and blank control (DMSO). After treatment of the non-small cell lung cancer cell line A549 (expressing wild-type EGFR gene) for 24 hours and 48 hours, respectively, and after treatment of the non-small cell lung cancer cell line H1975 (expressing EGFR L858R/T790M double mutant gene), non-small cell lung cancer cell line PC-9 (expressing EGFR delE746_A750 mutant gene), non-small cell lung cancer cell line H3255 (expressing EGFR L858R mutant gene) and non-small cell lung cancer cell line NCI-H3122 (expressing ALK gene) for 24 hours, the cells were harvested, washed twice with 1×PBS buffer, fixed with 75% ethanol at −20° C. for 24 hours, and washed twice again with 1×PBS buffer. 0.5 mL of 1×PBS buffer and 0.5 mL of PI staining solution (purchased from BD Bioscience, US) were added to the cells and the cells were placed lighttight in darkness at 37° C. for staining for 15 min. The cell cycle distribution was assayed by a flow Cytometer (BD FACS Calibur). The results were shown in FIG. 2

The experimental results were shown in FIG. 2. After treatment of the non-small cell lung cancer cell line A549 (expressing wild-type EGFR gene) for 24 hours and 48 hours, respectively, Compound 1 has certain effect on cell cycle of the non-small cell lung cancer cell line A549 (expressing wild-type EGFR gene). In four cell lines including non-small cell lung cancer H1975 cell line carrying EGFR L858R/T790M double mutant gene, non-small cell lung cancer cell line PC-9 carrying EGFR delE746_A750 mutant gene, non-small cell lung cancer H3255 carrying EGFR L858R mutant gene and non-small cell lung cancer NCI-H3122 carrying ALK gene, Compound 1 and/or Compound 10 were able to halt the cells in G0-G1 phase, and also it could be observed clearly that cell deaths increase as the drug concentration increases.

Example 88: Effect of the Novel Kinase Inhibitors on Cell Apoptosis

In order to confirm whether the death of cells is through apoptosis or necrosis after administration of drugs, non-small cell lung cancer cell A549 (expressing wild-type EGFR gene), non-small cell lung cancer cell line H1975 (expressing EGFR L858R/T790M double mutant gene), non-small cell lung cancer cell line H3255 (expressing EGFR L858R mutant gene), non-small cell lung cancer cell line H3122 (expressing ALK gene) cell line, and non-small cell lung cancer cell line PC-9 (expressing EGFR delE746_A750 mutant gene) were tested for effect of Compound 1 on cleavage of poly ADP-ribose polymerase PARP which is a DNA repair enzyme and Caspase 3, which were closely related to cell apoptosis. Different non-small cell lung cancer cell lines were treated with different concentrations of Compound 1 (in DMSO), 1 μM of WZ4002 (in DMSO), 1 μM (in DMSO) of TAE684, 1 μM (in DMSO) of Crizotinib, and blank control (DMSO), and were harvested after 24 hours. Western Blot was used to detect the effect of various concentrations of drugs at various time points on cleavage of poly ADP-ribose polymerase PARP which is a DNA repair enzyme and Caspase 3.

The experimental results were shown in FIG. 3. After treatment of the non-small cell lung cancer cell A549

(expressing wild-type EGFR gene) for 24 hours, cleavage of poly ADP-ribose polymerase PARP which is a DNA repair enzyme or Caspase 3 downstream of PARP was not observed. This demonstrated that Compound 1 could not cause apoptosis in non-small cell lung cancer cell A549 (expressing wild-type EGFR). However, in non-small cell lung cancer cell line H3255 (expressing EGFRL858R mutant gene) and non-small cell lung cancer cell line H3122 (expressing ALK gene), an evident cleavage of poly ADP-ribose polymerase PARP which is a DNA repair enzyme and an evident cleavage of Caspase 3 downstream of PARP could be observed when Compound 1 was administrated at a concentration of 0.03 µM. In the same experiment, in non-small cell lung cancer cell line H1975 (expressing EGFR L858R/T790M double mutant gene) and non-small cell lung cancer cell line PC-9 (expressing EGFR delE746_A750 mutant gene), an evident cleavage of poly ADP-ribose polymerase PARP which is a DNA repair enzyme and an evident cleavage of Caspase 3 downstream of PARP could be observed when Compound 1 was administrated at a concentration of 0.3 µM. This demonstrated that Compound 1 could cause apoptosis of non-small cell lung cancer cell line H1975 (expressing EGFR L858R/T790M double mutant gene), non-small cell lung cancer cell line PC-9 (expressing EGFR delE746_A750 mutant gene), non-small cell lung cancer cell line H3255 (expressing EGFR L858R mutant gene) and non-small cell lung cancer cell line H3122 (expressing ALK gene).

Figure 3A:
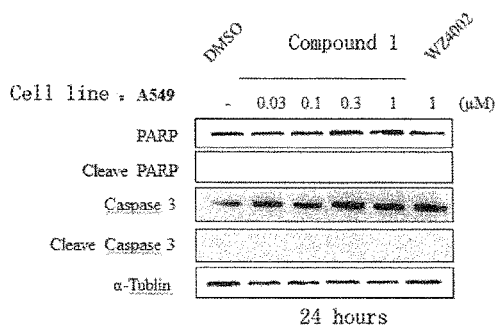
FIGS. 3a-3e illustrate the effect of Compound 1 on apoptosis in cell lines A549, H1975, H3255, H3122 and PC-9.
Figure 3B:
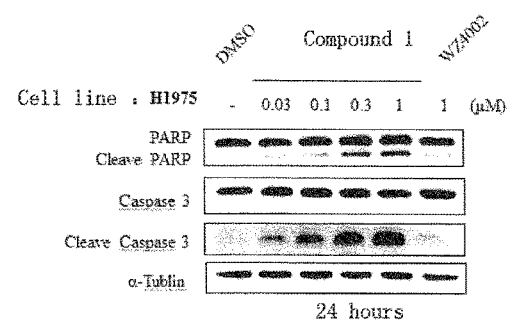
Figure 3C:
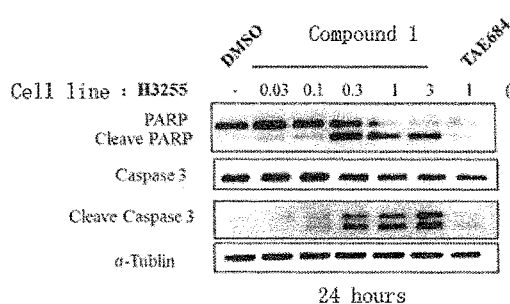
Figure 3D:
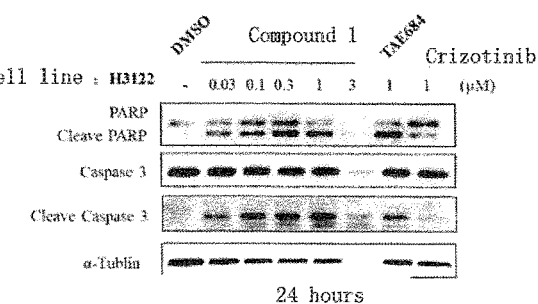
Figure 3E:
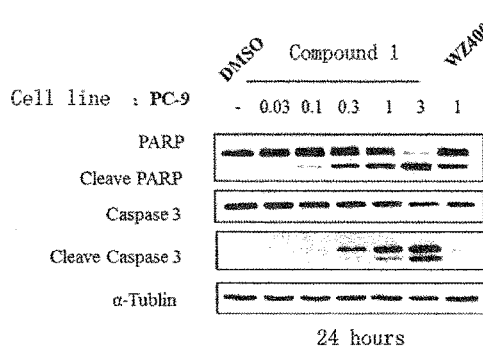
Figure 3F:
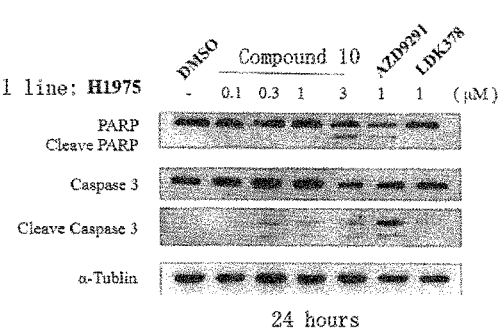
FIGS. 3f-3g illustrate the effect of Compound 10 on apoptosis in cell lines H1975 and H3122.
Figure 3G:
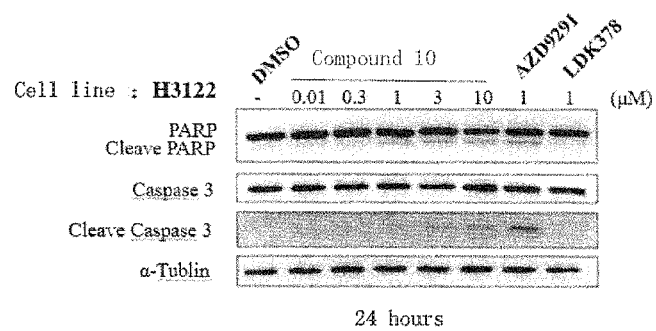

In non-small cell lung cancer cell line H1975 (expressing EGFR L858R/T790M double mutant gene), a cleavage of poly ADP-ribose polymerase PARP which is a DNA repair enzyme and a cleavage of Caspase 3 downstream of PARP could be observed when Compound 10 was administrated at a concentration of 0.3 µM (FIG. 3f). In non-small cell lung cancer cell line H3122 (expressing ALK gene), an evident cleavage of poly ADP-ribose polymerase PARP which is a DNA repair enzyme and an evident cleavage of Caspase 3 downstream of PARP could be observed when Compound 10 was administrated at a concentration of 1 µM (FIG. 3g). This demonstrated that Compound 10 could cause apoptosis of non-small cell lung cancer cell line H1975 (expressing EGFR L858R/T790M double mutant gene) and non-small cell lung cancer cell line H3122 (expressing ALK gene).

Example 89: Experimental Results of Compound 1, Compound 10 in Mouse Models of Human Non-Small Cell Lung Cancer Cell PC-9, Human Non-Small Cell Lung Cancer Cell H1975 and Human Non-Small Cell Lung Cancer Cell H3122

24 Bal b/c female mice, 4-6 weeks old, were purchased from Shanghai SLAC Laboratory Animal Co., Ltd., and maintained in an SPF laboratory. Drinking water and bedding were both sterilized by autoclaving. All operations involving the mice were performed under aseptic conditions. At day 0, $5\times10^6$ non-small cell lung cancer cells PC9 (purchased from ATCC) were injected subcutaneously into the left flank of all mice. At day 15, all mice were divided into four groups (6 mice per group), and the first group of mice were orally administered with methyl cellulose (HKI) solvent, the second group of mice were orally administered with Compound 1 at a dose of 25 mg/kg mouse weight, the third group of mice were orally administered with Compound 1 at a dose of 50 mg/kg mouse weight, and the fourth group of mice were orally administered with Compound 1 at a dose of 100 mg/kg mouse weight daily. Starting from the administration, the length/width of the subcutaneous tumor was measured daily with a vernier caliper, and the weight of the mice was recorded daily to observe the effect of Compound 1 on the body weight of the mice. The mice were sacrificed at day 36 and the subcutaneous tumors were collected. The tumors were weighed, and then the tumor tissues were used to prepare protein lysates for use. The growth trend of the subcutaneous tumor within 16-36 days was plotted, wherein the tumor volume was calculated as length×width×width/2 mm$^3$.

The experimental results were shown in FIG. 4. The results showed that the inhibitor Compound 1 of the present disclosure would affect body weight of Bal b/c mice at a high dose (100 mg/kg), and it would significantly reduce the weight of subcutaneous tumors while barely affect the body weight of the mice at a low dose (25 mg/kg), and the tumor inhibition rate could reach 89.8%, demonstrating that Compound 1 could effectively inhibit the growth of subcutaneous tumors (FIG. 4).

Experiments showed that, as shown in FIG. 4, when Compound 1 was administrated to the mouse tumor model of non-small cell lung cancer cell PC-9 (expressing EGFR delE746_A750 mutant gene) at a dose of 25 mg/kg, the effect was very significant after 4 days of administration, and the tumor was completely inhibited, the body weight did not decrease and the tumor inhibition rate reached 89.8% after 8 days of administration. When administrated at a dose of 50 mg/kg, the effect was very significant after 4 days of administration, and the tumor was completely inhibited, the body weight did not decrease and the tumor inhibition rate reached 95.1% after 8 days of administration. When administrated at a dose of 100 mg/kg, the effect was very significant on the second day of administration, and the tumor was completely inhibited, the body weight did not significantly decrease and the tumor inhibition rate reached 98.7% after 8 days of administration.

Similarly, 27 Bal b/c female mice, 4-6 weeks old, were purchased from Shanghai SLAC Laboratory Animal Co., Ltd., and maintained in an SPF laboratory. Drinking water and bedding were both sterilized by autoclaving. All operations involving the mice were performed under aseptic conditions. At day 0, $5\times10^6$ non-small cell lung cancer cells H1975 (purchased from ATCC) were injected subcutaneously into the left flank of all mice. At day 15, all mice were divided into three groups (9 mice per group), and the first group of mice were orally administered with methyl cellulose (HKI) solvent, the second group of mice were orally administered with Compound 1 at a dose of 25 mg/kg mouse weight, and the third group of mice were orally administered with Compound 1 at a dose of 50 mg/kg mouse weight daily. Starting from the administration, the length/width of the subcutaneous tumor was measured daily with a vernier caliper, and the weight of the mice was recorded daily to observe the effect of Compound 1 on the body weight of the mice. The mice were sacrificed at day 36 and the subcutaneous tumors were collected. The tumors were weighed, and then the tumor tissues were used to prepare protein lysates for use. The growth trend of the subcutaneous tumor within 16-36 days was plotted, wherein the tumor volume was calculated as length×width×width/2 mm$^3$.

Experiments showed that, as shown in FIG. 5, when Compound 1 was administrated to the mouse tumor model of non-small cell lung cancer cell H1975 (expressing EGFR L858R/T790M double mutant gene) at a dose of 25 mg/kg, the effect was very significant, the body weight did not decrease and the tumor inhibition rate reached 70% on the second day of administration. When administrated at a dose of 50 mg/kg, the effect was very significant after 4 days of administration, and the tumor was completely inhibited, the body weight did not decrease and the tumor inhibition rate reached 81.7% after 8 days of administration.

Similarly, 72 Bal b/c female mice, 4-6 weeks old, were purchased from Shanghai SLAC Laboratory Animal Co., Ltd., and maintained in an SPF laboratory. Drinking water and bedding were both sterilized by autoclaving. All operations involving the mice were performed under aseptic conditions. At day 0, $5\times10^6$ non-small cell lung cancer cells H3122 (purchased from ATCC) were injected subcutaneously into the left flank of all mice. At day 15, all mice were divided into eight groups (9 mice per group), and the first group of mice were orally administered with methyl cellulose (HKI) solvent, the second group of mice were orally administered with Compound 1 at a dose of 5 mg/kg mouse weight, the third group of mice were orally administered with Compound 1 at a dose of 10 mg/kg mouse weight, the fourth group of mice were orally administered with Compound 1 at a dose of 20 mg/kg mouse weight, the fifth group of mice were orally administered with methyl cellulose (HKI) solvent, the sixth group of mice were orally administered with Compound 10 at a dose of 10 mg/kg mouse weight, the seventh group of mice were orally administered with Compound 10 at a dose of 20 mg/kg mouse weight, and the eighth group of mice were orally administered with Compound 10 at a dose of 40 mg/kg mouse weight daily. Starting from the administration, the length/width of the subcutaneous tumor was measured daily with a vernier caliper, and the weight of the mice was recorded daily to observe the effect of Compounds 1 and 10 on the body weight of the mice. For the first to fourth groups, the mice were sacrificed at day 36 and the subcutaneous tumors were collected. The tumors were weighed, and then the tumor tissues were used to prepare protein lysates for use. The growth trend of the subcutaneous tumor within 16-36 days was plotted, wherein the tumor volume was calculated as length×width×width/2 mm³. For the fifth to eighth groups, the mice were sacrificed at day 43 and the subcutaneous tumors were collected. The tumors were weighed, and then the tumor tissues were used to prepare protein lysates for use. The growth trend of the subcutaneous tumor within 16-43 days was plotted, wherein the tumor volume was calculated as length×width×width/2 mm³.

The experiments showed that, when Compound 1 was administrated to the mouse tumor model of non-small cell lung cancer cell H3122 (expressing ALK gene) at a dose of 10 mg/kg, the effect was very significant, the body weight did not decrease and the tumor inhibition rate reached 61.5% on the second day of administration (as shown in FIG. 6). When Compound 1 was administrated at a dose of 20 mg/kg, the tumor inhibition rate reached 77.7% (as shown in FIG. 6). When Compound 10 was administrated at a dose of 20 mg/kg, the body weight did not decrease and the tumor inhibition rate reached 68.3% (as shown in FIG. 7). When Compound 10 was administrated at a dose of 40 mg/kg, the body weight did not decrease and the tumor inhibition rate reached 78.4% (as shown in FIG. 7).

INDUSTRIAL APPLICABILITY

The invention provides an inhibitor of tyrosine kinase, which can be used for inhibiting the activity of tyrosine kinase or treating a disease, disorder, or condition, which would benefit from inhibition of tyrosine kinase. Therefore, it can be prepared as corresponding medicament and has industrial applicability.

While the invention has been described in detail herein, the invention is not limited thereto and modifications may be made by those skilled in the art based on the principles of the invention, and thus, all modifications in accordance with the principles of the invention are to be understood as within the protection scope of the invention.

What is claimed is:
1. A compound of formula (I), or a pharmaceutically acceptable salt, solvate, ester, acid, metabolite or prodrug thereof:

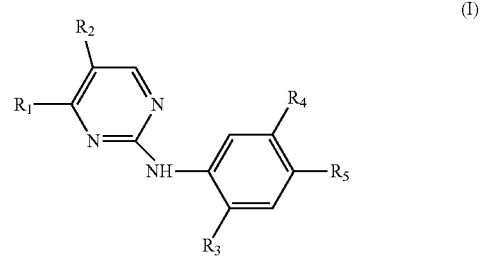

wherein:
$R_1$ is selected from the group consisting of H,

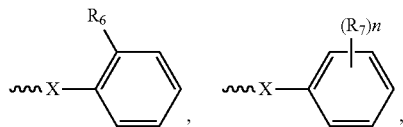

and —X—$C_{1-6}$ alkylene-heteroaryl, wherein X is selected from the group consisting of —O—, —NH—, and —N($C_{1-6}$ alkyl)-, and n=1, 2 or 3;

$R_2$ is selected from the group consisting of halogen, $C_{1-6}$ alkyl, $C_{1-6}$ haloalkyl, $C_{1-6}$ alkoxy, nitro, amino, cyano, and hydroxy;

$R_3$ is selected from the group consisting of H, $C_{1-6}$ alkoxy, $C_{1-6}$ haloalkoxy, and $C_{1-6}$ thioalkoxy;

$R_4$ is selected from the group consisting of —NH—(CO)—$C_{1-6}$ alkyl, and —NH—(CO)—$C_{2-6}$ alkenyl;

$R_5$ is selected from the group consisting of

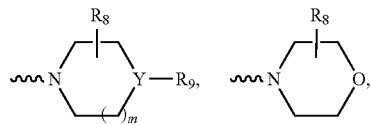

heteroaryl, —O— heteroaryl, —O—$C_{1-6}$ alkylene-$C_{1-6}$ alkylamino, —O—$C_{1-6}$ alkylene-heterocyclyl, and $C_{1-6}$ alkylamino substituted with $C_{1-6}$ alkylamino, wherein Y is selected from the group consisting of CH and N, and m=1 or 2;

$R_6$ is selected from the group consisting of H, cyano, —(SO$_2$)—$C_{1-6}$ alkyl, —(SO$_2$)—$C_{1-6}$ alkylamino, —(CO)—NH—$C_{1-6}$ alkyl, and heteroarylalkoxy in which the heteroatom is optionally substituted with $C_{1-6}$ alkyl;

$R_7$ are each independently selected from the group consisting of H, halogen, $C_{1-6}$ alkyl, $C_{1-6}$ haloalkyl, $C_{1-6}$ alkoxy, nitro, amino, cyano, hydroxy, and —NH-(amino-protecting group);

R$_8$ is selected from the group consisting of H, C$_{1-6}$ alkyl, halogen, C$_{1-6}$ haloalkyl, C$_{1-6}$ alkoxy, nitro, amino, cyano and hydroxy;

R$_9$ is selected from the group consisting of H, C$_{1-6}$ alkyl, C$_{1-6}$ haloalkyl, amino-protecting groups, C$_{1-6}$ alkoxy C$_{1-6}$ alkyl, C$_{3-8}$ cycloalkyl, C$_{1-6}$ alkylamino, C$_{4-8}$ cycloalkylalkyl, aryl C$_{1-6}$ alkyl, heterocyclyl in which the heteroatom is optionally substituted with C$_{1-6}$ alkyl or C$_{1-6}$ alkylsulfonyl, C$_{1-6}$ alkylsulfonyl, and C$_{2-6}$ alkanoyl;

the amino-protecting groups are each independently selected from the group consisting of pivaloyl, tert-butyloxycarbonyl, benzyloxycarbonyl, 9-fluorenylmethyloxycarbonyl, benzyl and p-methoxyphenyl.

2. The compound or a pharmaceutically acceptable salt, solvate, ester, acid, metabolite or prodrug thereof of claim 1, wherein R$_1$ is

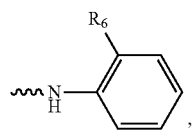

and R$_6$ is selected from the group consisting of

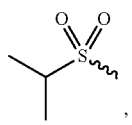

and methylaminoacyl.

3. The compound or a pharmaceutically acceptable salt, solvate, ester, acid, metabolite or prodrug thereof of claim 1, wherein R$_2$ is selected from the group consisting of fluorine, chlorine, bromine and methyl.

4. The compound or a pharmaceutically acceptable salt, solvate, ester, acid, metabolite or prodrug thereof of claim 1, wherein R$_3$ is methoxy.

5. The compound or a pharmaceutically acceptable salt, solvate, ester, acid, metabolite or prodrug thereof of claim 1, wherein R$_4$ is

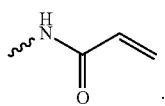

6. The compound or a pharmaceutically acceptable salt, solvate, ester, acid, metabolite or prodrug thereof of claim 1, wherein R$_5$ is

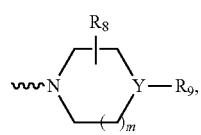

and Y is selected from the group consisting of CH and N, m=1 or 2; wherein, R$_8$ is selected from the group consisting of H and methyl; R$_9$ is selected from the group consisting of H, C$_{1-6}$ alkyl, methoxyethyl, cyclohexyl, N-morpholinyl, and methylsulfonyl.

7. The compound or a pharmaceutically acceptable salt, solvate, ester, acid, metabolite or prodrug thereof of claim 1, which is selected from the group consisting of:

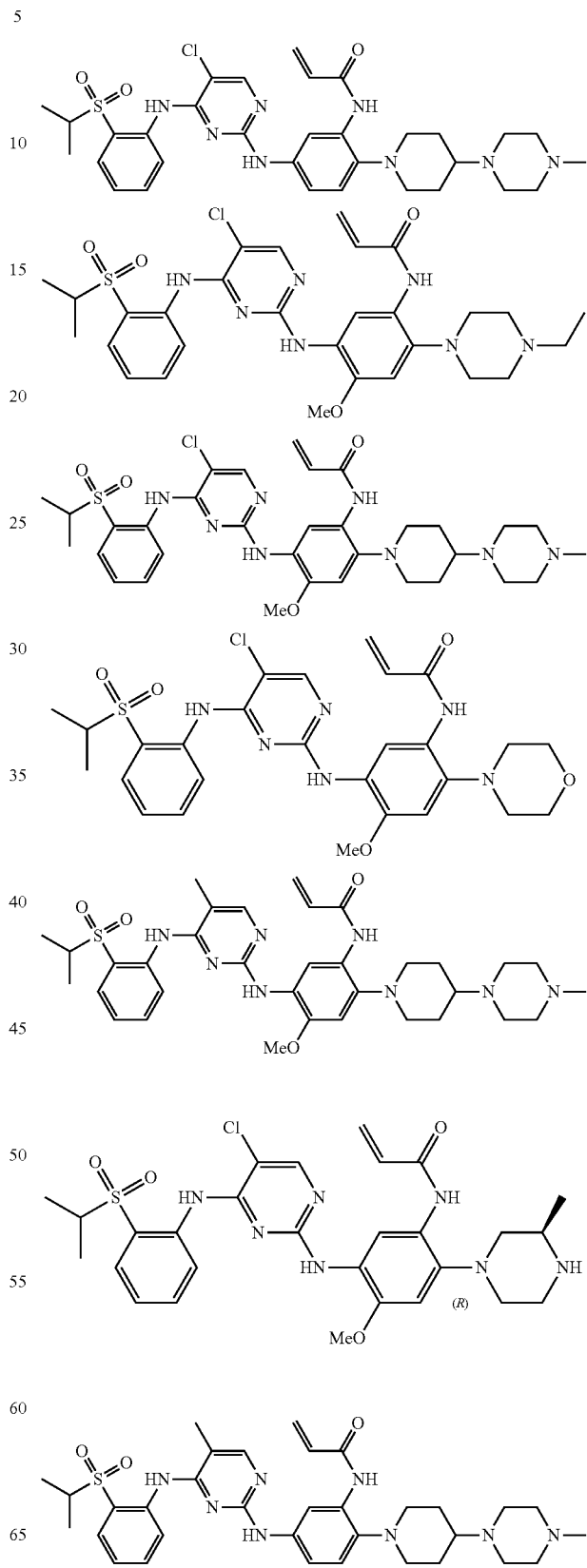

-continued
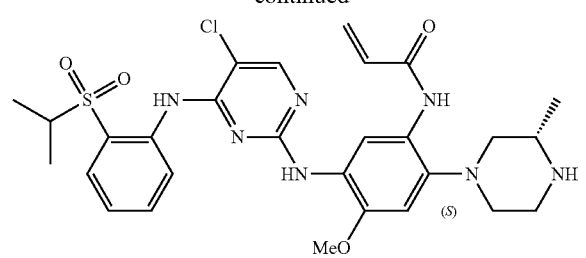
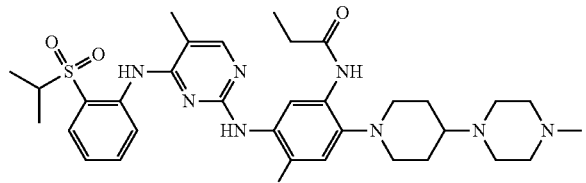
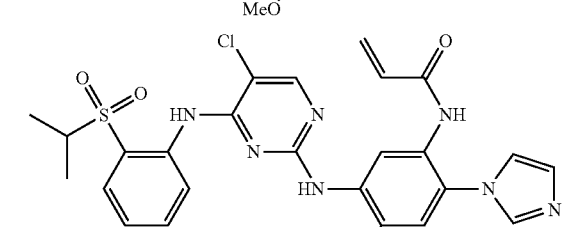
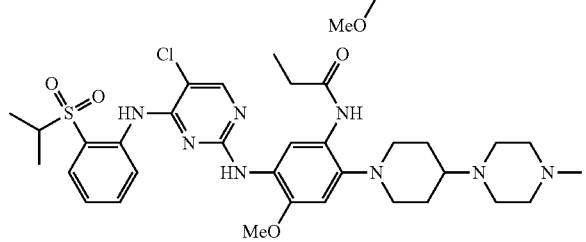
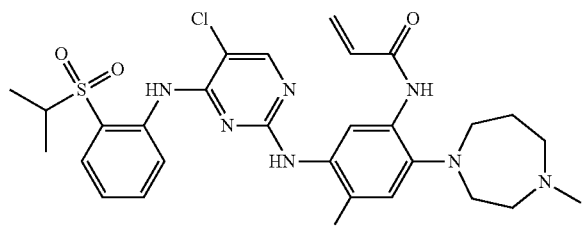
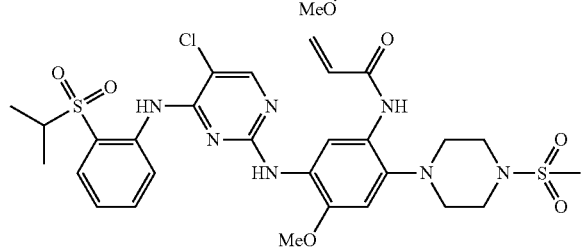
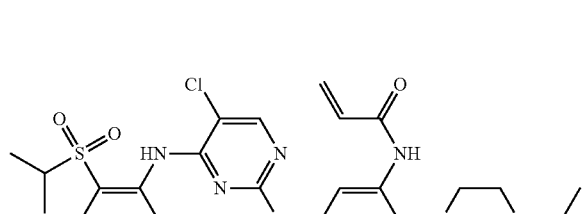
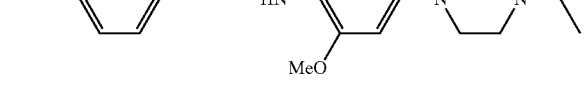
-continued
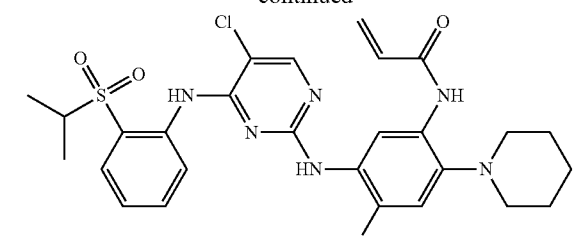
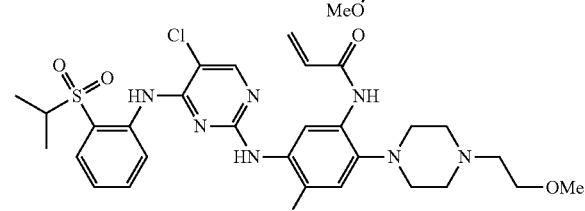
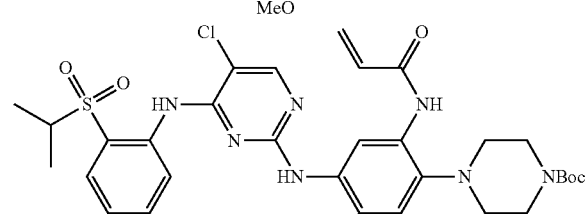
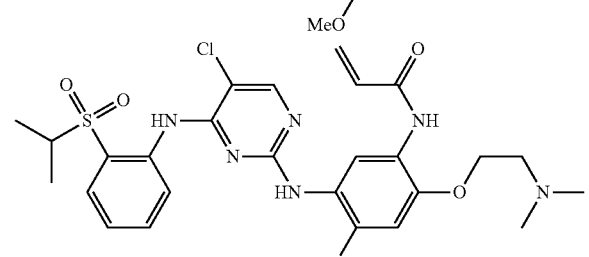
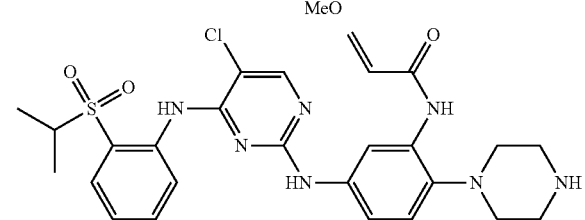
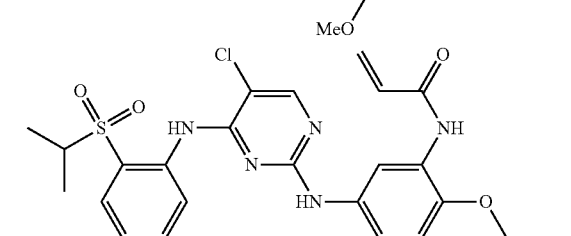
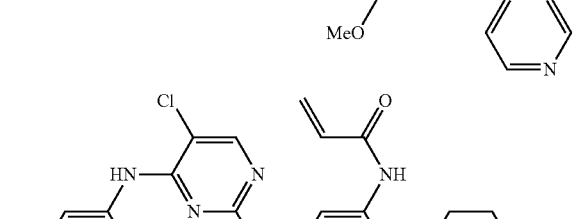
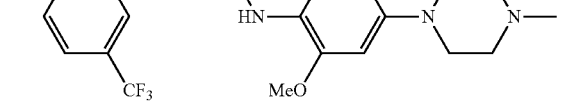

-continued

71
-continued
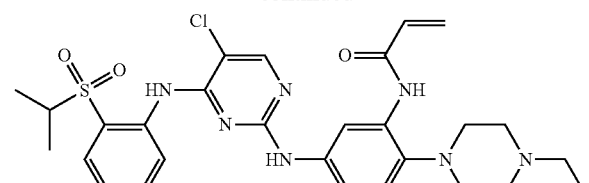
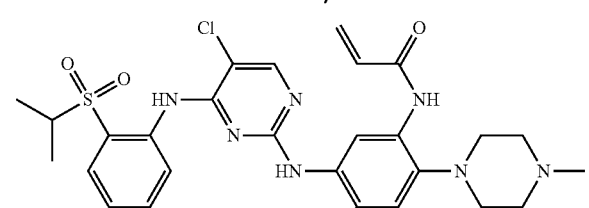
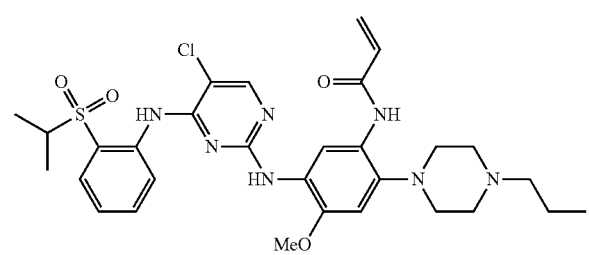
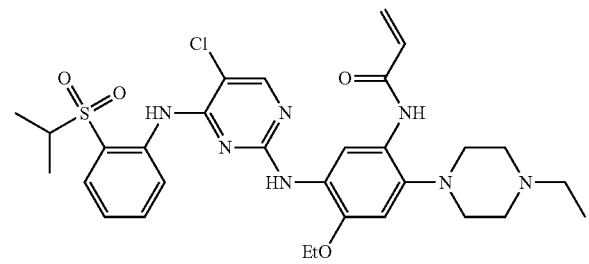
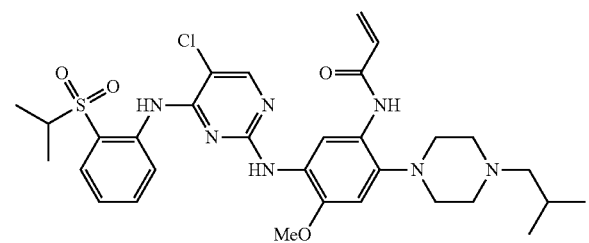
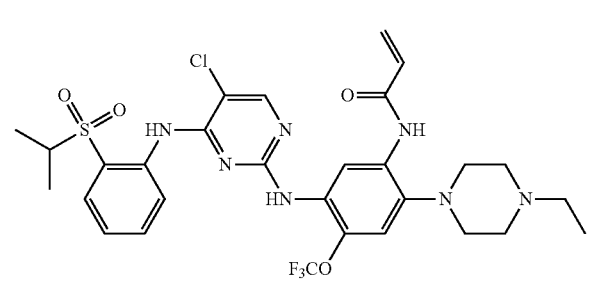
72
-continued
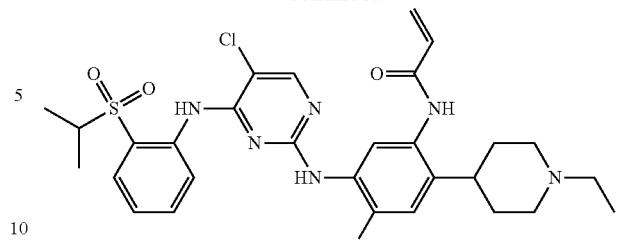
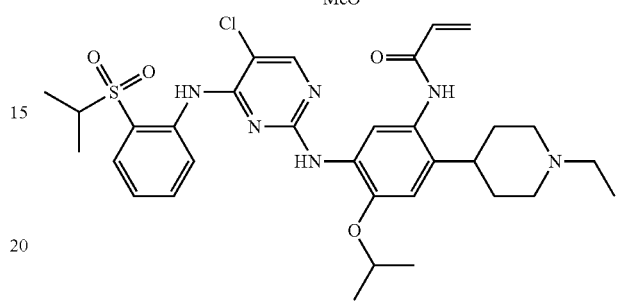
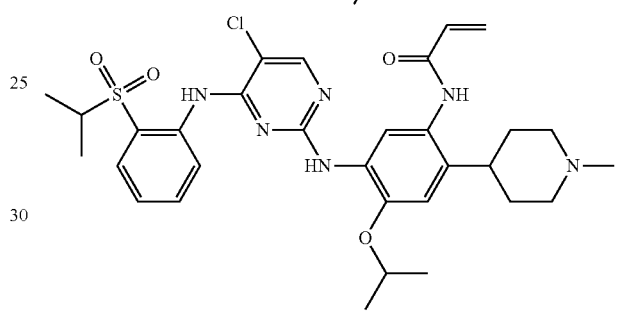
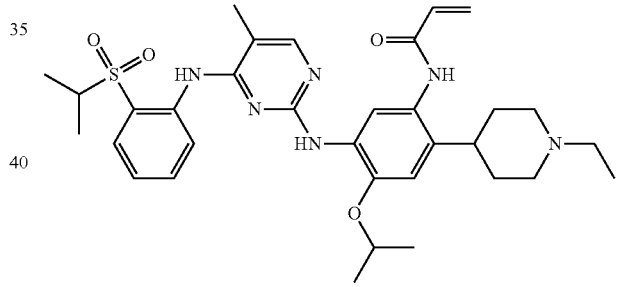
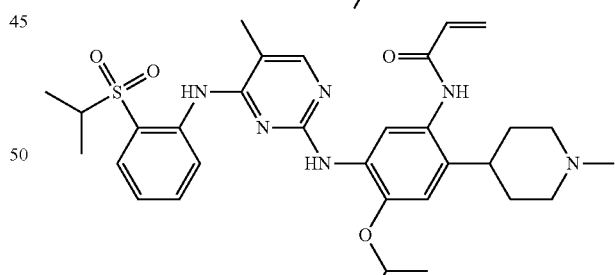
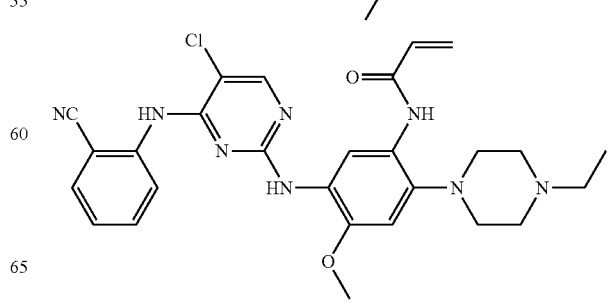

73
-continued
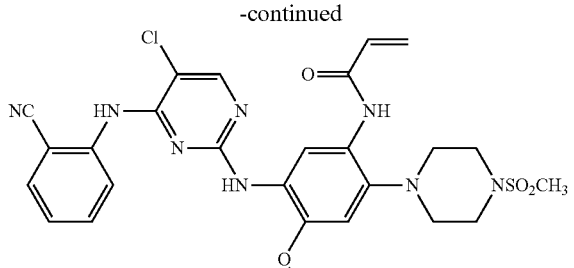
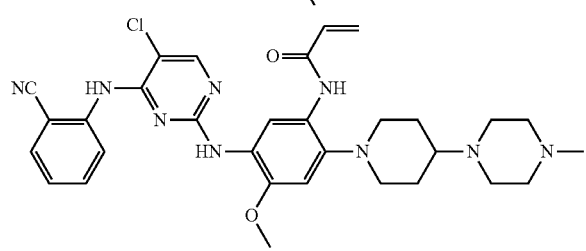
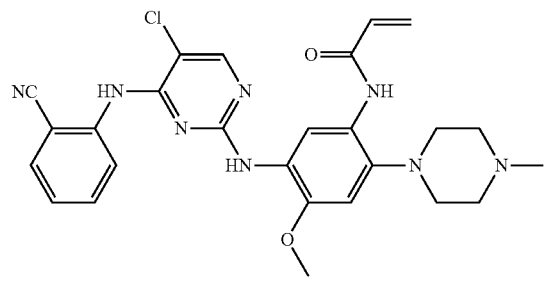
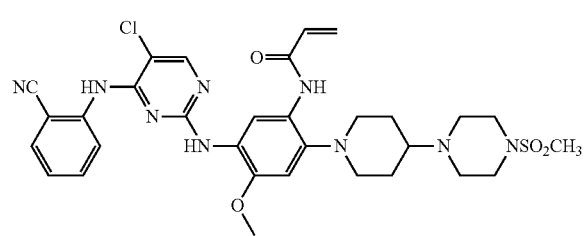
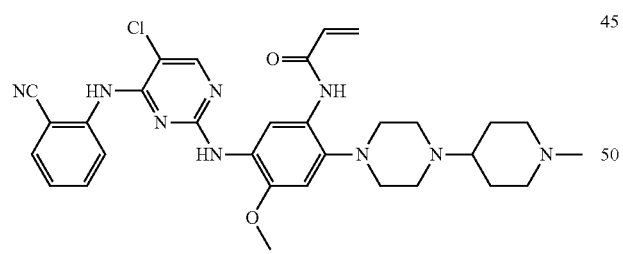
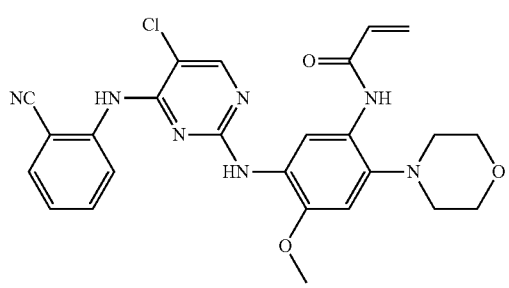
74
-continued
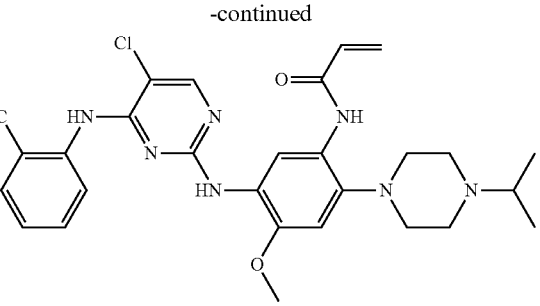
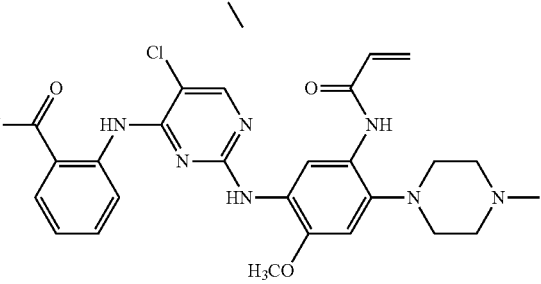
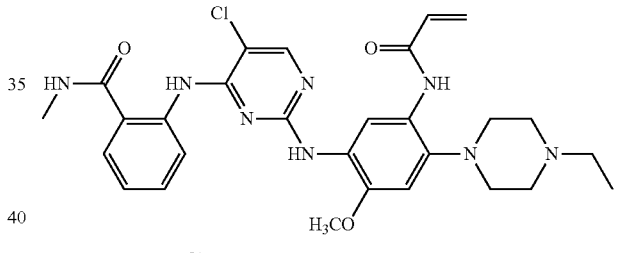
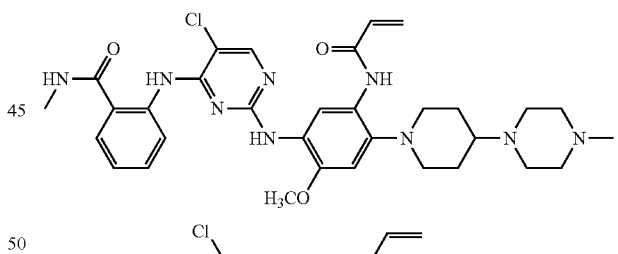
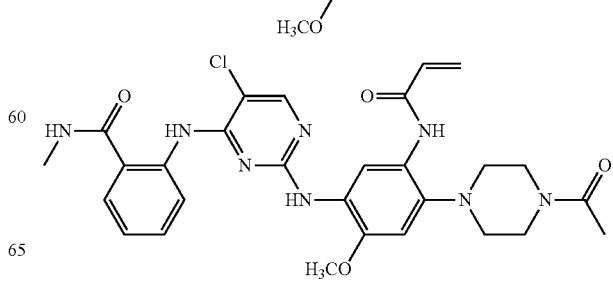

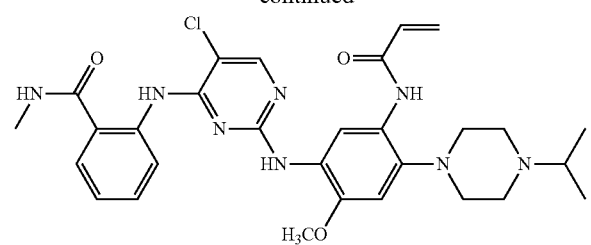
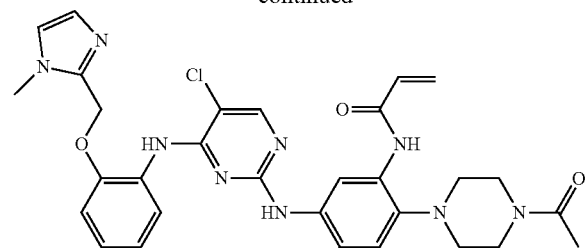
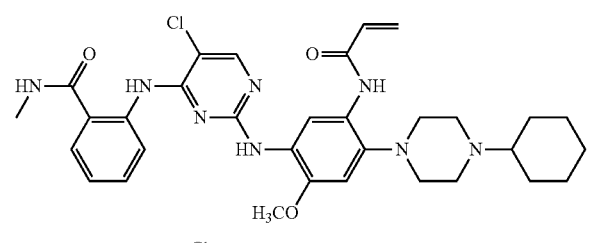
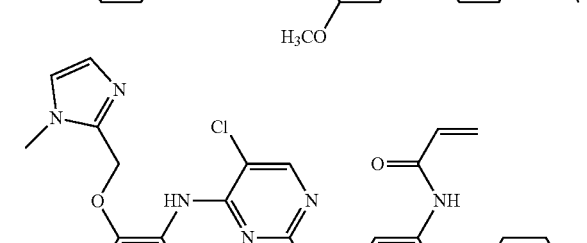
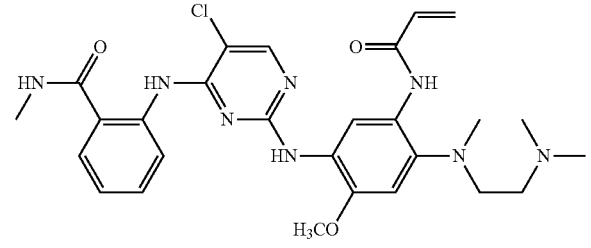
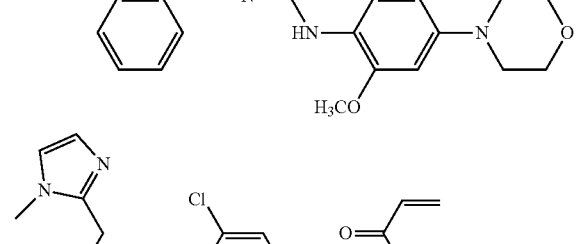
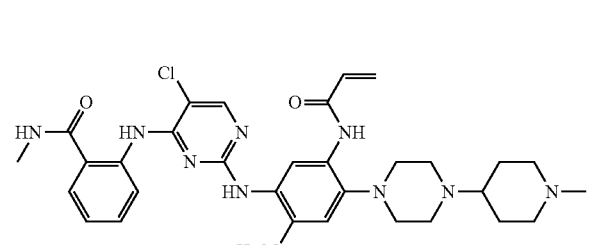
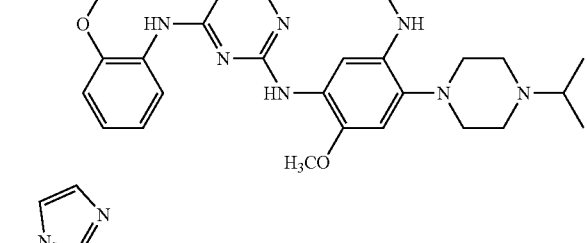
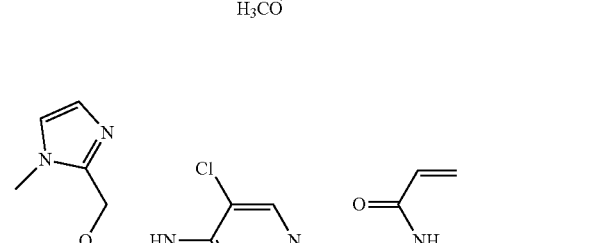
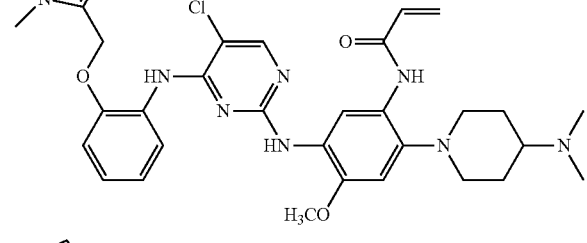
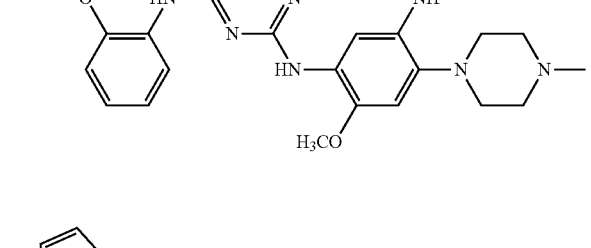
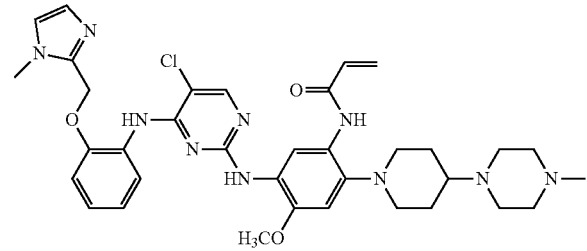
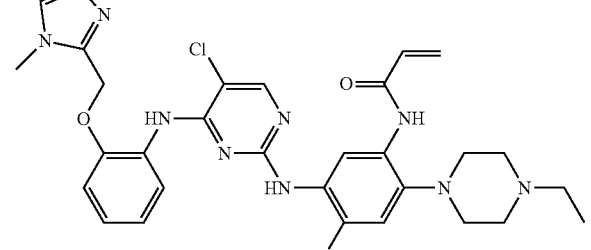
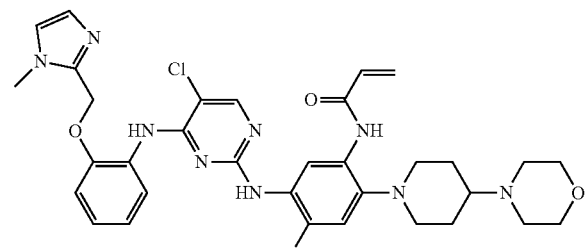

-continued

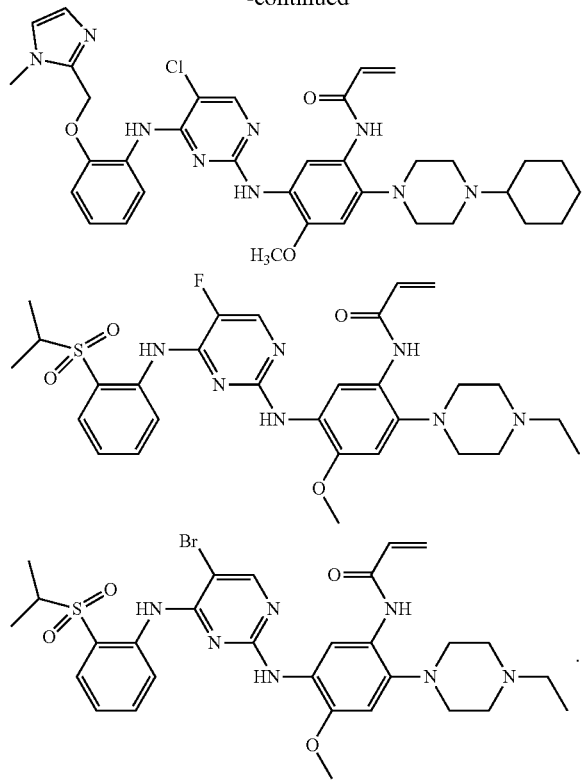

8. A method for inhibiting activity of tyrosine kinase, comprising administering the compound or a pharmaceutically acceptable salt, solvate, ester, acid, metabolite or prodrug thereof of claim 1 to a subject in need thereof, wherein the tyrosine kinase is selected from the group consisting of wild-type EGFR or various mutant EGFR or a combination thereof, and/or wild-type ALK or various mutant ALK or a combination thereof.

9. The method of claim 8, wherein the mutant EGFR is one or more selected from the group consisting of EGFR T790M mutation, EGFR L858R mutation, and EGFR delE746_A750 mutation, and the mutant ALK is one or more selected from the group consisting of ALK F1174L mutation, ALK F1196M mutation, EML4-ALK mutation, and NPM-ALK mutation.

10. A method for treating or ameliorating diseases, disorders or conditions regulated by tyrosine kinase activity or affected by tyrosine kinase activity or involving tyrosine kinase activity, comprising administering the compound or a pharmaceutically acceptable salt, solvate, ester, acid, metabolite or prodrug thereof of claim 1 to a subject in need thereof, wherein the diseases, disorders or conditions are one or more proliferative diseases selected from the group consisting of non-small cell lung cancer, small cell lung cancer, lung adenocarcinoma, lung squamous carcinoma, pancreatic cancer, prostate cancer, bladder cancer, liver cancer, skin cancer, glioma, breast cancer, melanoma, glioblastoma, rhabdomyosarcoma, ovarian cancer, astrocytoma, Ewing's sarcoma, retinoblastoma, epithelial cell carcinoma, colon cancer, kidney cancer, gastrointestinal stromal tumor, leukemia, lymphoma, and nasopharyngeal carcinoma.

11. The method of claim 10, wherein the diseases, disorders or conditions carry EGFR wild-type gene or EGFR mutant gene.

12. The method of claim 11, wherein the EGFR mutant gene is selected from the group consisting of EGFR T790M mutant gene and/or EGFR L858R mutant gene and/or EGFR delE746_A750 mutant gene.

13. The method of claim 11, wherein the diseases, disorders or conditions are drug-resistant non-small cell lung cancer that carries EGFR T790M mutant gene and/or EGFR L858R mutant gene and/or EGFR delE746_A750 mutant gene.

14. The method of claim 10, wherein the diseases, disorders or conditions carry ALK wild-type gene or ALK mutant gene.

15. The method of claim 14, wherein the ALK mutant gene is selected from the group consisting of ALK F1174L mutant gene and/or ALK F1196M mutant gene and/or EML4-ALK mutant gene and/or NPM-ALK mutant gene.

16. The method of claim 14, wherein the diseases, disorders or conditions are non-small cell lung cancer that carries ALK wild-type gene, or carries ALK F1174L mutant gene and/or ALK F1196M mutant gene and/or EML4-ALK mutant gene and/or NPM-ALK mutant gene.

17. The method of claim 16, wherein the non-small cell lung cancer is advanced anaplastic lymphoma kinase-positive non-small cell lung cancer.

18. A pharmaceutical composition comprising the compound, or a pharmaceutically acceptable salt, solvate, ester, acid, metabolite or prodrug thereof of claim 1, a pharmaceutically acceptable carrier or excipient, and optionally one or more other therapeutic agents.

* * * * *